United States Patent
Breen

(10) Patent No.: US 12,188,094 B2
(45) Date of Patent: Jan. 7, 2025

(54) METHODS OF MAST CELL TUMOR PROGNOSIS AND USES THEREOF

(71) Applicant: North Carolina State University, Raleigh, NC (US)

(72) Inventor: Matthew Breen, Apex, NC (US)

(73) Assignee: North Carolina State University, Raleigh, NC (US)

(*) Notice: Subject to any disclaimer, the term of this patent is extended or adjusted under 35 U.S.C. 154(b) by 784 days.

(21) Appl. No.: 17/216,170

(22) Filed: Mar. 29, 2021

(65) Prior Publication Data

US 2021/0238695 A1    Aug. 5, 2021

Related U.S. Application Data

(62) Division of application No. 16/305,315, filed as application No. PCT/US2017/034711 on May 26, 2017, now Pat. No. 10,961,591.

(60) Provisional application No. 62/343,503, filed on May 31, 2016.

(51) Int. Cl.
  C12Q 1/68      (2018.01)
  C07H 21/04    (2006.01)
  C12Q 1/6886   (2018.01)

(52) U.S. Cl.
  CPC ....... *C12Q 1/6886* (2013.01); *C12Q 2537/16* (2013.01); *C12Q 2600/118* (2013.01); *C12Q 2600/156* (2013.01)

(58) Field of Classification Search
  None
  See application file for complete search history.

(56) References Cited

U.S. PATENT DOCUMENTS

| | | | |
|---|---|---|---|
| 6,905,823 | B2 | 6/2005 | Kallioniemi et al. |
| 7,930,104 | B2 | 4/2011 | Baker et al. |
| 7,960,110 | B2 | 6/2011 | Bastian et al. |
| 9,090,945 | B2 | 7/2015 | Breen |
| 9,290,814 | B2 | 3/2016 | Giafis et al. |
| 10,501,806 | B2 | 12/2019 | Breen |
| 10,513,738 | B2 | 12/2019 | Breen |
| 10,961,591 | B2 | 3/2021 | Breen |
| 2007/0275403 | A1 | 11/2007 | Morrison et al. |
| 2009/0155805 | A1 | 6/2009 | Zhang et al. |
| 2009/0299640 | A1 | 12/2009 | Ellis et al. |
| 2009/0324596 | A1 | 12/2009 | Kang et al. |
| 2013/0210014 | A1 | 8/2013 | Sharman |

(Continued)

FOREIGN PATENT DOCUMENTS

| | | |
|---|---|---|
| EP | 2513340 B1 | 6/2016 |
| WO | WO2002/077197 | 10/2002 |

(Continued)

OTHER PUBLICATIONS

Thomas et al. (J. of Heredity, Am. Genetic Association, vol. 98, No. 5, pp. 474-484, 2007). (Year: 2007).*

(Continued)

*Primary Examiner* — Jeanine A Goldberg
(74) *Attorney, Agent, or Firm* — Jenkins, Taylor & Hunt, P.A.

(57) ABSTRACT

The present disclosure provides methods for detecting a high-risk phenotype of a mast cell tumor (MCT) in a biological sample from a mammal, preferably a dog. Kits, PCR probes and primers to detect high-risk MCT are also provided.

9 Claims, 11 Drawing Sheets

Figure 1:
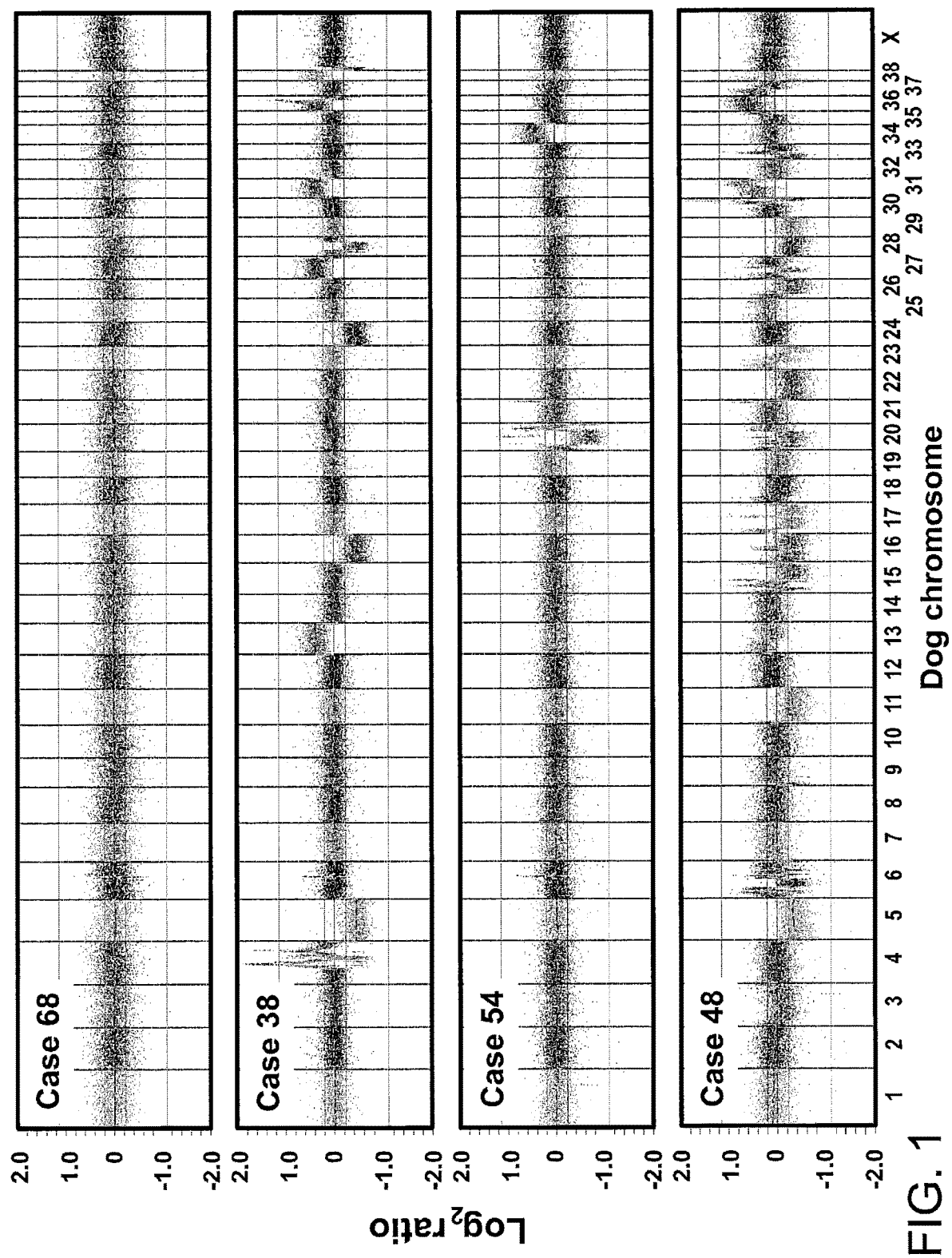

Specification includes a Sequence Listing.

(56) References Cited

U.S. PATENT DOCUMENTS

| | | |
|---|---|---|
| 2016/0289767 A1 | 10/2016 | Breen |
| 2017/0037481 A1 | 2/2017 | Breen |
| 2017/0211150 A1 | 7/2017 | Breen |
| 2019/0185943 A1 | 6/2019 | Breen |
| 2020/0109457 A1 | 4/2020 | Breen |
| 2020/0181719 A1 | 6/2020 | Breen |
| 2021/0238695 A1 | 8/2021 | Breen |

FOREIGN PATENT DOCUMENTS

| | | |
|---|---|---|
| WO | WO 2002/100246 | 12/2002 |
| WO | WO 2009/051842 | 4/2009 |
| WO | WO2012/078053 | 6/2012 |
| WO | WO 2012/135125 | 10/2012 |
| WO | WO 2017/210115 | 12/2017 |

OTHER PUBLICATIONS

Hedan et al. (BMC Cancer, vol. 11, pp. 1-14, May 26, 2011). (Year: 2011).*

Milne et al. (Chromosome Research, vol. 12, pp. 825-835, 2004). (Year: 2004).*

Jark et al. (Research in Veterinary Science, vol. 111, pp. 26-30, Epublished Nov. 17, 2016). (Year: 2016).*

Mochizuki et al. (Chromosome Res vol. 25, pp. 129-143, published online Jan. 5, 2017). (Year: 2017).*

Al Mulla et al., "Genetic profiling of stage I and II colorectal cancer may predict metastatic relapse," Modern Pathology. vol. 19, No. 5 pp. 648-658 (2006).

Angstadt et al., "Characterization of canine osteosarcoma by array comparative genomic hybridization and RT-qPCR: signature of genomic imbalance in canine osteosarcoma parallel the human counterpart." Genes Chromosomes Cancer, vol. 50, pp. 859-874 (2015).

Angstadt, Andrea Y. et al.; "A genome-wide approach to comparative oncology: high-resolution oligonucleotide aCGH of canine and human osteosarcoma pinpoints shared microaberrations," Cancer Genetics, 2012.

Arendt et al., "Genome-Wide Association Study of Golden Retrievers Identifies Germ-Line Risk Factors Predisposing to Mast Cell Tumours." PLoS Genet, vol. 11, Article ID e1005647 (2015).

Bowman et al. (Molecular Evaluation of Canine Urothelial Carcinoma and the Cell line Model, NCSU CVM Annual Research Forum Award of Excellence for Poster presentation, Feb. 2013). (Year: 2013).

Breen et al. "An integrated 4249 marker FISH/RH map of the canine genome." BMC Genomics 5(1):65 (2004).

Breen et al. "Chromosome-Specific Single-Locus FISH Probes Allow Anchorage of an 1800-Marker Integrated Radiation-Hybrid/Linkage Map of the Domestic Dog Genome to All Chromosomes", Genome Research, 11:784-1795 (2001).

Breen, "Update on genomics in veterinary oncology." Top Companion Anim Med, vol. 24, pp. 113-121 (2009).

Breen, M., "Evolutionarily conserved cytogenetic changes in hematological malignancies of dogs and humans—man and his best friend share more than companionship," vol. 16, No. 1, pp. 145-154 (Feb. 25, 2008).

Brown, Subtelomeric chromosome rearrangements are detected using an innovative 12-color FISH assay (M-TEL), Nature Medicine, vol. 7, No. 4, pp. 497-501 (2001).

Choi, et al., "Color Compensation of Multicolor FISH Images", IEEE Transactions on Medical Imaging, vol. 28, No. 1, pp. 129-136 (2009).

Decision to grant a European patent pursuant to Article 97(1) EPC for European Patent Application No. 10861217.7 dated Jun. 2, 2016.

Decision to Grant corresponding to European U.S. Appl. No. 14/861,374 dated Dec. 10, 2020.

European Search Report corresponding to European Patent Application No. 10861217.7-1403/2513340 dated Jun. 3, 2013.

European Search Report corresponding to European Patent Application No. 17807289.8 dated Jan. 10, 2020.

Extended European Search Report issued in counterpart European Application No. 14861374.8 dated May 29, 2017 eleven (11) pages).

Giantin et al., "Global gene expression analysis of canine cutaneous mast cell tumor: could molecular profiling be useful for subtype classification and prognostication?" PLoS One, vol. 9, Article ID e95481 (2014).

Haenisch et al., "Systemic mast cell activation disease: the role of molecular genetic alterations in pathogenesis heritability and diagnostics." Immunology, vol. 137, pp. 197-205 (2012).

Hahn et al., "Diagnostic and Prognostic Importance of Chromosomal Aberrations Identified in 61 Dogs with Lymphosarcoma," Veterinary Pathology, vol. 31, No. 5, pp. 528-540 (Sep. 1, 1994).

Hedan et al. (2011) Molecular cytogenetic characterization of canine histiocytic sarcoma: A spontaneous model for human histiocytic cancer identifies deletion of tumor suppressor genes and highlights influence of genetic background on tumor behavior. BMC Cancer, vol. 11, pp. 1-14.

Intention to Grant corresponding to European Patent Application No. 14861374.8 dated Jan. 7, 2020.

International Preliminary Report dated Feb. 2, 2017 from related International Application No. PCT/US2015/41988.

International Preliminary Report on Patentability for related PCT Application No. PCT/US2014/065773 dated May 17, 2016.

International search report and the written opinion of the international searching authority for a related PCT Application No. PCT/US2014/065773 dated May 21, 2015.

International Search Report and Written Opinion dated Jul. 2, 2015 from related International Application No. PCT/US2015/025916.

International Search Report and Written Opinion dated Oct. 30, 2015 from related International Application No. PCT/US2015/41988.

International Search Report and Written Opinion issued in PCT Application No. PCT/US2017/034711 dated Sep. 14, 2017 (six (6) pages).

Johnson et al., "Chemotherapy for Dogs with Mast Cell Tumors Approved by the FDA," Advances in Small Animal Medicine and Surgery, vol. 23., No. 1 (2010).

Karlin-Neumann al. (2012). Probing copy number variations using Bio-Rad's QX100™ Droplet Digital™ PCR system. Bio-Rad Bulletin 6277.

Kennedy et al., "Genome-wide DNA copy number analysis and targeted transcriptional analysis of canine histiocytic malignancies identifies diagnostic signatures and highlights disruptions of spindle assembly complex," Chromosome Res. vol. 27, pp. 179-202 (2019).

Koenig, A.; "Expression and Significance of p53, Rb, p21/waf-1, p16/ink-4a, and PTEN Tumor Suppressors in Canine Melanoma," Vet Pathol. 39: 458-472 (2002).

Letard et al.,(2008) "Gain-of-function mutations in the extracellular domain of KIT are common in canine mast cell tumors." Mol Cancer Res, vol. 6, pp. 10 Pages.

Lin et al., "Generation and characterization of novel canine malignant mast cell line CL1." Vet Immunol Immunopathol, vol. 127, pp. 114-124 (2009).

Lin Tzu-Yin et al., "Targeting canine bladder transitional cell carcinoma with a human bladder cancer-specific ligand", Molecular Cancer, Biomed Central, London, GB, vol. 10, No. 1, Jan. 27, 2011 ( Jan. 27, 2011), age 9, XP02108845 9, ISSN: 1476-4598, DOI: 10.1186/1476-4598-10-9.

Magdy Sayed Aly et al: "Chromosomal aberrations in early-stage bilharzia! bladder cancer", Cancer Genetics and Cytogenetics., vol. 132, No. 1, Jan. 1, 2002 (Jan. 1, 2002), pp. 41-45, XP055372968, us SSN: 0165-4608, DOI: 10. 1016/S0165-4608(01)00527-1.

Maria I. Stamouli et al: "Detection of genetic alterations in primary bladder carcinoma with dual-color and multiplex ftuorescence in situ hybridization", Cancer Genetics and Cytogenetics., vol. 149, No. 2, Mar. 1, 004 (Mar. 1, 2004), pp. 107-113, XP055372972, us ISSN: 0165-4608, DOI: 10. 1016/S0165-4608(03)00303-0.

Marin-Aguilera Mercedes et al: "Utility of Fluorescence in Situ Hybridization as a Non-invasive Technique in he Diagnosis of Upper Urinary Tract Urothelial Carcinoma", European Urology,

(56) References Cited

OTHER PUBLICATIONS vol. 51, No. 2, Aug. 22, 2006Aug. 22, 2006), pp. 409-415, XP029850986, ISSN: 0302-2838, DOI: 10.1016/J.EURUR0.2006.08.045.

Milne et al., "Karyotype of canine soft tissue sarcomas: a multicolour, multi-species approach to canine chromosome painting", Chromosome Research, vol. 12 pp. 825-835 (2004).

Mochizuki et al., "Detection of Copy Number Imbalance in Canine Urothelial Carcinoma With Droplet Digital Polymerase Chain Reaction." Vet Pathol, vol. Nov. 2015 (2015).

Modiano et al., "Predictive value of p16 or Rb inactivation in a model of naturally occurring canine non-Hodgkin's lymphoma," Leukemia. vol. 21, No. 1 pp. 184-187 (2007).

Muller et al. (2012) Genetic characterization via array based comparative genomic hybridization. Tierarztliche Praxis. 40(1):55-58.

Mullins et al. "Agreement in Breast Cancer Classification between Microarray and Quantitative Reverse Transcription PCR from Fresh-Frozen and Formalin-Fixed, Paraffin-Embedded Tissues" Clin Chem. 53(7): 1273-1279 (2007).

Notice of Acceptance corresponding to Australian Patent Application No. 2014348428 dated Dec. 7, 2020.

Notice of Allowability corresponding to U.S. Appl. No. 15/037,438 dated Jul. 31, 2019.

Notice of Allowance corresponding to Canadian Patent Application No. 2,785,999 dated Nov. 10, 2020.

Notice of Allowance corresponding to Japanese Patent Application No. 2016-554527 dated Feb. 5, 2019.

Notice of Allowance corresponding to U.S. Appl. No. 15/037,438 dated Jun. 7, 2019.

Notice of Allowance corresponding to U.S. Appl. No. 15/328,733 dated Jul. 16, 2019.

Notice of Allowance corresponding to U.S. Appl. No. 15/304,388 dated Jul. 24, 2019.

Notice of Publication corresponding to U.S. Appl. No. 16/659,095 dated Apr. 9, 2020.

Notice of Publication corresponding to U.S. Appl. No. 16/707,745 dated Jun. 11, 2020.

Notice of Publication corresponding to U.S. Appl. No. 16/725,195 dated Jul. 31, 2020.

Notice of Publication Corresponding to U.S. Appl. No. 17/216,170 dated Aug. 6, 2021.

Notification Concerning Transmittal of International Preliminary Report on Patentability (Chapter I of the Patent Cooperation Treaty) corresponding to International Patent Application No. PCT/US2010/060292 dated Aug. 30, 2012.

Notification of Transmittal of the International Search Report and the Written Opinion of the International Searching Authority, or the Declaration corresponding to International Patent Application No. PCT/US2010/060292 dated Apr. 10, 2012.

Office Action (Restriction Requirement) corresponding to U.S. Appl. No. 15/328,733 dated Apr. 27, 2018.

Office Action (Restriction Requirement) corresponding to U.S. Appl. No. 15/328,733 dated Feb. 15, 2019.

Office Action corresponding to Canadian Patent Application No. 2,785,999 dated Aug. 16, 2016.

Office Action corresponding to Japanese Patent Application No. 2016-554527 dated Sep. 25, 2018. (Translation).

Office Action corresponding to U.S. Appl. No. 13/515,614 dated Jul. 30, 2014.

Office Action corresponding to U.S. Appl. No. 15/037,438 dated Aug. 15, 2017.

Office Action corresponding to U.S. Appl. No. 15/037,438 dated May 23, 2018.

Office Action corresponding to U.S. Appl. No. 15/037,438 dated Jan. 8, 2019.

Office Action corresponding to U.S. Appl. No. 15/037,438 dated Nov. 24, 2017.

Office Action corresponding to U.S. Appl. No. 16/725,195 dated Apr. 5, 2022.

Office Action corresponding to U.S. Appl. No. 16/707,745 dated May 2, 2022.

Office Action corresponding to U.S. Appl. No. 16/659,095 dated Aug. 11, 2022.

Office Action corresponding to U.S. Appl. No. 16/725,195 date Nov. 7, 2022.

Office Action corresponding with European Patent Application No. 10861217.7-1403 dated Apr. 25, 2014.

Office Action corresponding to U.S. Appl. No. 16/707,745 dated Dec. 3, 2021.

Office Action corresponding with European Patent Application No. 14861374.8-1118 dated Apr. 4, 2019.

Oral Summons corresponding with European Patent Application No. 10861217.7-1403 dated Jun. 12, 2015.

Ratcliffe et al., "Proteomic identification and profiling of canine lymphoma patients," Veterinary and Comparative Oncology. vol. 7, No. 2 pp. 92-105 (2009).

Roode et al., "Genome-wide assessment of recurrent genomic imbalances in canine leukemia identifies evolutionarily conserved regions for subtype differentiations," Chromosome Research, Kluwer Academic Publishers, vol. 23, No. 4, pp. 681-708 (2015).

Roode, Sarah Culvar.; "Molecular Characterization of Canine Leukemia—Comparative Value and Clinical Applications," A dissertation submitted to the Graduate Faculty of North Carolina State University in partial fulfillment of the requirements for the degree of Doctor of Philosophy; Raleigh, North Carolina, 2014.

Sailasuta, A. et al. "The Relevance of CD117-Immunocytochemistry Staining Patterns to Mutational Exon-11 in c-kit Detected by PCR from Fine-Needle Aspirated Canine Mast Cell Tumor Cells" Veterinary Medicine International. vol. 2014. pp. 1-8 (eight (8) pages).

Seiser et al. "Reading between the lines: molecular characterization of five widely used canine lymphoid tumour cell lines." Veterinary and comparative oncology 11(1): 30-50 (2013).

Sotirakopolous et al.: "Evaluation of Microsatellite Instability in Urine for the Diagnosis of Transitional Cell Carcinoma of the Lower Urinary Tract in Dogs", J Vet Med, 24: 1445-1451 (2010).

Supplementary material for Thomas R, et al.; "Refining tumor-associated aneuploidy through 'genomic recoding' of recurrent DNA copy number aberrations in 150 canine non-Hodgkin lymphomas," Leukemia & Lymphoma, 2011.

Thomas et al. (2009) "Influence of genetic background on tumor karyotypes: evidence for breed-associated cytogenetic aberrations in canine appendicular osteosarcoma," Chromosome Research, vol. 10, 20 Pages.

Thomas et al., "A canine cancer-gene microarray for CGH analysis of tumors," Cytogenetic and Genome Research, vol. 102, No. 1-4, pp. 254-260 (2003).

Thomas et al., "A Cytogenetically Characterized, Genome-Anchored 10-M b BAC Set and CGH Array for the Domestic Dog", Journal of Heredity., vol. 98, No. 5, Jul. 23, 2007 (Jul. 23, 2007), pp. 474-484, XP055343142,3B ISSN: 0022-1503, DOI: 10.1093/jhered/esm053.

Thomas et al., "Chromosome aberrations in canine multicentric lymphomas detected with comparative genomic hybridisation and a panel of single locus probes," British Journal of Cancer. vol. 89, No. 8 pp. 1530-1537 (2003).

Thomas, Chromosome Res, vol. 22, No. 3, pp. 305-319, 2017 (Year: 2014).

Thomas, R., et al. "A genome assembly-integrated dog 1 Mb BAC microarray: a cytogenetic resource for canine cancer studies and comparative genomic analysis." Cytogenetic and genome research 122(2): 110-121 (2008).

Thomas, Rachael et al., "Construction of a 2-Mb resolution BAG microarray for CGH analysis of canine tumors," Genome Research, pp. 1832-1837, Dated Feb. 13, 2005, Revised May 4, 2005.

Urovysion Bladder Cancer Kit; < http://www.abbottmolecular.com> Accessed Nov. 11, 2013.

Urovysion Bladder Cancer Kit; Package Insert; Abbott Laboratories, 2006.

Winkler et al. (2006) Polysomy 13 in a canine prostate carcinoma underlining its significance in the development of prostate cancer. Cancer Genet. Cytogenet. 169:154-158.

(56) References Cited

OTHER PUBLICATIONS

Letard S. et al. "Gain-of-Function Mutations in the Extracellular Domain of KIT Are Common in Canine Mast Cell Tumors" Molecular Cancer Research. 2008 pp. 1137-1145 {ten (10) pages).
Lin et al. (Veterinary Immunology and Immunopathology, vol. 127, pp. 114-124, 2009) (Year: 2009).
Mochizuki, A. et al. "Detection of Copy Number Imbalance in Canine Urothelial Carcinoma With Droplet Digital Polymerase Chain Reaction" Oncology-Original Article. Veterinary Pathology_ 2016, vol. 53(4) pp. 764-772 (nine (9) pages).
Notice of Acceptance corresponding to Australian Patent Application No. 2014348248 dated Dec. 7, 2020.
Notice of Allowance corresponding to Canadian Patent Application No. 2,785,999 dated Dec. 8, 2020.
Thomas et al. (Chromosome Research, vol. 10, Apr. 1, 2009 (Year: 2009).
Thomas, Rachael, et al. "Refining tumor-associated aneuploidy through 'genomic receding' of recurrent DNA copy umber aberrations in 150 canine non-Hodgkin lymphomas." Leukemia & lymphoma 52(7): 1321-1335 (2011).
Intention to Grant (2nd) corresponding to European Patent Application No. 14861374.8 dated Jun. 18, 2020.
Intention to Grant corresponding to European Patent Application No. 17807289.8 dated Jan. 7, 2020.
Mutsaers, A.J., W.R. Widmer, and D.W. Knapp, Canine transitional cell carcinoma. J Vet Intern Med, 2003. 17(2): p. 136-44.
Notice of Allowance corresponding to U.S. Appl. No. 16/305,315 dated Nov. 18, 2020.
Office Action (Restriction Requirement) corresponding to U.S. Appl. No. 16/305,315 dated Jun. 15, 2020.
Office Action corresponding to Canadian Patent Application No. 3,025,776 dated Mar. 31, 2023.
Office Action and Interview Summary corresponding to U.S. Appl. No. 16/659,095 dated Apr. 28, 2023.
Office Action corresponding to U.S. Appl. No. 16/725,195 dated Jan. 23, 2024.
Office Action and Interview Summary corresponding to U.S. Appl. No. 16/659,095 dated May 24, 2024.
Supplemental Notice of Allowability corresponding to U.S. Appl. No. 16/305,315 dated Dec. 31, 2020.

\* cited by examiner

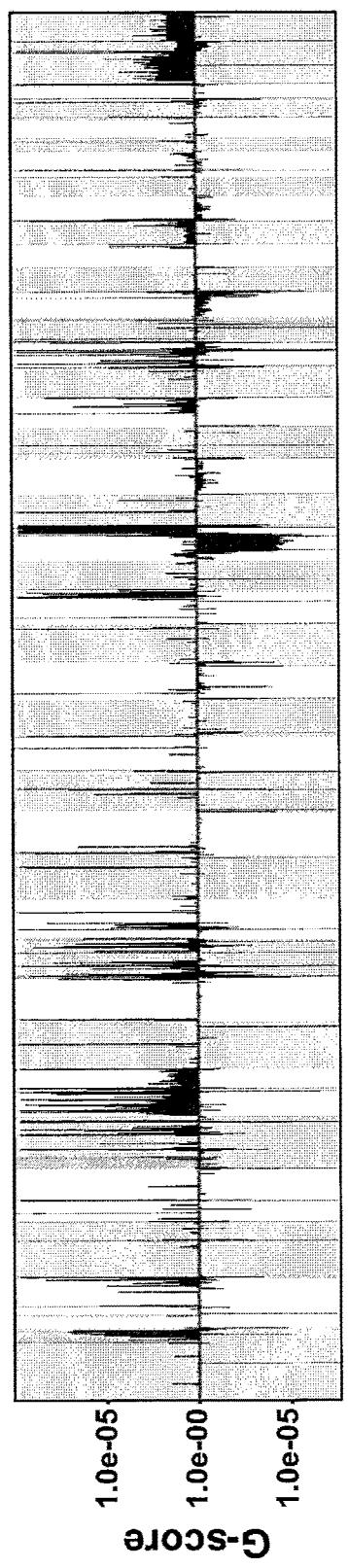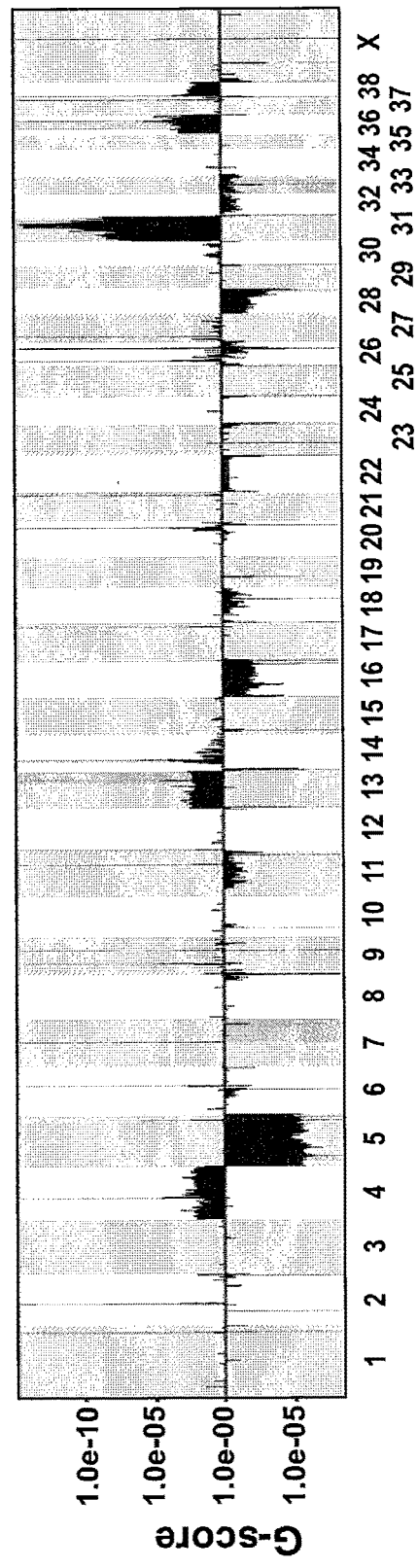
FIG. 5A  Wild-type *KIT* tumors
FIG. 5B  Mutant *KIT* tumors

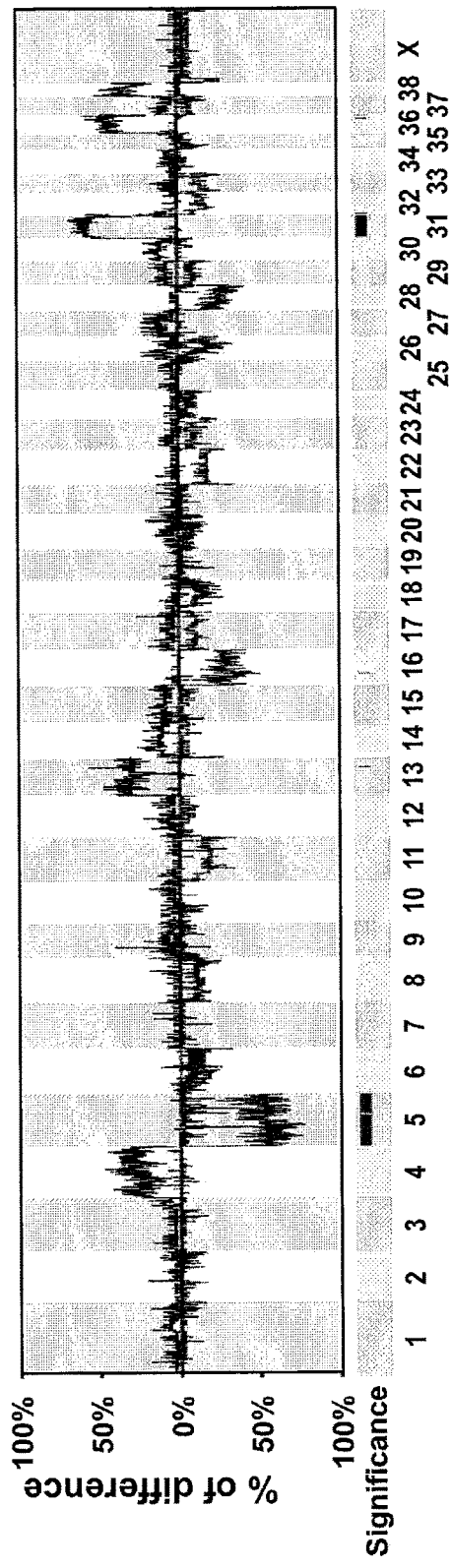
FIG. 6A KIT mutant tumors vs low-risk tumors
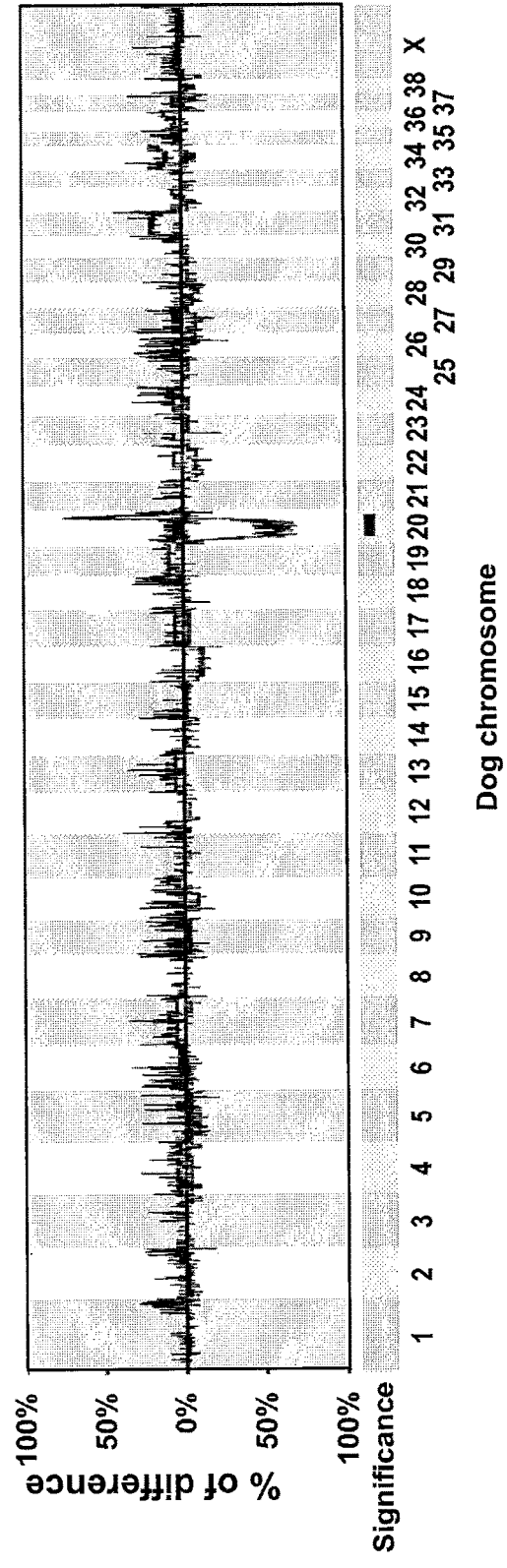
FIG. 6B High-grade tumors vs low-risk tumors

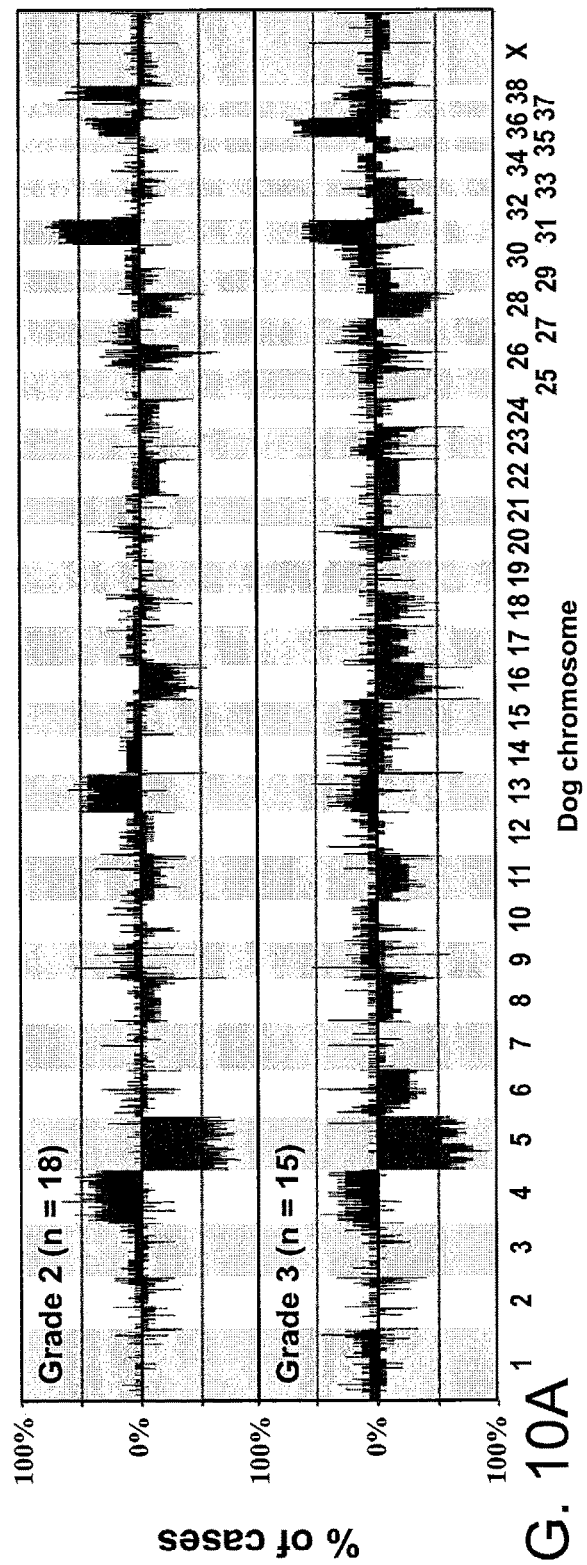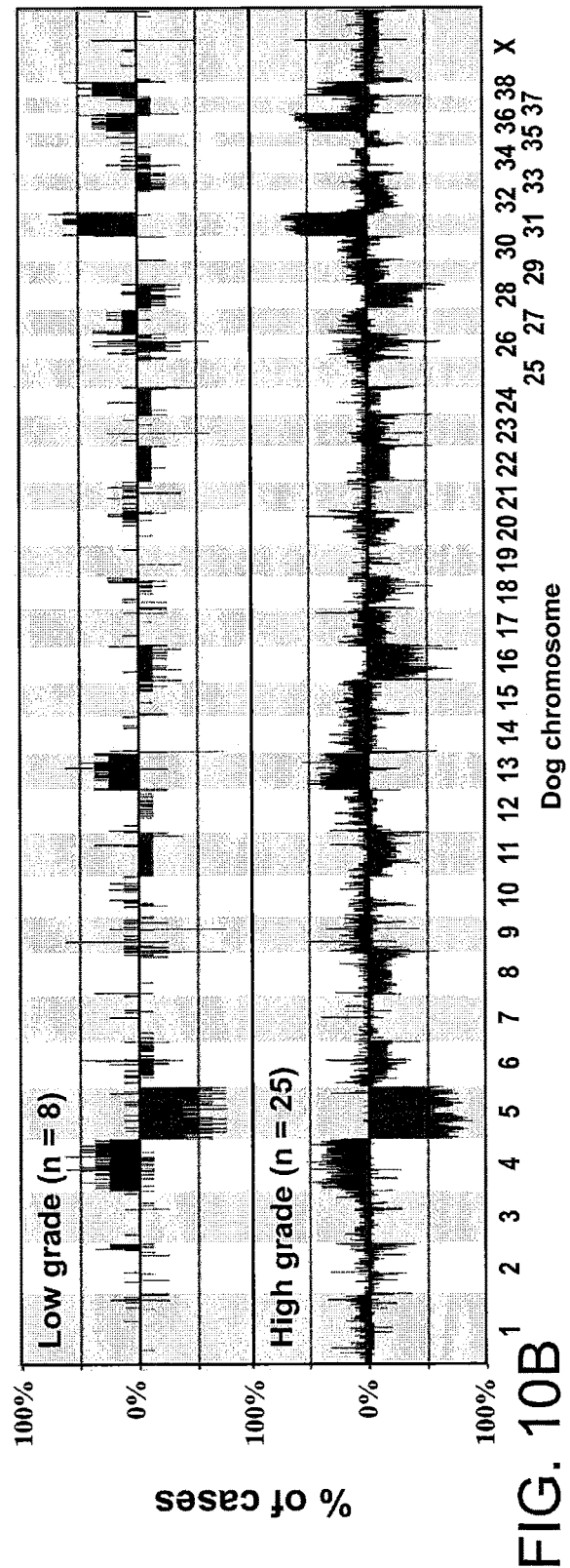

METHODS OF MAST CELL TUMOR PROGNOSIS AND USES THEREOF

CROSS REFERENCE TO RELATED APPLICATIONS

This application is a divisional of U.S. patent application Ser. No. 16/305,315, filed Nov. 28, 2018 (pending), which itself claims the benefit of U.S. Provisional Application Ser. No. 62/343,503, filed May 31, 2016, each of which is hereby incorporated by reference in its entirety.

1. FIELD

The present disclosure provides methods for detecting a high-risk phenotype of a mast cell tumor (MCT) in a biological sample from a mammal, preferably a dog. Kits, PCR probes and primers to detect high-risk MCT are also provided.

2. BACKGROUND 2.1. Introduction

Mast cell tumors (MCTs) are a common form of skin tumor in the domestic dog, accounting for up to 20% of all skin cancers in this species (Finnie and Bostock, 1979, Rothwell et al., 1987, Villamil et al., 2011). The clinical behavior of MCTs varies widely from benign tumors, which can be cured by surgical removal alone, to highly malignant tumors that exhibit aggressive biologic behavior and high rates of metastasis, even in dogs treated with a combination of surgery, radiation therapy and chemotherapy. This variable biological behavior of MCTs poses a clinical challenge to veterinary clinicians.

Treatment decisions are made based on the presence or absence of prognostic factors, such as histological grading, clinical stage, and expression of cell proliferation markers. Among many prognostic indicators, histopathological grading of tumors with Patnaik's 3-tier (grades 1-3, with grade 3 being the most malignant) and Kiupel's 2-tier grading (either low or high grade) schemes has been widely used for the prognostication and treatment decision (Patnaik et al., 1984, Kiupel et al., 2011). These schemes are based on consideration of histological features such as cellular morphology, mitotic index and extent of tissue involvement. These histological features, however, can be subjective, leading to inter-observer difference in grading. In addition, histopathological grading requires a tumor biopsy, which may involve general anesthesia and costly and potentially invasive surgical procedures. The need for a reliable, non-invasive prognostic test for canine MCTs remains paramount.

Numerical and structural chromosomal abnormalities are hallmarks of cancer. Such changes to the genome have been utilized widely as diagnostics and prognostics in a range of human cancers (Mitelman et al., 2007, Frohling and Dohner, 2008, Hanahan and Weinberg, 2011). Recent advancement in genomics technology now allows us to analyze the genetic abnormalities in the dog at a genome-wide level (Breen, 2009). DNA copy number changes correlated with prognosis have a potential to offer a molecular means of predicting outcome as well as identification of potential therapeutic targets. Genome-wide copy number analysis has thus far not been performed in canine MCTs, with the exception of a single MCT cell line (Lin et al., 2009).

3. SUMMARY OF THE DISCLOSURE

This disclosure is directed to a method for detecting a high-risk phenotype of a mast cell tumor (MCT) in a biological sample by enumeration of certain regions of certain dog chromosome (CFA) from a dog which comprises: (a) measuring copy numbers of regions of dog chromosome (CFA) CFA5:38, CFA 20:32, CFA 20:46, and CFA 31:18, in the biological sample; (b) comparing the measured copy numbers to those of appropriate canine normal controls; and (c) if the copy numbers of regions of CFA 31:18 and CFA 20:46 are increased and the copy numbers of regions of CFA5:38 and CFA 20:32 are reduced from that of the appropriate controls, detecting that the dog has increased likelihood of a high-risk phenotype of a mast cell tumor (MCT).

In one embodiment of the presently disclosed methods, the copy number increases are >1.5.

In another embodiment of the presently disclosed methods, the copy number reductions are <0.5. In yet another embodiment, both the copy number increases are >1.5 and the copy number reductions are <0.5.

In the presently disclosed methods, the copy numbers may be measured by fluorescence in situ hybridization (FISH); polymerase chain reaction (PCR), such as digital droplet PCR; comparative genomic hybridization (CGH); or next generation sequencing.

In the presently disclosed methods, the biological sample may be a tissue sample such as a fresh-frozen sample or a fresh sample or a fixed sample such as a formalin-fixed, paraffin-embedded (FFPE) sample.

The invention also provides a kit for detecting a high-risk phenotype of a mast cell tumor (MCT) in a biological sample in a dog comprising: (a) at least a plurality of reagents selected from the group consisting of: nucleic acid probes and/or primers capable of specifically detecting CFA5:38, CFA 20:32, CFA 20:46, and CFA 31:18; and (b) instructions for use in measuring a copy number of regions of CFA5:38, CFA 20:32, and CFA 20:46, and CFA 31:18 in a biological sample from a dog, wherein if the copy numbers of regions of CFA 20:46 and CFA 31:18 are increased and the copy numbers of regions of CFA5:38 and CFA 20:32 are reduced from that of measured copy numbers for appropriate controls, and detecting that the dog has increased likelihood of a high-risk phenotype of a mast cell tumor (MCT).

In the presently disclosed kits, the reagents may comprise primers with SEQ ID NOS:4-7 and 11-14 and probes with SEQ ID NOS:15-18.

The disclosure also provides a method for treating a dog with a mast cell tumor (MCT) which comprises: (a) measuring copy numbers of regions of CFA5:38, CFA 20:32, CFA 20:46, and CFA 31:18, in a biological sample from the dog; (b) comparing the measured copy numbers to those of appropriate canine normal controls; (c) if the copy numbers of regions of CFA 20:46 and CFA 31:18 are increased and the copy numbers of regions of CFA5:38 and CFA 20:32 are reduced from that of the appropriate controls, detecting that the dog has increased likelihood of a high-risk phenotype of a mast cell tumor (MCT); and (d) treating the dog with a chemotherapy regimen.

In the method of treatment, the chemotherapy regimen may comprise a treatment with an alkylating agent, a tyrosine kinase inhibitor, a vinca alkaloid or a combination thereof. The alkylating agent may be a nitrosourea such as lomustine. The tyrosine kinase inhibitor may be toceranib, masatinib, or imatinib. The vinca alkyloid may be vinblastine.

4. BRIEF DESCRIPTION OF THE FIGURES

FIG. 1: Representative oaCGH profiles of four canine MCT cases (Cases, 68, 38, 54 and 48) from the cohort used in the present study. In each case, the oaCGH profiles present the log 2 tumor/reference ratio on the y-axis and the genome coordinates of the ~180,000 probes on the custom array positioned by chromosome location across all 38 canine autosomes and X chromosomes on the x-axis. Histological grading and KIT mutational statuses were as follows: case 68, Grade 1/low grade (3-tier/2-tier grading system) tumor without KIT mutation; case 38, Grade 2/low grade tumor with KIT Exon 11 TD mutation; case 54, Grade 3/high-grade tumor without KIT mutation; case 48, Grade 3/high-grade tumor with KIT Exon 11 ITD mutation.

Figure 2A:
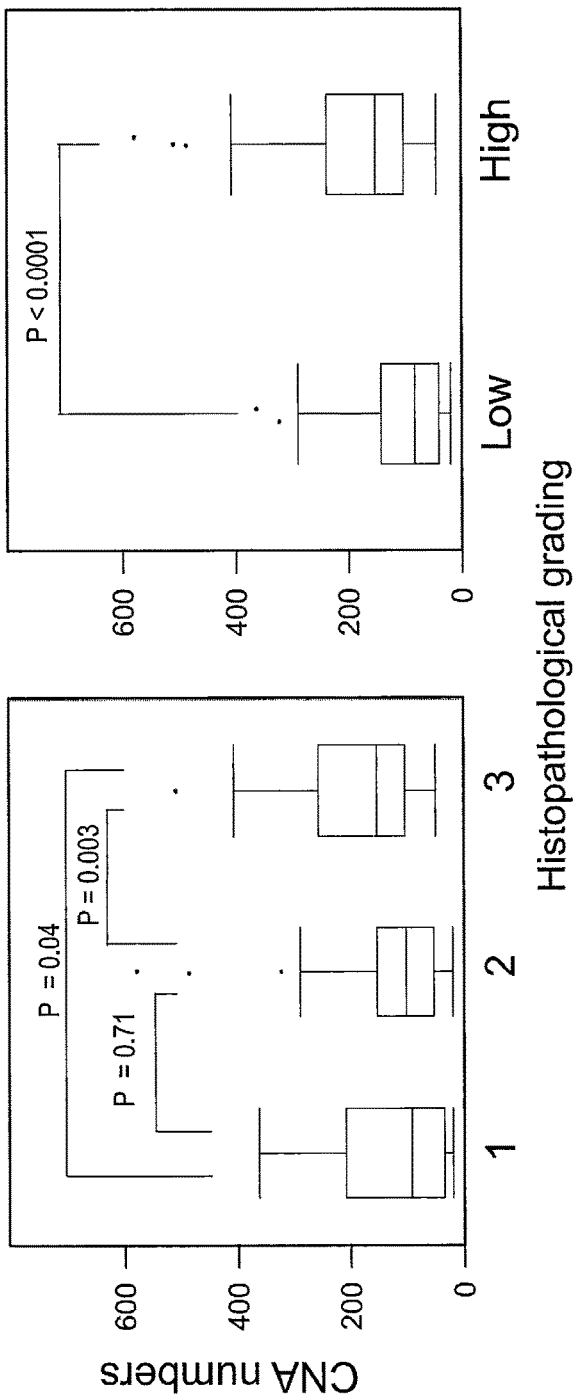
Figure 2B:
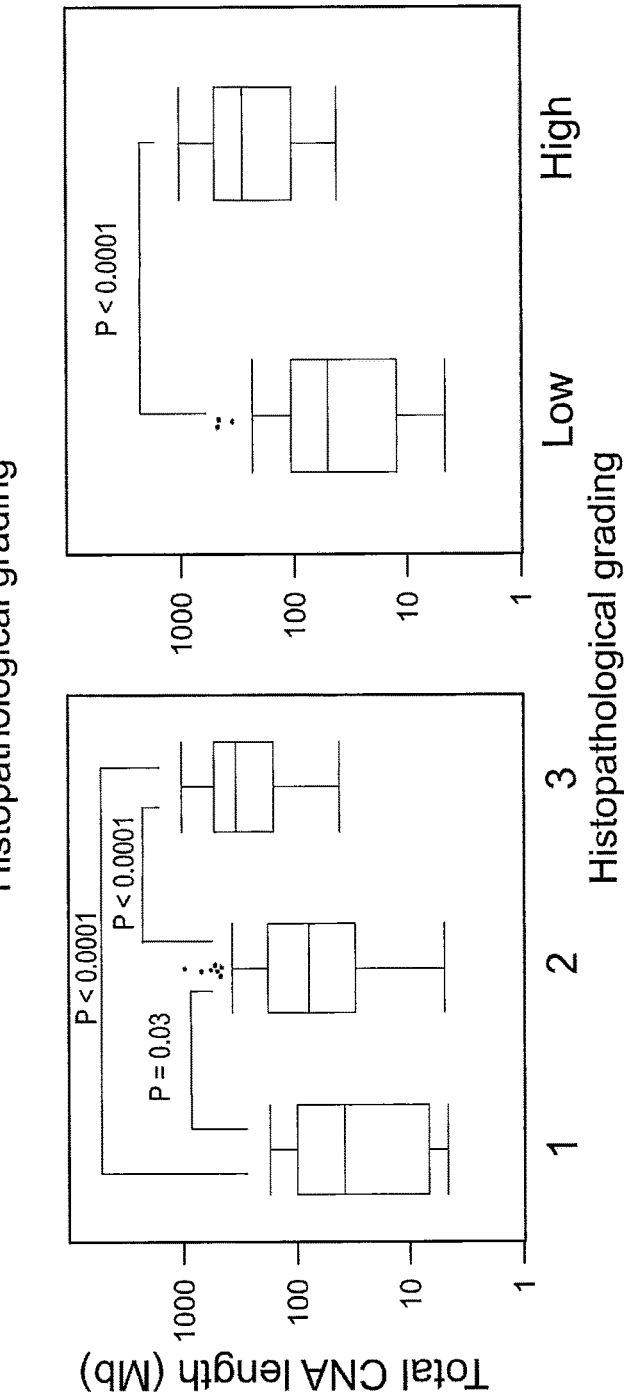

FIGS. 2A and 2B: Genomic imbalance in MCTs grouped by 3-tier (left) and 2-tier (right) histological grading. (2A) Numbers of copy number aberrations CNAs and (2B) total (combined) length of all CNAs was compared between groups stratified by histological grading.

Figure 3A:
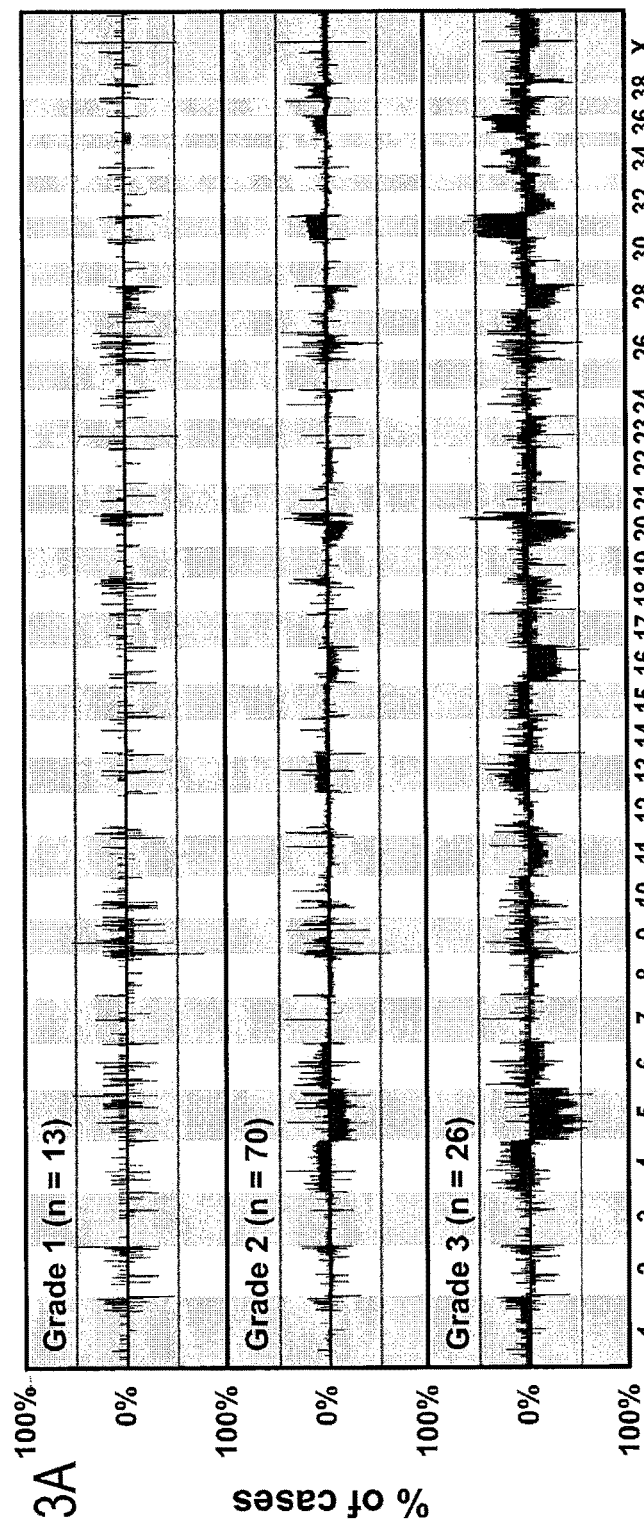
Figure 3B:
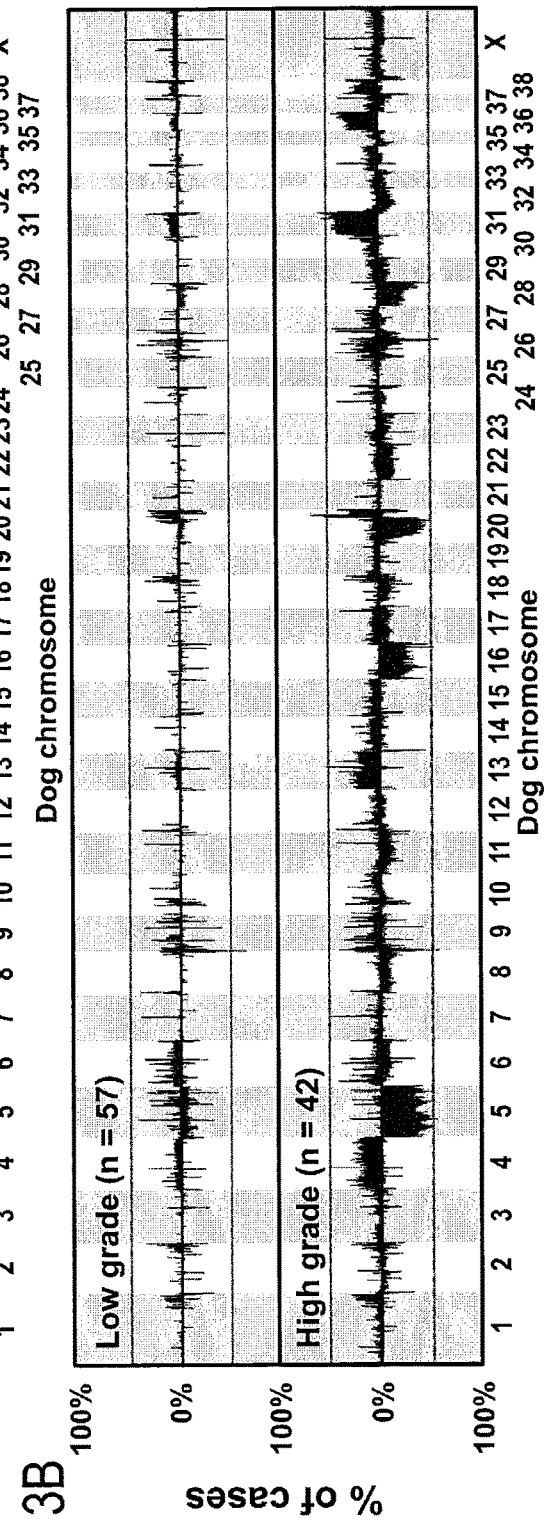

FIGS. 3A and 3B: Penetrance plots of genome-wide CNAs in canine MCTs, stratified by (3A) 3-tier and (3B) 2-tier grading schemes. Genomic locations are plotted along the x-axis. The y-axis indicates the percentage of corresponding cohort that demonstrated either copy number gain (shown in darker gray above the midline) or loss (shown in lighter gray below the midline) of the corresponding chromosome region. CNAs were more frequent in higher grade tumors.

Figure 4A:
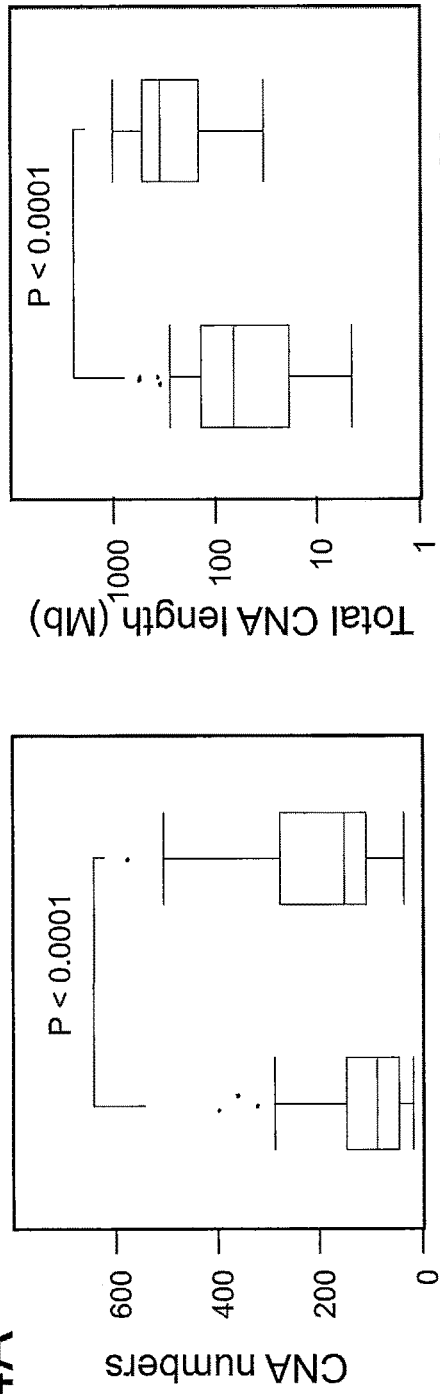
Figure 4B:
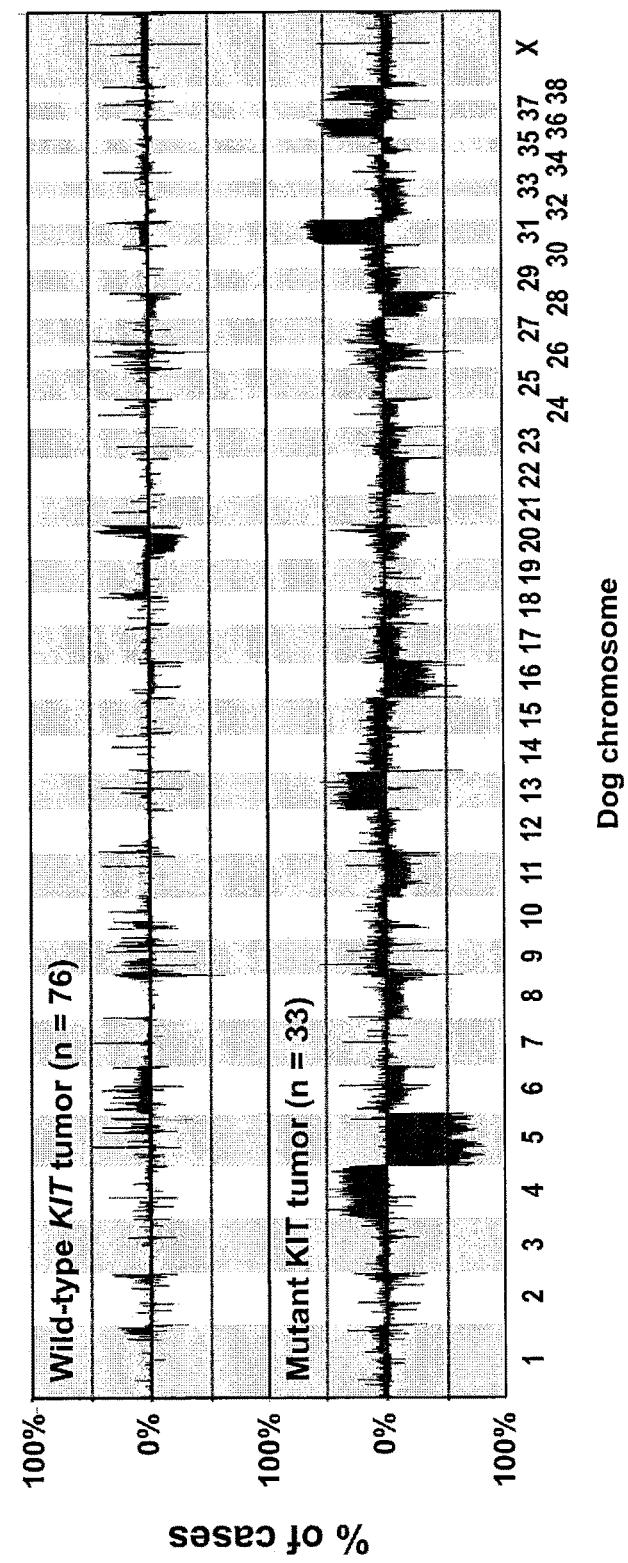

FIGS. 4A and 4B: Genomic imbalance in MCTs with wild-type KIT and tumors with mutant KIT. (4A) Numbers of CNAs and total CNA length was compared in tumors with and without KIT mutations. (4B) Penetrance plots of genome-wide CNAs in canine MCTs, stratified by KIT mutational status. Genomic locations are plotted along the x-axis. The y-axis indicates the percentage of corresponding cohort that demonstrated either copy number gain (shown in darker gray above the midline) or loss (shown in lighter gray below the midline) of the corresponding chromosome region. Canine MCTs without KIT mutations exhibited limited numbers of CNAs except for CFA 20. Canine MCTs with KIT mutations exhibited a wide range of CNAs with high frequencies, including gains of CFA 4, 13, 31, 36 and 38 and loss of 5, 16 and 28.

FIGS. 5A and 5B: GISTIC analysis of CGH profiles of MCTs with wild-type KIT and tumors with mutant KIT. The peak region of significance is highlighted in dark grey, flanked by a broader region of reduced significance shown in pale grey. Genomic locations are plotted along the x-axis, and G-scores for statistical significance are shown on the y-axis.

FIGS. 6A and 6B: Comparison analysis of penetrance plots of CNAs in high-risk and low-risk MCTs. The y-axis indicates the percentage of difference of CNA frequencies (darker gray: gain, lighter gray: loss) between two groups. Regions where CNA frequencies are significantly different between two groups are shown in darker gray (gain) or lighter gray (loss) above chromosome position. (6A) Comparison of KIT mutant tumors and low-risk tumors. (6B) Comparison of high-grade tumors and low-risk tumors.

Figure 7:
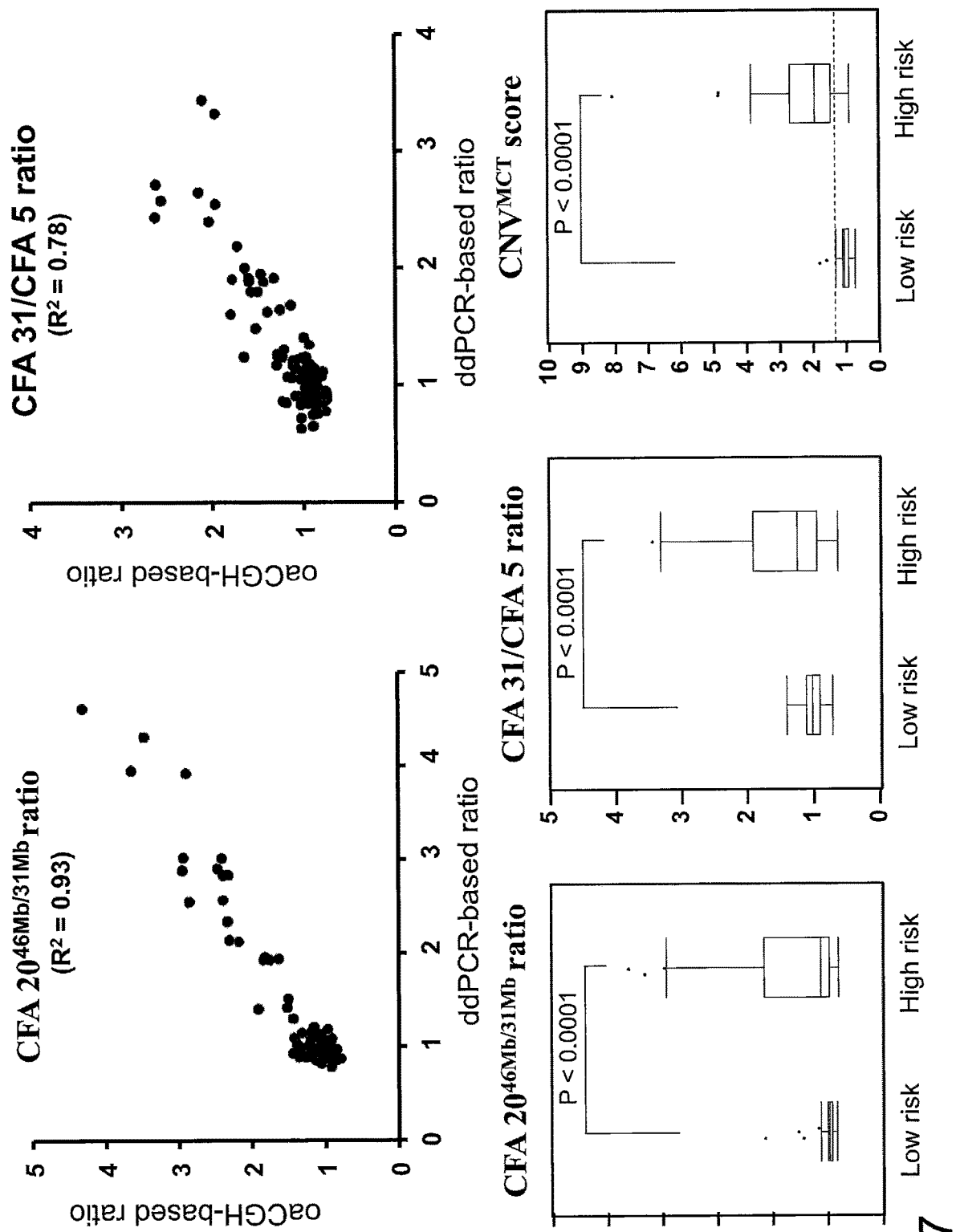

FIG. 7: Performance of the ddPCR assays. Upper two panels: correlation of ratios estimated with oaCGH and ddPCR (x-axis, ddPCR-based ratio; y-axis, oaCGH-based ratio). Lower three panels. Difference between low-risk and high-risk MCTs in CFA $20^{46Mb/31Mb}$ ratio, CFA 31/CFA 5 ratio and $CNA^{MCT}$ score. The broken line indicates the $CNA^{MCT}$ score cut-off value of 1.27, the threshold valued identified to separate low-risk and high-risk MCTs.

Figure 8A:
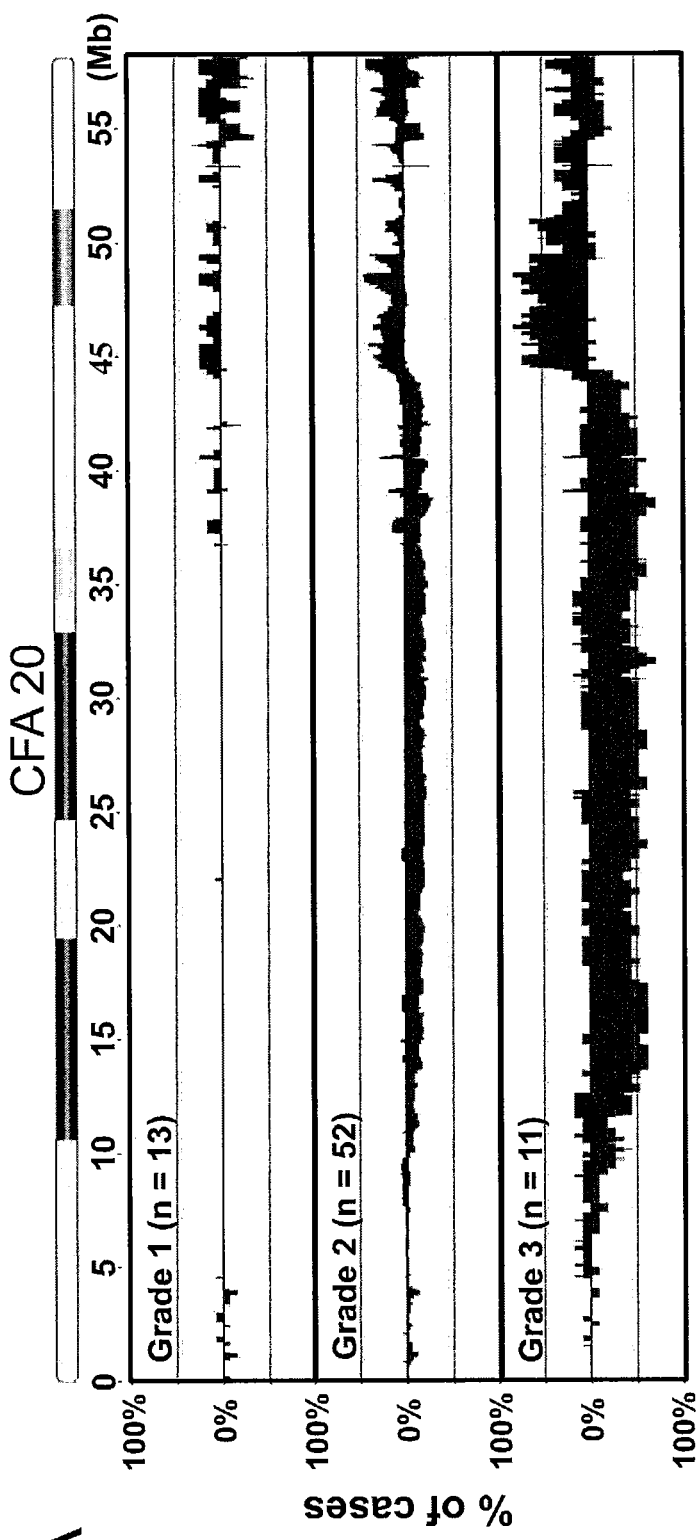
Figure 8B:
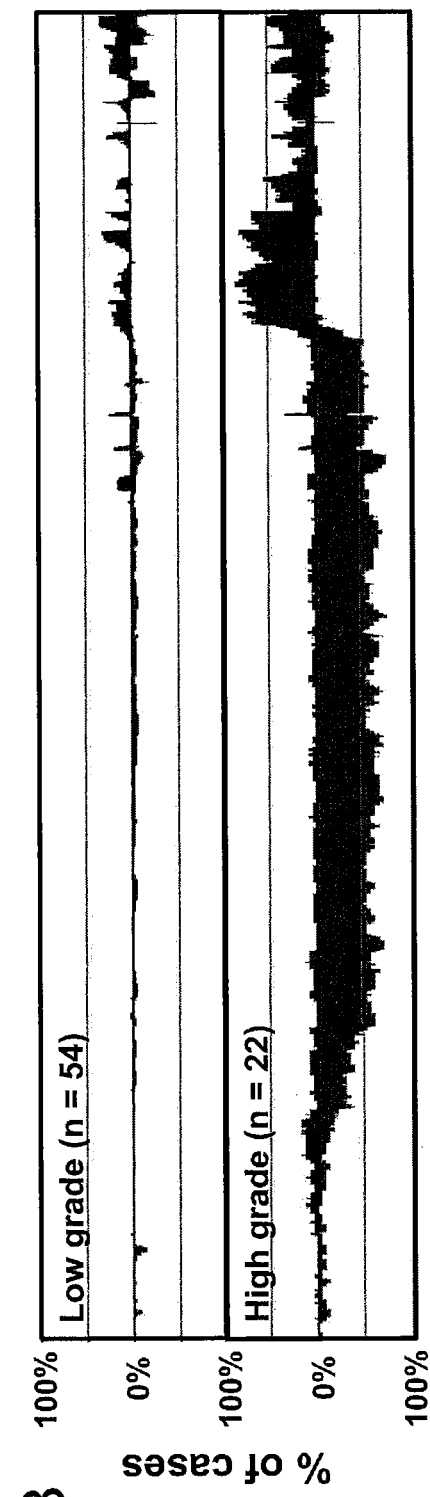

FIGS. 8A and 8B: Genomic imbalance in CFA 20 in MCTs with wild-type KIT gene, stratified by (8A) 3-tier and (8B) 2-tier histological grading. Frequency of loss of a middle segment of CFA 20 (15-43 Mb) and gain of a distal segment of CFA 20 (45-50 Mb) increased as histological grade increased.

Figure 9A:
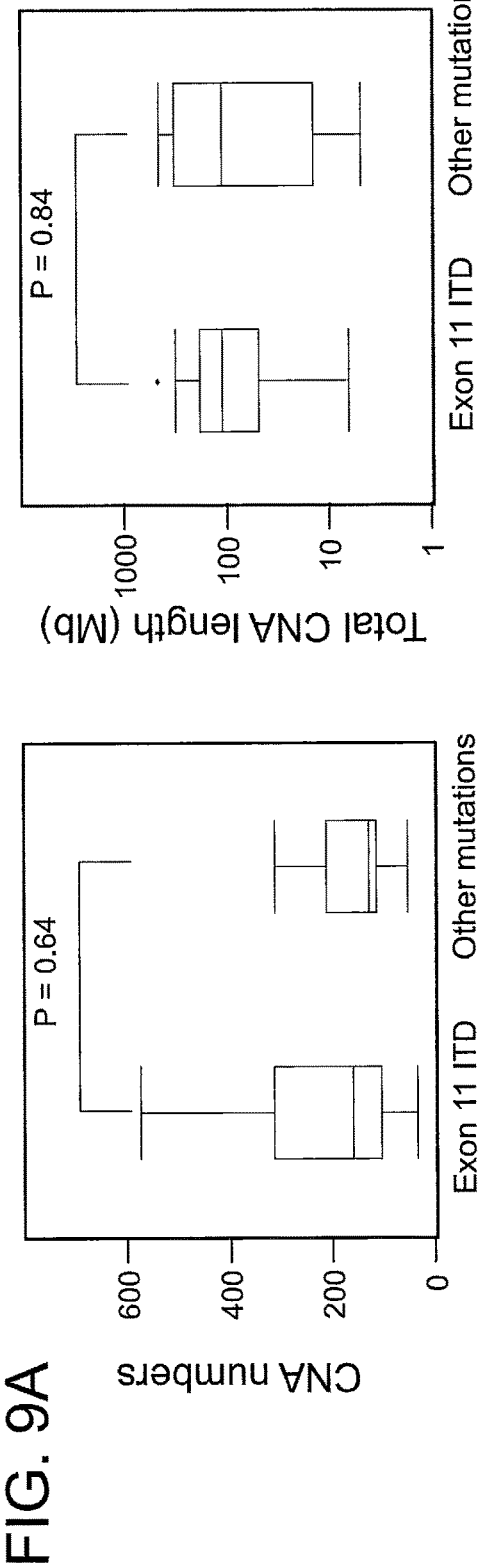
Figure 9B:
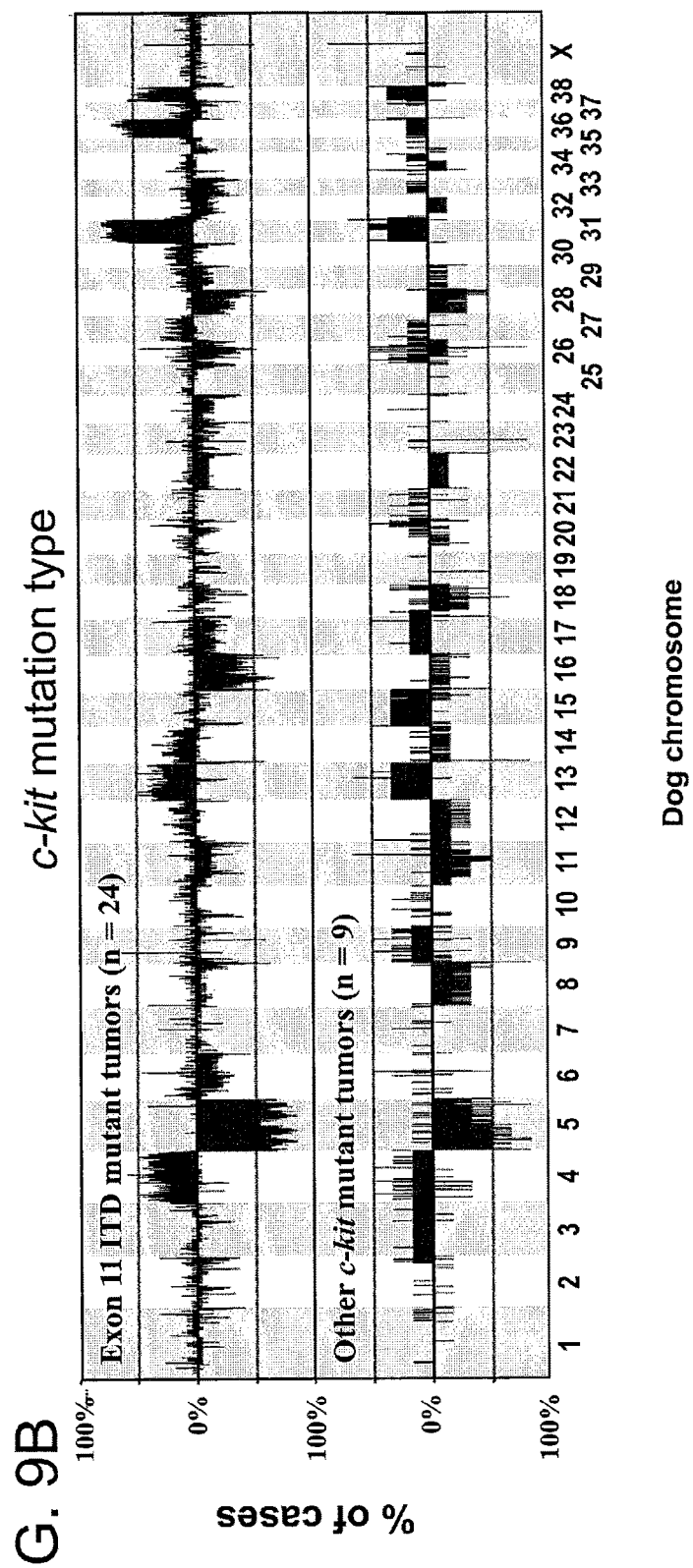

FIGS. 9A and 9B: Genomic imbalance in MCTs with exon 11 ITD mutations and tumors with other types of KIT mutation. (9A) Numbers of CNAs and total CNA length was compared in mutant KIT tumors by their mutational type. (9B) Penetrance plots of genome-wide CNAs in canine MCTs, stratified by KIT mutational type. Genomic locations are plotted along the x-axis. The y-axis indicates the percentage of corresponding cohort that demonstrated either copy number gain (shown in darker gray above the midline) or loss (shown in lighter gray below the midline) of the corresponding chromosome region.

FIGS. 10A and 10B: Penetrance plots of genome-wide CNAs in MCTs with KIT mutations, stratified by (10A) 3-tier and (OB) 2-tier grading schemes. Genomic locations are plotted along the x-axis. The y-axis indicates the percentage of corresponding cohort that demonstrated either copy number gain (shown in darker gray above the midline) or loss (shown in lighter gray below the midline) of the corresponding chromosome region.

Figure 11:
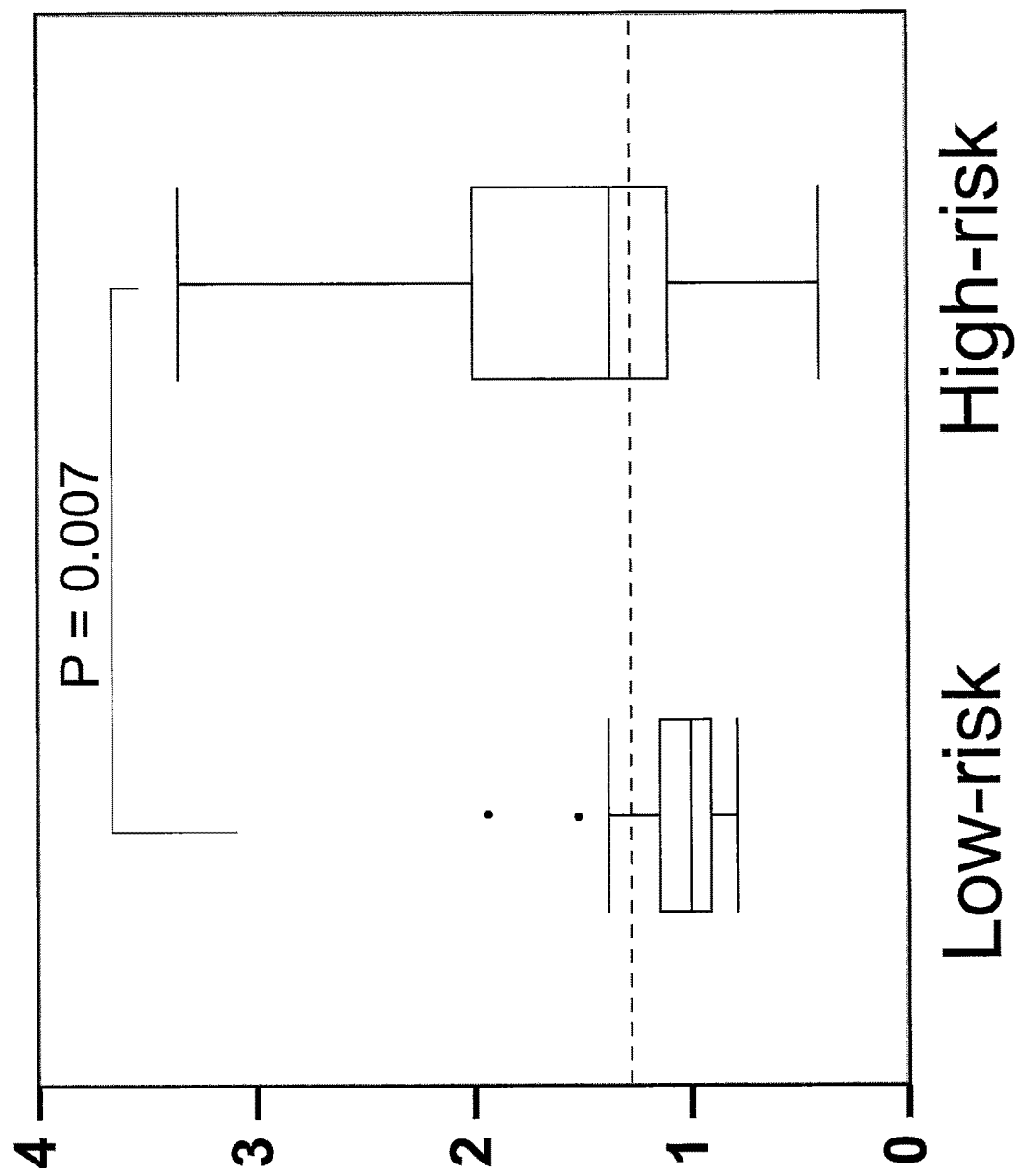

FIG. 11: The MCTCNA score in a validation cohort consisting of 38 MCT cases. High-risk MCTs exhibited significantly increased MCTCNA score compared to low-risk tumors. The broken line indicates the MCTCNA score cut-off value of 1.26, the threshold value used to separate low-risk and high-risk MCTs. Box plots indicate 25th to 75th percentiles with whiskers indicating the minimum and maximum values and with dots showing outliers

5. DETAILED DESCRIPTION OF THE DISCLOSURE

This disclosure provides a method for genomic profiling of canine mast cell tumors that identifies DNA copy number aberrations (CNAs) associated with aggressive tumor phenotype Briefly, canine mast cell tumor (MCT) is the most common skin malignancy in dogs and presents with heterogeneous biological behaviors, posing a clinical challenge to veterinary clinicians. Knowledge regarding the underlying molecular aberrations in the development and progression of MCTs are largely unknown. Characterization of genomic alterations in the tumors may identify genome regions and/or genes responsible for the malignant alteration of canine MCTs, facilitating the development of new therapeutic strategies and improved clinical management of this cancer. We performed genome-wide DNA copy number analysis of 109 canine primary MCTs using oligo array comparative genomic hybridization (oaCGH). We demonstrated a stepwise accumulation of numerical CNAs as tumor grade increases. Tumors with KIT mutations showed genome-wide aberrant copy number profiles, with frequent CNAs of genes in the p53 and RB pathways, whereas CNAs were less common in tumors with wild-type KIT. We evaluated the presence of four CNAs associated with high-risk tumor phenotypes as a means to predict aggressive tumors. Presence of these CNAs was able to predict high-risk phenotypes with a sensitivity of 75-91% and specificity of 86-93%, when using oaCGH and digital droplet PCR platforms. Further investigation of genome regions identified in this study may lead to the development of a molecular tool for classification and prognosis, as well as identification of therapeutic target molecules.

In this disclosure genome-wide DNA copy number profiling of a cohort of 109 primary MCTs, using oligo array comparative genomic hybridization (oaCGH) was performed. We identified a stepwise accumulation of CNAs in canine MCTs as tumor histological grade increases. We also demonstrated a strong correlation of several CNAs with the presence of KIT gene mutations, which is found in 20-30% of canine MCTs. Using four CNAs associated with high histological grade or KIT gene mutations, we developed and evaluated two simple digital droplet PCR (ddPCR) assays as a means to predict tumors with poor prognostic factors in 147 canine MCT specimens.

The relevant regions of CFA 5, CFA 20, & CFA 31 and more specifically the CFA 5:37 Mb, CFA 20:31 Mb, CFA 20:46 Mb and CFA 31:16 Mb regions may be found in Tables 3, 4, 5 and the Figures.

Method of detection: The copy number status of the regions assessed may be measured by, but is not limited to, fluorescence in situ hybridization (FISH), polymerase chain reaction (PCR), comparative genomic hybridization (CGH), or next generation sequencing (NGS). The biological sample must be a biopsy of the mass and may be a fresh sample, a fresh-frozen sample of the suspected mass, a sample in a preservative such as, for example, RNAlater, or a sample that has been processed for pathologic assessment. For example, the tissue specimen may have been soaked in one of several options to fix the tissues for histologic evaluation, such as, but not limited to, conventional histologic fixatives including, 10% neutral buffered formalin, B5, zinc-formalin. The sample may also have been soaked in formalin free fixatives such as, but not limited to, for example, 70% ethanol FineFIX, RCL-2 and HOPE.

The invention also provides a method of selecting treatment for a dog with MCT. The detection and quantification of the copy number status at regions of CFA 5, CFA 20 and CFA 31 would indicate the presence of a high-risk MCT and thus may be used to direct therapy accordingly. If the dog has MCT, the therapy may be, for example, surgical resection of the mass with wide margins, the extent of which is determined by the size and precise location of the mass, surgical resection followed by radiation therapy and/or chemotherapy such as, but not limited to, Vinblastine or Lumustine, and/or treatment with one or more tyrosine kinase inhibitors (TKIs) such as, toceranib (PALLADIA®) or masatinib (KINAVET®), and imatinib (GLEEVAC®).

5.1. Definitions

While the following terms are believed to be well understood by one of ordinary skill in the art, the following definitions are set forth to facilitate explanation of the presently disclosed subject matter.

Mast cells are derived from the bone marrow and can be found in various tissues throughout the body, generally residing in the connective tissues associated with the skin, lungs, nose, and mouth. The primary functions of mast cells are to aid tissue repair and the formation of new blood vessels and defend the body against parasitic infestations. In addition, mast cells contain several types of dark granules containing histamine and heparin, which are used by the body to modify immune reactions and inflammation. A "mast cell tumor" (MCT) is type of round-cell tumor containing mast cells, which may also be referred to as a mastocytoma. MCTs are found in humans and many animal species; in human medicine it also can refer to an accumulation or nodule of mast cells that resembles a tumor. MCTs are a common form of skin tumor in the domestic dog, accounting for up to 20% of all skin cancers in this species. The clinical behavior of MCTs varies widely from benign tumors, which can be cured by surgical removal alone, to highly malignant tumors that exhibit aggressive biologic behavior and high rates of metastasis, even in dogs treated with a combination of surgery, radiation therapy and chemotherapy.

"Copy number" is a measurement of DNA, whether of a single locus, one or more loci, or an entire genome. A "copy number" of two is "wild-type" in a dog (because of diploidy, except for sex chromosomes). A "copy number" of other than two in a dog (except for sex chromosomes) deviates from wild-type. Such deviations include gains, i.e., increases in copy number generally up to 5 copies per cell, deletions, i.e., decreases in copy number, i.e., either 1 or 0 copies per cell, and amplifications, i.e., increases in copy number generally in excess of 5 copies per cell.

"Labeled," "labeled with a detectable label," and "detectably labeled" are used interchangeably herein to indicate that an entity (e.g., a probe) can be detected. "Label" and "detectable label" mean a moiety attached to an entity to render the entity detectable, such as a moiety attached to a probe to render the probe detectable upon binding to a target sequence. The moiety, itself, may not be detectable but may become detectable upon reaction with yet another moiety. Use of the term "detectably labeled" is intended to encompass such labeling.

The detectable label can be selected such that the label generates a signal, which can be measured and the intensity of which is proportional to the amount of bound entity. A wide variety of systems for labeling and/or detecting molecules, such as nucleic acids, e.g., probes, are well-known. Labeled nucleic acids can be prepared by incorporating or conjugating a label that is directly or indirectly detectable by spectroscopic, photochemical, biochemical, immunochemical, electrical, optical, chemical or other means. Suitable detectable labels include radioisotopes, fluorophores, chromophores, chemiluminescent agents, microparticles, enzymes, magnetic particles, electron dense particles, mass labels, spin labels, haptens, and the like. Fluorophores and chemiluminescent agents are preferred herein.

"Nucleic acid sample" refers to a sample comprising nucleic acid in a form suitable for hybridization with a probe, such as a sample comprising nuclei or nucleic acids isolated or purified from such nuclei. The nucleic acid sample may comprise total or partial (e.g., particular chromosome(s)) genomic DNA, total or partial mRNA (e.g., particular chromosome(s) or gene(s)), or selected sequence(s). Condensed chromosomes (such as are present in interphase or metaphase) are suitable for use as targets in in situ hybridization, such as FISH.

"Predetermined cutoff" and "predetermined level" refer generally to a cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.).

"Probe," in the context of the present disclosure, is an oligonucleotide or polynucleotide that can selectively hybridize to at least a portion of a target sequence under conditions that allow for or promote selective hybridization. In general, a probe can be complementary to the coding or sense (+) strand of DNA or complementary to the non-coding or anti-sense (−) strand of DNA (sometimes referred to as "reverse-complementary"). Probes can vary significantly in length. A length of about 10 to about 100 nucleotides, such as about 15 to about 75 nucleotides, e.g., about 15 to about 50 nucleotides, can be preferred in some applications such as PCR, whereas a length of about 50 to about 1×10⁶ nucleotides can be preferred for chromosomal probes and a length of about 5,000 to about 800,000 nucleotides or more preferably about 75,000 to about 200,000 for BAC probes.

The invention encompasses fragments of nucleic acids that can serve (1) as probes for detecting segments of domestic dog (*Canis familairis*, CFA) genome referred to as chromosomes 5, 20 or 31 (hereafter referred to as CFA 5, CFA 20 and CFA 31). The dog genome has been sequenced and is available for example, USCS canfam2 at http://genome.ucsc.edu/cgi-bin/hgGateway?db=canFam2 and the NCBI *Canis lupus familiaris* genome database; or ENSEMBL database CanFam3.1 (GCA_000002285.2). See also, Lindblad-Toh et al. 2005 "Genome sequence, comparative analysis and haplotype structure of the domestic dog" Nature 438 (7069), 803-819.

The changes in copy number of regions of CFA 5, CFA 20 and/or CFA 31 may be detected by a number of methods well known in the art, e.g., Southern and northern blotting, dot blotting, colony hybridizations, hybridization to an array, comparative genomic hybridization (CGH), etc. or (2) as polymerase chain reaction (PCR) primers to amplify CFA 5, CFA 20 and/or CFA 31. PCR primers can comprise, in addition to CFA 5, CFA 20 and/or CFA 31 nucleic acid sequences, other sequences such as restriction enzyme cleavage sites that facilitate the use of the amplified nucleic acid. PCR is described in the following references: Saiki et al. 1988 *Science* 239 487-491; *PCR Technology*, Erlich, ed., Stockton Press, (1989). As explained below, PCR can be useful to detect abnormally low or high levels of target regions of chromosomes including CFA 5, CFA 20 and/or CFA 31.

Hybridization techniques are well known in the art and are described by Sambrook, J., E. F. Fritsch, and T. Maniatis (*Molecular Cloning: A Laboratory Manual*, Cold Spring Harbor Laboratory Press, Cold Spring Harbor, N.Y., chapters 9 and 11, (1989)) and *Current Protocols in Molecular Biology* (F. M. Ausubel et al., eds., John Wiley & Sons, Inc., sections 2.10 and 6.3-6.4 (1995)), the relevant portions of which are incorporated by reference herein. Moderately stringent conditions for filter hybridizations include hybridization in about 50% formamide, 6×SSC at a temperature from about 42 C to 55 C and washing at about 60 C in 0.5×SSC, 0.1% SDS. Highly stringent conditions are defined as hybridization conditions as above, but with washing at approximately 68 C in 0.2×SSC, 0.1% SDS. SSPE (1×SSPE is 0.15 M NaCl, 10 mM NaH2P04, and 1.26 mM EDTA, pH 7.4) can be substituted for SSC (1×SSC is 0.15 M NaCl and 15 mM sodium citrate) in the hybridization and wash buffers; washes, optionally at least two washes, are performed for 15 minutes after hybridization is complete.

It should be understood that the wash temperature and wash salt concentration can be adjusted as necessary to achieve a desired degree of stringency by applying the basic principles that govern hybridization reactions and duplex stability, as known to those skilled in the art and described further below (see e.g., Sambrook et al., supra). When nucleic acids of known sequence are hybridized, the hybrid length can be determined by aligning the sequences of the nucleic acids (for example, using GAP) and identifying the region or regions of optimal sequence complementarity. The hybridization temperature for hybrids anticipated to be less than 50 base pairs in length should be 5 to 10° C. less than the melting temperature (Tm) of the hybrid, where Tm is determined according to the following equations. For hybrids less than 18 base pairs in length, Tm (degrees C.)=2(# of A+T bases)+4(# of G+C bases). For hybrids above 18 base pairs in length, Tm (degrees C.)=81.5+16.6 (log 10[Na+])+0.41 (% G+C)−(600 N), where N is the number of bases in the hybrid, and [Na+] is the concentration of sodium ions in the hybridization buffer. Each such hybridizing nucleic acid has a length that is at least 15 nucleotides (or at least 18 nucleotides, or at least 20, or at least 25, or at least 30, or at least 40, or at least 50, or at least 100. Sambrook et al., supra.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

As used herein, the verb "comprise" as is used in this description and in the claims and its conjugations are used in its non-limiting sense to mean that items following the word are included, but items not specifically mentioned are not excluded.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein are incorporated by reference in their entirety.

Polynucleotide Amplification and Determination

In many instances, it is desirable to amplify a nucleic acid sequence using any of several nucleic acid amplification procedures which are well known in the art. Specifically, nucleic acid amplification is the chemical or enzymatic synthesis of nucleic acid copies which contain a sequence that is complementary to a nucleic acid sequence being amplified (template). The methods and kits of the invention may use any nucleic acid amplification or detection methods known to one skilled in the art, such as those described in U.S. Pat. No. 5,525,462 (Takarada et al.); U.S. Pat. No. 6,114,117 (Hepp et al.); U.S. Pat. No. 6,127,120 (Graham et al.); U.S. Pat. No. 6,344,317 (Urnovitz); U.S. Pat. No. 6,448,001 (Oku); U.S. Pat. No. 6,528,632 (Catanzariti et al.); and PCT Pub. No. WO 2005/111209 (Nakajima et al.); all of which are incorporated herein by reference in their entirety.

Commonly used methods known in the art for the quantification of mRNA expression in a sample include northern blotting and in situ hybridization (Parker and Barnes, *Methods Mol. Biol.* 106:247-83, 1999), RNAse protection assays (Hod, *Biotechniques* 13:852-54, 1992), PCR-based methods, such as reverse transcription PCR (RT-PCR) (Weis et al., TIG 8:263-64, 1992), and array-based methods (Schena et al., *Science* 270:467-70, 1995). Alternatively, antibodies may be employed that can recognize specific duplexes, including DNA duplexes, RNA duplexes, and DNA-RNA hybrid duplexes, or DNA-protein duplexes. Representative methods for sequencing-based gene expression analysis include Serial Analysis of Gene Expression (SAGE), bead-based technologies, single molecule fluorescence in situ hybridization (smFISH) studies, and gene expression analysis by massively parallel signature sequencing. Velculescu et al. 1995 *Science* 270 484-487; Streefkerk et al., 1976, *Pro Biol Fluid Proc Coll* 24 811-814; Soini U.S. Pat. No. 5,028,545; smFISH, Lyubimova et al. 2013 *Nat Protocol* 8(9) 1743-1758.

In some embodiments, the nucleic acids are amplified by PCR amplification using methodologies known to one skilled in the art. One skilled in the art will recognize, however, that amplification can be accomplished by any known method, such as ligase chain reaction (LCR), QB-replicase amplification, rolling circle amplification, transcription amplification, self-sustained sequence replication, nucleic acid sequence-based amplification (NASBA), each of which provides sufficient amplification. Branched-DNA technology may also be used to qualitatively demonstrate the presence of a sequence of the technology, which represents a particular methylation pattern, or to quantitatively determine the amount of this particular genomic sequence in a sample. Nolte reviews branched-DNA signal amplification for direct quantitation of nucleic acid sequences in clinical samples (Nolte, 1998, Adv. Clin. Chem. 33:201-235).

The PCR process is well known in the art and is thus not described in detail herein. For a review of PCR methods and protocols, see, e.g., Innis et al., eds., *PCR Protocols, A Guide to Methods and Application*, Academic Press, Inc., San Diego, Calif. 1990; U.S. Pat. No. 4,683,202 (Mullis); which are incorporated herein by reference in their entirety. PCR reagents and protocols are also available from commercial vendors, such as Roche Molecular Systems (Pleasanton, Calif.). PCR may be carried out as an automated process with a thermostable enzyme. In this process, the temperature of the reaction mixture is cycled through a denaturing region, a primer annealing region, and an extension reaction region automatically. Machines specifically adapted for this purpose are commercially available.

High Throughput, Single Molecule Sequencing, and Direct Detection Technologies

Suitable next generation sequencing technologies are widely available. Examples include the 454 Life Sciences platform (Roche, Branford, Conn.) (Margulies et al. 2005 *Nature*, 437, 376-380); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al., 2006, *Genome Res*. 16, 383-393; U.S. Pat. Nos. 6,306,597 and 7,598,035 (Macevicz); U.S. Pat. No. 7,232,656 (Balasubramanian et al.)); or DNA Sequencing by Ligation, SOLiD System (Applied Biosystems/Life Technologies; U.S. Pat. Nos. 6,797,470, 7,083,917, 7,166,434, 7,320,865, 7,332,285, 7,364,858, and 7,429,453 (Barany et al.); or the Helicos True Single Molecule DNA sequencing technology (Harris et al., 2008 *Science*, 320, 106-109; U.S. Pat. Nos. 7,037,687 and 7,645,596 (Williams et al.); 7,169,560 (Lapidus et al.); 7,769,400 (Harris)), the single molecule, real-time (SMRT™) technology of Pacific Biosciences, and sequencing (Soni and Meller, 2007, *Clin. Chem.* 53, 1996-2001) which are incorporated herein by reference in their entirety. These systems allow the sequencing of many nucleic acid molecules isolated from a specimen at high orders of multiplexing in a parallel fashion (Dear, 2003, *Brief Funct. Genomic Proteomic,* 1(4), 397-416 and McCaughan and Dear, 2010, *J. Pathol.*, 220, 297-306). Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination. Machines for pyrosequencing and methylation specific reagents are available from Qiagen, Inc. (Valencia, Calif.). See also Tost and Gut, 2007, *Nat. Prot.* 2 2265-2275. An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., 2003, *J. Biotech.* 102, 117-124). Such a system can be used to exponentially amplify amplification products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing or detection, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each other for energy transfer to occur successfully. Bailey et al. recently reported a highly sensitive (15 pg methylated DNA) method using quantum dots to detect methylation status using fluorescence resonance energy transfer (MS-qFRET) (Bailey et al. 2009, *Genome Res.* 19(8), 1455-1461, which is incorporated herein by reference in its entirety).

An example of a system that can be used based on single-molecule sequencing generally involves hybridizing a primer to a study nucleic acid to generate a complex; associating the complex with a solid phase; iteratively extending the primer by a nucleotide tagged with a fluorescent molecule; and capturing an image of fluorescence resonance energy transfer signals after each iteration (e.g., Braslavsky et al., PNAS 100(7): 3960-3964 (2003); U.S. Pat. No. 7,297,518 (Quake et al.) which are incorporated herein by reference in their entirety). Such a system can be used to directly sequence amplification products generated by processes described herein. In some embodiments the released linear amplification product can be hybridized to a primer that contains sequences complementary to immobilized capture sequences present on a solid support, a bead or glass slide for example. Hybridization of the primer-released linear amplification product complexes with the immobilized capture sequences, immobilizes released linear amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer-released linear amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

The technology may be practiced with digital PCR. Digital PCR was developed by Kalinina and colleagues (Kalinina et al., 1997, *Nucleic Acids Res.* 25; 1999-2004) and further developed by Vogelstein and Kinzler (1999, *Proc. Natl. Acad. Sci. U.S.A.* 96; 9236-9241). The application of digital PCR is described by Cantor et al. (PCT Pub. Nos. WO 2005/023091A2 (Cantor et al.); WO 2007/092473 A2, (Quake et al.)), which are hereby incorporated by reference in their entirety. Digital PCR takes advantage of nucleic acid (DNA, cDNA or RNA) amplification on a single molecule level, and offers a highly sensitive method for quantifying low copy number nucleic acid. FLUIDIGM® Corporation, BioRad's Digital PCR and Raindance technologies all offer systems for the digital analysis of nucleic acids. See, Karlin-Neumann G et al. (2012). Probing copy number variations using Bio-Rad's QX100™ Droplet Digital™ PCR system. Bio-Rad Bulletin 6277; Diderot et al., *Clinical Chemistry* February 2013 clinchem.2012.193409.

In some embodiments, nucleotide sequencing may be by solid phase single nucleotide sequencing methods and processes. Solid phase single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in PCT Pub. No. WO 2009/091934 (Cantor).

In certain embodiments, nanopore sequencing detection methods include (a) contacting a nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (b) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected.

A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

Next generation sequencing techniques may be applied to measure expression levels or count numbers of transcripts using RNA-seq or whole transcriptome shotgun sequencing. See, e.g., Mortazavi et al. 2008 *Nat Meth* 5(7) 621-627 or Wang et al. 2009 *Nat Rev Genet* 10(1) 57-63.

Nucleic acids in the invention may be counted using methods known in the art. In one embodiment, NanoString's n Counter system may be used. Geiss et al. 2008 *Nat Biotech* 26(3) 317-325; U.S. Pat. No. 7,473,767 (Dimitrov). Alternatively, Fluidigm's Dynamic Array system may be used. Byrne et al. 2009 *PLoS ONE* 4 e7118; Helzer et al. 2009 *Can Res* 69 7860-7866. For reviews, see also Zhao et al. 2011 *Sci China Chem* 54(8) 1185-1201 and Ozsolak and Milos 2011 *Nat Rev Genet* 12 87-98.

The invention encompasses any method known in the art for enhancing the sensitivity of the detectable signal in such assays, including, but not limited to, the use of cyclic probe technology (Bakkaoui et al., 1996, *BioTechniques* 20: 240-8, which is incorporated herein by reference in its entirety); and the use of branched probes (Urdea et al., 1993, *Clin.*

Chem. 39, 725-6; which is incorporated herein by reference in its entirety). The hybridization complexes are detected according to well-known techniques in the art.

Reverse transcribed or amplified nucleic acids may be modified nucleic acids. Modified nucleic acids can include nucleotide analogs, and in certain embodiments include a detectable label and/or a capture agent. Examples of detectable labels include, without limitation, fluorophores, radioisotopes, colorimetric agents, light emitting agents, chemiluminescent agents, light scattering agents, enzymes and the like. Examples of capture agents include, without limitation, an agent from a binding pair selected from antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) pairs, and the like. Modified nucleic acids having a capture agent can be immobilized to a solid support in certain embodiments.

The invention described herein may be used in conjunction with other molecular techniques for detection of cancer such as US Pat Pub 2013/0171637 (Giafis et al.) the contents of which are hereby incorporated by reference in its entirety.

Statistical Methods

The data may be ranked for its ability to distinguish biomarkers in both the 1 versus all (i.e., disease versus normal) and the all-pairwise (i.e., normal versus specific disease) cases. One statistic used for the ranking is the area under the receiver operator characteristic (ROC) curve (a plot of sensitivity versus (1-specificity)). Although biomarkers are evaluated for reliability across datasets, the independent sample sets are not combined for the purposes of the ROC ranking. As a result, multiple independent analyses are performed and multiple independent rankings are obtained for each biomarker's ability to distinguish groups of interest.

It is to be understood that other genes and/or diagnostic criteria may be used in this invention. For example, animal characteristics, standard blood workups, the results of imaging tests, and/or histological evaluation may optionally be combined with biomarkers disclosed herein.

Such analysis methods may be used to form a predictive model, and then use that model to classify test data. For example, one convenient and particularly effective method of classification employs multivariate statistical analysis modeling, first to form a model (a "predictive mathematical model") using data ("modeling data") from samples of known class (e.g., from subjects known to have, or not have, a particular class, subclass or grade of lung cancer), and second to classify an unknown sample (e.g., "test data"), according to lung cancer status.

Pattern recognition (PR) methods have been used widely to characterize many different types of problems ranging for example over linguistics, fingerprinting, chemistry and psychology. In the context of the methods described herein, pattern recognition is the use of multivariate statistics, both parametric and non-parametric, to analyze spectroscopic data, and hence to classify samples and to predict the value of some dependent variable based on a range of observed measurements. There are two main approaches. One set of methods is termed "unsupervised" and these simply reduce data complexity in a rational way and also produce display plots that can be interpreted by the human eye. The other approach is termed "supervised" whereby a training set of samples with known class or outcome is used to produce a mathematical model and is then evaluated with independent validation data sets.

Unsupervised PR methods are used to analyze data without reference to any other independent knowledge. Examples of unsupervised pattern recognition methods include principal component analysis (PCA), hierarchical cluster analysis (HCA), and non-linear mapping (NLM).

Alternatively, and in order to develop automatic classification methods, it has proved efficient to use a "supervised" approach to data analysis. Here, a "training set" of biomarker expression data is used to construct a statistical model that predicts correctly the "class" of each sample. This training set is then tested with independent data (referred to as a test or validation set) to determine the robustness of the computer-based model. These models are sometimes termed "expert systems," but may be based on a range of different mathematical procedures. Supervised methods can use a data set with reduced dimensionality (for example, the first few principal components), but typically use unreduced data, with all dimensionality. In all cases the methods allow the quantitative description of the multivariate boundaries that characterize and separate each class, for example, each class of lung cancer in terms of its biomarker expression profile. It is also possible to obtain confidence limits on any predictions, for example, a level of probability to be placed on the goodness of fit (see, for example, Sharaf; Illman; Kowalski, eds. (1986). Chemometrics. New York: Wiley). The robustness of the predictive models can also be checked using cross-validation, by leaving out selected samples from the analysis.

Examples of supervised pattern recognition methods include the following nearest centroid methods (Dabney 2005 Bioinformatics 21(22):4148-4154 and Tibshirani et al. 2002 Proc. Natl. Acad. Sci. USA 99(10):6576-6572); soft independent modeling of class analysis (SIMCA) (see, for example, Wold, (1977) Chemometrics: theory and application 52: 243-282); partial least squares analysis (PLS) (see, for example, Wold (1966) Multivariate analysis 1: 391-420; Joreskog (1982) Causality, structure, prediction 1: 263-270); linear discriminant analysis (LDA) (see, for example, Nillson (1965). Learning machines. New York); K-nearest neighbor analysis (KNN) (see, for example, Brown and Martin 1996 J Chem Info Computer Sci 36(3):572-584); artificial neural networks (ANN) (see, for example, Wasserman (1993). Advanced methods in neural computing. John Wiley & Sons, Inc; O'Hare & Jennings (Eds.). (1996). Foundations of distributed artificial intelligence (Vol. 9). Wiley); probabilistic neural networks (PNNs) (see, for example, Bishop & Nasrabadi (2006). Pattern recognition and machine learning (Vol. 1, p. 740). New York: Springer; Specht, (1990). Probabilistic neural networks. Neural networks, 3(1), 109-118); rule induction (RI) (see, for example, Quinlan (1986) Machine learning, 1(1), 81-106); and, Bayesian methods (see, for example, Bretthorst (1990). An introduction to parameter estimation using Bayesian probability theory. In Maximum entropy and Bayesian methods (pp. 53-79). Springer Netherlands; Bretthorst, G. L. (1988). Bayesian spectrum analysis and parameter estimation (Vol. 48). New York: Springer-Verlag); unsupervised hierarchical clustering (see for example Herrero 2001 Bioinformatics 17(2) 126-136). In one embodiment, the classifier is the centroid based method described in Mullins et al. 2007 Clin Chem 53(7):1273-9, which is herein incorporated by reference in its entirety for its teachings regarding disease classification.

It is often useful to pre-process data, for example, by addressing missing data, translation, scaling, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data.

If possible, missing data, for example gaps in column values, should be avoided. However, if necessary, such missing data may be replaced or "filled" with, for example, the mean value of a column ("mean fill"); a random value ("random fill"); or a value based on a principal component analysis ("principal component fill"). Each of these different approaches will have a different effect on subsequent PR analysis.

"Translation" of the descriptor coordinate axes can be useful. Examples of such translation include normalization and mean centering. "Normalization" may be used to remove sample-to-sample variation. Many normalization approaches are possible, and they can often be applied at any of several points in the analysis. "Mean centering" may be used to simplify interpretation. Usually, for each descriptor, the average value of that descriptor for all samples is subtracted. In this way, the mean of a descriptor coincides with the origin, and all descriptors are "centered" at zero. In "unit variance scaling," data can be scaled to equal variance. Usually, the value of each descriptor is scaled by 1/StDev, where StDev is the standard deviation for that descriptor for all samples. "Pareto scaling" is, in some sense, intermediate between mean centering and unit variance scaling. In pareto scaling, the value of each descriptor is scaled by 1/sqrt (StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive skew and/or when data spans a large range, e.g., several orders of magnitude. Usually, for each descriptor, the value is replaced by the logarithm of that value. In "equal range scaling," each descriptor is divided by the range of that descriptor for all samples. In this way, all descriptors have the same range, that is, 1. However, this method is sensitive to presence of outlier points. In "autoscaling," each data vector is mean centered and unit variance scaled. This technique is a very useful because each descriptor is then weighted equally and large and small values are treated with equal emphasis. This can be important for analytes present at very low, but still detectable, levels.

Several supervised methods of scaling data are also known. Some of these can provide a measure of the ability of a parameter (e.g., a descriptor) to discriminate between classes, and can be used to improve classification by stretching a separation. For example, in "variance weighting," the variance weight of a single parameter (e.g., a descriptor) is calculated as the ratio of the inter-class variances to the sum of the intra-class variances. A large value means that this variable is discriminating between the classes. For example, if the samples are known to fall into two classes (e.g., a training set), it is possible to examine the mean and variance of each descriptor. If a descriptor has very different mean values and a small variance, then it will be good at separating the classes. "Feature weighting" is a more general description of variance weighting, where not only the mean and standard deviation of each descriptor is calculated, but other well-known weighting factors, such as the Fisher weight, are used.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

The process of comparing a measured value and a reference value can be carried out in any convenient manner appropriate to the type of measured value and reference value for the discriminative gene at issue. "Measuring" can be performed using quantitative or qualitative measurement techniques, and the mode of comparing a measured value and a reference value can vary depending on the measurement technology employed. For example, when a qualitative colorimetric assay is used to measure expression levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the invention will most commonly be quantitative values. In other examples, measured values are qualitative. As with qualitative measurements, the comparison can be made by inspecting the numerical data, or by inspecting representations of the data (e.g., inspecting graphical representations such as bar or line graphs).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a biomarker protein. Alternately, a separate device (e.g., a digital computer) may be used to compare the measured value(s) and the reference value(s). Automated devices for comparison may include stored reference values for the biomarker protein(s) being measured, or they may compare the measured value(s) with reference values that are derived from contemporaneously measured reference samples (e.g., samples from control subjects).

As will be apparent to those of skill in the art, when replicate measurements are taken, the measured value that is compared with the reference value is a value that takes into account the replicate measurements. The replicate measurements may be taken into account by using either the mean or median of the measured values as the "measured value."

The invention also includes methods of identifying animals for particular treatments or selecting animals for which a particular treatment would be desirable or contraindicated.

The methods above may be performed by a reference laboratory, a veterinary hospital pathology laboratory, a university veterinary laboratory, a veterinarian's office or a veterinarian. The methods above may further comprise an algorithm and/or statistical analysis.

Samples

The sample may be a biopsy specimen of the suspected mass. For detection of the copy number status by FISH, cells from the mass are used to provide templates for the FISH probes. For PCR and DNA sequence based assays, the required template DNA may be obtained from the cells of the suspected mass.

Compositions and Kits

The invention provides compositions and kits for detecting a mast cell tumor in a dog comprising: (a) at least one reagent selected from the group consisting of: a nucleic acid probe capable of specifically detecting target regions of CFA 5, CFA 20 or CFA 31; and (b) instructions for use in measuring a copy number of these region of CFA 5, CFA 20 or CFA 31 in a biological sample from a dog wherein if the copy number status of the regions of CFA 5, CFA 20 and/or CFA 31 differ from that of a normal control.

The instructions comprise determining in a sample of relevant cells obtained from the dog the presence of chromosomal abnormalities, wherein the presence of chromosomal abnormalities involving at least two of the probes indicates that the patient has mast cell tumor. Such kits may further comprise, or consist of, blocking agents or other probes, various labels or labeling agents to facilitate detection of the probes, reagents for hybridization (e.g., buffers), a metaphase spread, and the like.

The following Examples further illustrate the disclosure and are not intended to limit the scope. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

6. EXAMPLES

Materials and Methods

Tissue Specimens

The retrospective cohort study recruited 147 formalin fixed paraffin embedded (FFPE) tissue specimens of canine cutaneous MCTs that had been diagnosed between 2003 and 2012. Initial diagnosis for each case was based on histological evaluation of the FFPE specimen by a veterinary pathologist. To eliminate inter-observer variation in tumor grading, the H&E slides were re-evaluated for 3-tier and 2-tier tumor grading and mitotic index by a single board-certified veterinary pathologist. H&E-stained slides of each specimen were assessed used to identify and mark regions enriched for neoplastic regions, excluding any surrounding normal tissues. A series of 25-μm slices was then obtained from the corresponding FFPE tissue block, and regions of non-tumor tissues removed by macrodissection. Tumor DNA was isolated using a QIAamp FFPE DNA extraction kit (Qiagen, Valencia, Calif., USA). Spectrophotometry (NanoDrop, Thermo Scientific, Wilmington, Del.) and agarose gel electrophoresis were used to determine DNA quantity and integrity. Sample information is shown in Table 1.

KIT Gene Mutation Analysis

Activating KIT gene mutations are reported to be present in 10-30% of canine MCTs, with presence of a mutation being correlated with poor clinical outcomes (Gil da Costa, 2015). PCR amplification for exons 8, 9, and 11 of the canine KIT gene was performed using Taq RED Master Mix Kit (Genesee Scientific, San Diego, Calif., USA). Primers were designed using primer-BLAST software (www.ncbi.nlm.nih.gov/tools/primer-blast/) and are shown in Table 2. The presence of internal tandem repeat (ITD) mutation in exons 8 and 11 was visualized using agarose gel electrophoresis. When an ITD mutant band was present in the PCR products of exons 8 or 11, the band was excised and purified using QIAquick Gel Extraction Kit (QIAGEN), followed by DNA (Sanger) sequencing analysis. PCR products without evidence of ITD mutations were subjected to direct sequencing to detect other sequence changes of minor frequencies. All sequencing was performed at the North Carolina State University Genome Research Laboratory (research.ncsu.edu/gsl/). The sequencing data were analyzed using 4 peaks software (nucleobyte.com) and were compared with the canine KIT gene reference sequence (GeneID: AY313776).

Array Comparative Genomic Hybridization oaCGH analysis was performed on DNA samples from 109 primary tumors using Agilent SurePrint G3 Canine Genome 180K microarrays which contain 171,534 coding and noncoding 60-mer oligonucleotide sequences spaced at ~13 kb intervals (AMADID 25522, Agilent Technologies, Santa Clara, Calif., USA). A sex-matched equimolar pool of genomic DNA from peripheral blood of >100 healthy dogs was used as a common reference. Probe preparation, array hybridization, and post-hybridization washing were performed as reported previously (Thomas et al., 2014, Poorman et al., 2015, Roode et al., 2015, Shapiro et al., 2015). Scanned data were extracted using Feature Extraction Software v10.10 (Agilent Technologies) and assessed for data quality using Agilent QC metrics. Extracted data were filtered to exclude probes displaying non-uniform hybridization or signal saturation and imported into Nexus Copy Number software v7.5 (Biodiscovery Inc., El Sequendo, Calif., USA). Data was normalized using the FASST2 segmentation algorithm. Genomic copy number aberrations were defined as a minimum of three consecutive probes with log 2 tumor: reference values>0.201 (gain) or <−0.234 (loss). CNAs were defined as recurrent when CNAs were present in >20% of cases. The megabase (Mb) location of dog genes along the corresponding chromosome were based on the CanFam v3 genome sequence assembly accessed via the UCSC genome browser (genome.ucsc.edu/).

The Genomic Identification of Significant Targets in Cancer (GISTIC) algorithm was used to identify regions across the genome in tumors with and without KIT mutations with a statistically high frequency of aberration over the background (Q-bound<0.05, G score 2 1.0), indicating that these regions are more likely to contain a functional mutation associated with driving cancer pathogenesis (Beroukhim et al., 2007). Chromosomal regions were identified have having significantly different aberration frequencies between two groups when they had 2 50% difference between two groups also had a P<0.05 and Q-bound<0.05 based on a two-tailed Fisher's exact test.

Digital PCR Analysis

Four ddPCR assays, each comprising two PCR primers and a TAQMAN® probe, were designed within the genome sequences of high penetrance of copy number change at each of CFA 5:37 Mb, CFA 20:31 Mb, CFA 20:46 Mb and CFA 31:16 Mb. Primers and TAQMAN® probes were designed using PrimerQuest (www.idtdna.com) and PrimeBLAST (www.ncbi.nlm.nih.gov/tools/primer-blast/) software. For each assay, a double-Quenched probe (Integrated DNA Technologies, Coralville, Iowa) was used to reduce background fluorescence (5'-FAM/ZEN/3'-IBFQ probe for CFA 20:46 Mb and CFA 31: 16 Mb assays and HEX/ZEN/3'-IBFQ probe for CFA 5: 37 Mb and CFA 20: 31 Mb assays). Sequences and locations of primers and probes used in this study are shown in Table 2.

Two duplex ddPCR reactions were performed using a combination of CFA 20:46 Mb and CFA 20: 31 Mb (CFA20$^{46Mb/31Mb}$ assay), and CFA 31:16 Mb and CFA 5: 37 Mb (CFA 31/CFA 5 assay). Each reaction mixture comprised 1× Droplet Supermix (Bio-Rad), 500 nM of each primer, 250 nM of FAM- and HEX-labeled probes and ~55 ng of genomic DNA. The PCR reaction mixtures were partitioned into an emulsion of 20,000 droplets (mean SD: 17,572±2, 153 droplets/reaction) using a QX200™ Droplet Generator (Bio-Rad Laboratories, Richmond, Calif.). PCR was performed on T100™ Thermal Cycler (Bio-Rad) using thermal cycle condition as follows: denaturation at 95° C. for 10 min; 40 cycles of 94° C. for 30 sec and 58° C. for 60 sec; 98° C. for 10 min. Post PCR, droplets were analyzed on QX200™ Droplet Reader (Bio-Rad). The ratios of CFA 20: 46 Mb and CFA 20:31 Mb (CFA 20$^{46Mb/31Mb}$ ratio) and CFA 31:16 Mb and CFA 5: 37 Mb (CFA 31/CFA 5 ratio) were calculated on the Poisson distribution using Quantasoft™ software V1.7.4 (Bio-Rad). Comparison of copy number ratios determined by ddPCR and aCGH was performed as previously described (Mochizuki et al., 2015). To consolidate these two ratios into one parameter, score of CNAs associated with high-risk MCTs (CNA$^{MCT}$ score) was calculated and assessed to predict tumors with high-risk phenotypes using the following equation:

$$CNA^{MCT}\ score=CFA20^{46Mb/31Mb}\ ratio \times CFA\ 31/CFA\ 5\ ratio$$

Statistical Analysis

Association analysis was performed with Fisher's exact test or Pearson's chi-squared test to evaluate difference in frequencies between groups, and with Wilcoxon rank-sum test to compare continuous values between groups. The correlation of two values was evaluated with Pearson's correlation coefficient analysis. To determine the suitable threshold for discriminating high-risk MCTs from low-risk MCTs, a receiver operating characteristic (ROC) curve analysis was performed. Statistical analyses were performed using JMP software v1 (SAS Institute, Cary, N.C.). Significance was set at $P<0.05$.

Results

Pathological Findings

A total of 147 canine MCTs were included in the present study. Of these, genome-wide DNA copy number profiles were obtained for 109 tumors by oaCGH (oaCGH cohort). The remaining 38 tumors served as a validation cohort for ddPCR analysis. Tumors were graded by 3-tier histological grading (Grade 1: 18 tumors, Grade 2: 93 tumors and Grade 3: 36 tumors) and by 2-tier histological grading (low grade: 87 tumors and high grade: 60 tumors). There was no significant difference in histological grading between the oaCGH and validation cohorts.

Canine MCT Show Stepwise Accumulation of CNAs as Histological Grade Increases

The oaCGH analysis of DNA isolated from 109 canine MCT tumor specimens revealed that all MCT cases showed various numbers (16-575, median: 107) of CNAs throughout the genome. Whole chromosome and subchromosomal CNAs were detected in canine MCTs (CNA size: <26 kilobases (kb) to 117 megabases (Mb), median: 359 kb). Representative genome-wide DNA copy number profiles are shown in FIG. 1. Segregation of oaCGH data by 3-tier and 2-tier histological grading schemes revealed that higher-grade tumors had significantly more CNAs than low- or intermediate-grade counterparts in both numbers and altered length (FIG. 2). Penetrance plots demonstrated increased frequency of CNAs in a stepwise manner, as tumor histological grade increases (FIG. 3).

KIT Gene Mutation Status and its Association with CNAs in Canine MCTs

A KIT gene mutation was detected in 42 of 147 (29%) tumors, with increased frequency in high-grade tumors (in 3-tier grading system, 6%, 23% and 56% in grades 1, 2 and 3 tumors, respectively, $P<0.0001$; in 2-tier grading system, 13% and 52% in low-grade and high-grade tumors, respectively, $P<0.0001$). The six most common mutations detected were 1) an ITD mutation in exon 11, with or without involvement of intron 11 and exon 12 (hereafter called as exon 11 ITD mutations), accounting for 74% (31/42) of all KIT mutations, followed by 2) Exon 11 indel (9.5%), 3) Exon 8 ITD (4.8%), 4) Exon 9 S479 (4.8%), 5) Exon 9 N5081 (4.8%), and 6) Exon 8 Q430R (2.4%) mutations. Frequencies of the KIT mutation were not different in the aCGH and validation cohorts.

Segregation of oaCGH data by KIT mutational status demonstrated that tumors with KIT mutations exhibited significantly more CNAs, both in number and total length, than wild type (FIG. 4A). Genomic imbalance in 76 tumors with wild-type KIT gene (wt-KIT tumors) was limited to primarily small aberrations of low frequencies (FIG. 4B). The only recurrent CNAs>1 Mb were deletion of a mid-segment of CFA 20 (at 15-43 Mb) and/or gain of the distal portion of CFA 20 (at 45-50 Mb), detected in ~25% of wt-KIT tumors. Frequency of these CNAs significantly increased as histological grade increases, suggesting a possible association of this genomic aberration on CFA 20 with a malignant phenotype in wt-KIT tumors (FIG. 8).

Recurrent CNAs in KIT mutant tumors (mut-KIT tumors) include whole chromosome gain of CFA 4, 13, 31, 36 and 38 and loss of CFA 5, 16 and 28 as well as many subchromosomal changes (FIG. 4B). When mut-KIT tumors were further segregated by tumors with exon 11 ITD mutations (n=24) and those with other types of mutation (n=9), there was no significant difference in number, total length, and frequency of CNAs between two groups, resulting in similar penetrance plots (FIG. 9). Unlike wt-KIT tumors, further segregation of mut-KIT tumors by their histological grading did not show any CNAs that differed statistically in frequency between groups, partly due to their small sample sizes (FIG. 10). Therefore, mut-KIT tumors were treated as a single entity for further analysis, regardless of specific mutation type and histological grade.

Comparison analysis of CNAs detected in wt-KIT and mut-KIT tumors identified that deletion of CFA 5, including TP53 (CFA 5: 32.5 Mb, 2.6% vs 60.6%) and gain of CFA 31, including RUNX1 (CFA31: 30.3 Mb, 6.6% vs 63.6%), and a small number of subchromosomal regions on CFA36, occurred significantly more frequently in mut-KIT tumors, whereas there was no region occurring more frequently in wt-KIT tumors (Table 3).

These CNAs were further interrogated using GISTIC analysis to differentiate CNAs containing possible pathogenic genes from background random CNAs. GISTIC analysis identified 131 CNAs (72 gain and 59 loss) in wt-KIT tumors, including gain of regions containing TERT (CFA34: 11.3 Mb, G-score=10.20, Q-bound=3.28×10-10) and CDK4 (CFA10: 1.8 Mb, G-score=7.18, Q-bound=2.89×10-6). In mut-KIT tumors, GISTIC analysis identified 62 discrete CNAs (23 gain and 39 loss) including a copy number gain of CFA13: 47.0 Mb that flanks the KIT oncogene (CFA13: 47.1 Mb, G-score=7.64, Q-bound=2.01×10-5), as well as gains of other oncogenes such as RUNX (CFA31: 30.3 Mb, G-score=13.43, Q-bound=4.29×10-15) and MDM4 (CFA38: 1.0 Mb, G-score=6.60, Q-bound=4.64×10-4). Details of CNAs identified by GISTIC analysis are provided in Tables 4 and 5 for wt-KIT tumors and mut-KIT tumors, respectively.

CNAs Associated with High-Risk MCTs

From these data, we hypothesized that several CNAs may be used to segregate biologically aggressive MCTs from benign tumors. Due to the unavailability of clinical outcomes of the cohort, we used histological grading score and KIT mutational status to define "high-risk MCTs". As the 2-tier histological grading has been demonstrated to be superior in predicting clinical outcomes with higher interobserver consistency (Kiupel et al., 2011, Takeuchi et al., 2013, Sabattini et al., 2015), we only used the 2-tier grading system (low or high grade) hereafter. We defined tumors with high histological grade and/or KIT mutations as "high-risk MCT" and those with low histological grade without KIT mutations as "low-risk MCTs", based on the 2-tier histological grade and KIT mutational status. As mut-KIT tumors and high-grade wt-KIT tumors showed dissimilar copy number profiles, we sought regions where frequencies of CNAs are significantly higher in (1) mut-KIT tumors and (2) high-grade wt-KIT tumors, compared to low-grade wt-KIT tumors, to find genomic aberrations to separate high-risk and low-risk MCTs.

Comparison analysis revealed that genomic loss of CFA 5 and genomic gain of CFA 31 with a few subchromosomal CNAs occurred at significantly higher frequencies in mut-KIT tumors, compared to low-grade wt-KIT tumors (FIG. 6A). The comparison of high-grade and low-grade wt-KIT tumors revealed that only loss of middle portion of CFA 20 and gain of distal portion of CFA 20 were significantly different between two groups (FIG. 6B). Based on these findings, we then chose loss of CFA 5: 37.8 Mb and gain of CFA 31: 16.7 Mb as markers to differentiate mut-KIT tumors from low-risk MCTs and loss of CFA 20: 31.6 Mb and gain of CFA20: 46.4 Mb as markers to separate high-grade wt-KIT tumors from low-risk MCTs. Each case was then evaluated to have these alterations to predict high-risk MCTs. The presence of at least one of these four CNAs was able to predict high-risk MCTs with sensitivity of 91% and specificity of 89% in the cohort.

Digital PCR Analysis

Based on the aCGH data, two duplex ddPCR assays were designed to detect four CNAs associated with high-risk tumor phenotypes by calculating CFA $20^{46Mb/31Mb}$ ratio and CFA 31/CFA 5 ratio. The performance of the ddPCR assays was evaluated by comparing copy number ratios derived from oaCGH and ddPCR analyses. The results of two platforms were well correlated in 109 tumors with oaCGH profiles (R2=0.93 for CFA$20^{46Mb/31Mb}$ ratio and 0.78 for CFA 31/CFA 5 ratio, FIG. 7). High-risk tumors showed significant increase in the CNA$^{MCT}$ score as well as the CFA$20^{46Mb/31Mb}$ and CFA 31/CFA 5 ratios (all, P<0.0001, FIG. 7). ROC curve analysis was performed to evaluate CNA$^{MCT}$ score as an indicator for high-risk MCTs. The area under the ROC curve was 0.89. A cut-off CNA$^{MCT}$ score of 1.27 was determined at a point where the sum of sensitivity and specificity values was highest. At this cut-off point, the sensitivity and specificity of high-risk MCT detection in the oaCGH cohort were 76% (42/55) and 96% (52/54), respectively.

The CNA$^{MCT}$ score was then evaluated in a validation cohort consisting of 38 MCTs. The CNA$^{MCT}$ score showed significant increase in high-grade tumors (P=0.007, SUPPLEMENT FIG. 4) and was able to predict high-risk tumor phenotype with the sensitivity of 69% (11/16) and specificity of 86% (19/22) at the cut-off value of 1.27. Since there was no statistical difference in sensitivity and specificity between the oaCGH cohort and validation cohorts, these two cohorts were combined. Overall sensitivity and specificity of the CNA$^{MCT}$ score in 147 MCTs for the prediction of high-risk tumors were 75% and 93%, respectively. Four of five low-risk MCTs misclassified by the CNA$^{MCT}$ score were Patnaik's grade 2 tumors with mitotic index of 2-4, while remaining one was grade 1 tumor with mitotic index of 0. By evaluating a DNA samples from a canine MCT for the presence of a KIT exon 11 IDT and for the CNA$^{MCT}$ score, the combined sensitivity and specificity to predict a high-risk tumor phenotype is 89% and 93%, respectively.

Discussion

In this study, genome-wide DNA copy number analysis of 109 canine MCTs revealed the heterogeneous nature of genomic alteration in canine MCTs. Comparison of copy number profiles of tumors of different histological grades demonstrated a stepwise accumulation of copy number alterations as histological grade increases, suggesting that these genomic alterations contribute to the aggressive biological behavior.

The KIT signaling pathway plays a critical role in the survival and proliferation of mast cells (Roskoski, 2005). Activating mutations of the KIT gene results in constitutive activation of KIT protein without ligand binding, resulting in neoplastic transformation of mast cells. Indeed, more than 80% of human mast cell neoplasms harbor the KIT gene mutations (Haenisch et al., 2012), whereas the mutation is less frequent (20-30%) in canine MCTs (Letard et al., 2008, Takeuchi et al., 2013). In this study, distinct copy number profiles between MCTs with and without KIT mutations were demonstrated with extensive CNAs affecting multiple chromosomes in mut-KIT tumors. GISTIC analysis identified a significant peak of gain at KIT locus on CFA 13 as a potential region associated with driving cancer pathogenesis in mut-KIT MCTs. Although whole chromosomal gain of CFA 13 is the most common recurrent chromosomal abnormality across canine cancers (Thomas et al., 2009, Angstadt et al., 2011, Hedan et al., 2011, Thomas et al., 2011, Thomas et al., 2014, Poorman et al., 2015, Roode et al., 2015, Shapiro et al., 2015), the GISTIC analysis successfully identified the KIT locus in mut-KIT tumors by taking into account both frequency and magnitude of copy number change, proving the utility of this analysis to identify pathogenic region and potential somatic mutations in cancer (Beroukhim et al., 2007).

Loss of CFA 5 occurred in >50% of mut-KIT MCTs, but is a genomic alteration uncommon in other canine cancers. Among many tumor suppressor genes located on CFA 5, loss of TP53 may represent a key genetic event in the development and progression of mut-KIT MCTs. In addition to loss of TP53 detected in 57.6% of mut-KIT tumors, GISTIC analysis identified a significant peak of gain on CFA 38 encompassing MDM4, which is a family member of MDM2 and serves as a negative regulator of tumor suppressor p53. Frequent gains of MDM4 (48.5%) and MDM2 (9.1%), coupled with frequent loss of TP53, highlights that disruption of the p53 pathway may be a key molecular alteration in mut-KIT MCTs as 75.8% of this subtype harbored one or more these CNAs, while these CNAs were present in only 6.6% of wt-KIT tumors.

Similar to these CNAs that could lead to the p53 pathway deregulation, CNAs involving genes of the RB pathway, another major tumor suppressor pathway regulating cell cycle and replication, were also common in mut-KIT tumors. These CNAs include loss of CDKN2A/p6 (CFA 11: 41.2 Mb, 21.2% of mut-KIT tumors), loss of RB1 (CFA 22: 3.1 Mb, 18.2%), gain of CDK4 (CFA 10: 1.8 Mb, 15.2%), and gain of CDK6 (CFA 14: 18.3 Mb, 24.2%), leading to deregulation of the RB pathway in 48.5% of mut-KIT MCTs, whereas only 23.7% of wt-KIT tumors presented with these CNAs. A previous study also identified altered expressions of genes involved in the cell cycle and the p53 pathway in undifferentiated MCTs (Giantin et al., 2014), suggesting that frequent CNAs involved in these two major tumor suppressor pathways may change expression levels of these genes and result in the aggressive biological behavior of mut-KIT MCTs.

Compared to mut-KIT tumors, copy number changes of wt-KIT tumors were very limited, with the only recurrent chromosomal alterations>1 Mb being a ~30 Mb loss of CFA 20:15-43 Mb and a ~5 Mb gain of CFA 20: 45-50 Mb. Gain of the distal portion of CFA 20 has been detected previously in canine osteosarcoma, hemangiosarcoma, benign melanocytoma and acute leukemias (Angstadt et al., 2011, Thomas et al., 2014, Poorman et al., 2015, Roode et al., 2015), loss of mid-region of CFA 20 is uncommon in canine cancers, suggesting that this genomic alteration may play an important role in the development of MCTs in a KIT-independent manner.

Interestingly, a recent genome-wide association studies in golden retrievers identified SNPs located at CFA 20: 31 Mb-50 Mb (CanFam v3) that are associated with increased risk of developing MCTs (Arendt et al., 2015). A SNP in the GNAI2 gene (CFA20: 39,080,161), which introduce an alternative splice of this gene resulting in a truncated protein, shows a strong association with development of MCTs, along with other SNPs in this region encompassing hyaluronidase genes. These SNPs should be further examined to determine any associated with the development of MCTs and also with progression to a malignant tumor phenotype in the general dog population.

Along with mid-region of CFA 20, GISTIC analysis also identified significance of copy number gains of TERT (CFA34: 11.3 Mb, 36.8% of wt-KIT tumors) and CDK4 (CFA10: 1.8 Mb, 23.7%) in wt-KIT tumors. It is of note that frequencies of these CNAs increased in tumors of higher grade suggesting their potential roles in the tumor progression. This is of particular interest for discovery of therapeutic molecular targets for wt-KIT tumors, since KIT-target therapy is less effective in dogs with MCTs without KIT gene mutations compared to mut-KIT tumors (London et al., 2009, Hahn et al., 2010). Further studies will elucidate the molecular abnormalities crucial for the progression from benign MCTs to malignant tumors in a KIT-independent manner.

A major challenge in the clinical management of canine MCTs lies in accurate prognostication. The application of molecular profiling analysis may provide an objective means to predict clinical outcomes of this cancer. Molecular profiling using gene expression analysis has been shown to separate differentiated and undifferentiated MCTs and predict clinical outcomes by quantifying expression of 13 genes (Giantin et al., 2014). In this study, we were able to predict high-risk MCTs with a sensitivity of 91% and a specificity of 89% using just four CNAs on a genome-wide oaCGH platform. To reduce the cost and processing time, we developed a simple ddPCR assay to detect these four CNAs. The ddPCR test was able to predict high-risk tumor phenotypes with sensitivity of 75% and specificity of 93%, indicating its potential use for risk stratification of canine MCTs. Whereas specificity was comparable between the two platforms, the oaCGH showed superior sensitivity in detecting these CNAs. This is partly because the specimen used in this study was degraded FFPE tissue-derived DNA, which results in generation of single-stranded DNA and artificial copy number alterations (Bhat et al., 2010, Bhat et al., 2011). Although two platforms showed a good correlation in copy number assessment, it is pertinent that DNA degradation may lead to false-negative results in the ddPCR. Another possible advantage of genome-wide oaCGH is the simultaneous detection of less frequent CNAs in addition to the four CNAs examined by the ddPCR, which may help refine the detection algorithm. Although the ddPCR is a fast, cost-effective way of detecting high-risk tumor-associated CNAs, refinement of the assay may be necessary to improve sensitivity.

One major limitation of this study was lack of the clinical outcome of the cases, limiting the analysis of clinical relevance of these molecular alterations. Future studies using clinical specimens (e.g., cytological slides) in a cohort of dogs with MCTs, where clinical outcomes, including treatment and survival time are available, are necessary to evaluate the value of these CNAs as a prognostic indicator in a clinical setting.

In Table 6, the copy number variations (CNV) described herein were used to differentiate high-risk MCTs (Mut-KIT tumors and high-grade tumors) and low-risk MCTs (wild-type KIT, low-grade tumors) with the sensitivity of 91% and specificity of 89%.

In summary, we characterized CNAs of canine MCTs and identified different genomic imbalances between tumors of different histological grades and those of different KIT mutation status. Additional investigation will aid further clarification regarding genes within copy number aberrant regions that are important in the development and progression of canine MCTs. Four CNAs identified in this study may serve as an objective, rapid molecular assay for the identification of aggressive MCTs.

7. REFERENCES

ANGSTADT, A. Y., MOTSINGER-REIF, A., THOMAS, R., KISSEBERTH, W. C., GUILLERMO COUTO, C., DUVAL, D. L., NIELSEN, D. M., MODIANO, J. F. & BREEN, M. 2011. Characterization of canine osteosarcoma by array comparative genomic hybridization and RT-qPCR: signatures of genomic imbalance in canine osteosarcoma parallel the human counterpart. *Genes Chromosomes Cancer*, 50, 859-74.

ARENDT, M. L., MELIN, M., TONOMURA, N., KOLTOOKIAN, M., COURTAY-CAHEN, C., FLINDALL, N., BASS, J., BOERKAMP, K., MEGQUIR, K., YOUELL, L., MURPHY, S., MCCARTHY, C., LONDON, C., RUTTEMAN, G. R., STARKEY, M. & LINDBLAD-TOH, K. 2015. Genome-Wide Association Study of Golden Retrievers Identifies Germ-Line Risk Factors Predisposing to Mast Cell Tumours. *PLoS Genet*, 11, e1005647.

BEROUKHIM, et al. 2007. Assessing the significance of chromosomal aberrations in cancer: methodology and application to glioma. *Proc Natl Acad Sci USA,* 104, 20007-12.

BHAT, S., CURACH, N., MOSTYN, T., BAINS, G. S., GRIFFITHS, K. R. & EMSLIE, K. R. 2010. Comparison of methods for accurate quantification of DNA mass concentration with traceability to the international system of units. *Analytical chemistry,* 82, 7185-7192.

BHAT, S., MCLAUGHLIN, J. L. & EMSLIE, K. R. 2011. Effect of sustained elevated temperature prior to amplification on template copy number estimation using digital polymerase chain reaction. *Analyst,* 136, 724-732.

BREEN, M. 2009. Update on genomics in veterinary oncology. *Top Companion Anim Med,* 24, 113-21.

FINNIE, J. W. & BOSTOCK, D. E. 1979. Skin neoplasia in dogs. *Aust Vet J,* 55, 602-4.

FROHLING, S. & DOHNER, H. 2008. Chromosomal abnormalities in cancer. *N Engl J Med,* 359, 722-34.

GIANTIN, M., GRANATO, A., BARATTO, C., MARCONATO, L., VASCELLARI, M., MORELLO, E. M., VERCELLI, A., MUTINELLI, F. & DACASTO, M. 2014. Global gene expression analysis of canine cutaneous mast cell tumor: could molecular profiling be useful for subtype classification and prognostication? *PLoS One,* 9, e95481.

GIL DA COSTA, R. M. 2015. C-kit as a prognostic and therapeutic marker in canine cutaneous mast cell tumours: From laboratory to clinic. *Vet J,* 205, 5-10.

HAENISCH, B., NOTHEN, M. M. & MOLDERINGS, G. J. 2012. Systemic mast cell activation disease: the role of molecular genetic alterations in pathogenesis, heritability and diagnostics. *Immunology,* 137, 197-205.

HAHN, K. A., LEGENDRE, A. M., SHAW, N. G., PHILLIPS, B., OGILVIE, G. K., PRESCOTT, D. M., ATWATER, S. W., CARRERAS, J. K., LANA, S. E., LADUE, T., RUSK, A., KINET, J. P., DUBREUIL, P., MOUSSY, A. & HERMINE, O. 2010. Evaluation of 12- and 24-month survival rates after treatment with masitinib in dogs with nonresectable mast cell tumors. *Am J Vet Res,* 71, 1354-61.

HANAHAN, D. & WEINBERG, R. A. 2011. Hallmarks of cancer: the next generation. *Cell,* 144, 646-74.

HEDAN, B., THOMAS, R., MOTSINGER-REIF, A., ABADIE, J., ANDRE, C., CULLEN, J.& BREEN, M. 2011. Molecular cytogenetic characterization of canine histiocytic sarcoma: A spontaneous model for human histiocytic cancer identifies deletion of tumor suppressor genes and highlights influence of genetic background on tumor behavior. *BMC Cancer,* 11, 201.

KIUPEL, M., WEBSTER, J. D., BAILEY, K. L., BEST, S., DELAY, J., DETRISAC, C. J., FITZGERALD, S. D., GAMBLE, D., GINN, P. E., GOLDSCHMIDT, M. H., HENDRICK, M. J., HOWERTH, E. W., JANOVITZ, E. B., LANGOHR, I., LENZ, S. D., LIPSCOMB, T. P., MILLER, M. A., MISDORP, W., MOROFF, S., MULLANEY, T. P., NEYENS, I., O'TOOLE, D., RAMOSVARA, J., SCASE, T. J., SCHULMAN, F. Y., SLEDGE, D., SMEDLEY, R. C., SMITH, K., P, W. S., SOUTHORN, E., STEDMAN, N. L., STEFICEK, B. A., STROMBERG, P. C., VALLI, V. E., WEISBRODE, S. E., YAGER, J., HELLER, J. & MILLER, R. 2011. Proposal of a 2-tier histologic grading system for canine cutaneous mast cell tumors to more accurately predict biological behavior. *Vet Pathol,* 48, 147-55.

LETARD, S., YANG, Y., HANSSENS, K., PALMERINI, F., LEVENTHAL, P. S., GUERY, S., MOUSSY, A., KINET, J. P., HERMINE, O. & DUBREUIL, P. 2008. Gain-of-function mutations in the extracellular domain of KIT are common in canine mast cell tumors. *Mol Cancer Res,* 6, 1137-45.

LIN, T. Y., THOMAS, R., TSAI, P. C., BREEN, M. & LONDON, C. A. 2009. Generation and characterization of novel canine malignant mast cell line CL1. *Vet Immunol Immunopathol,* 127, 114-24.

LONDON, C. A., MALPAS, P. B., WOOD-FOLLIS, S. L., BOUCHER, J. F., RUSK, A. W., ROSENBERG, M. P., HENRY, C. J., MITCHENER, K. L., KLEIN, M. K. & HINTERMEISTER, J. G. 2009. Multi-center, placebo-controlled, double-blind, randomized study of oral toceranib phosphate (SU11654), a receptor tyrosine kinase inhibitor, for the treatment of dogs with recurrent (either local or distant) mast cell tumor following surgical excision. *Clinical Cancer Research,* 15, 3856-3865.

MITELMAN, F., JOHANSSON, B. & MERTENS, F. 2007. The impact of translocations and gene fusions on cancer causation. *Nat Rev Cancer,* 7, 233-45.

MOCHIZUKI, H., SHAPIRO, S. G. & BREEN, M. 2015. Detection of Copy Number Imbalance in Canine Urothelial Carcinoma With Droplet Digital Polymerase Chain Reaction. *Vet Pathol.* November 2015

PATNAIK, A. K., EHLER, W. J. & MACEWEN, E. G. 1984. Canine cutaneous mast cell tumor: morphologic grading and survival time in 83 dogs. *Vet Pathol,* 21, 469-74.

POORMAN, K., BORST, L., MOROFF, S., ROY, S., LABELLE, P., MOTSINGER-REIF, A. & BREEN, M. 2015. Comparative cytogenetic characterization of primary canine melanocytic lesions using array CGH and fluorescence in situ hybridization. *Chromosome Res,* 23, 171-86.

ROODE, S. C., ROTROFF, D., AVERY, A. C., SUTER, S. E., BIENZLE, D., SCHIFFMAN, J. D., MOTSINGER-REIF, A. & BREEN, M. 2015. Genome-wide assessment of recurrent genomic imbalances in canine leukemia identifies evolutionarily conserved regions for subtype differentiation. *Chromosome Res.*

ROSKOSKI, R., JR. 2005. Signaling by Kit protein-tyrosine kinase—the stem cell factor receptor. *Biochem Biophys Res Commun,* 337, 1-13.

ROTHWELL, T. L., HOWLETT, C. R., MIDDLETON, D. J., GRIFFITHS, D. A. & DUFF, B. C. 1987. Skin neoplasms of dogs in Sydney. *Aust Vet J,* 64, 161-4.

SABATTINI, S., SCARPA, F., BERLATO, D. & BETTINI, G. 2015. *Histologic grading of canine mast cell tumor: is 2 better than 3? Vet Pathol,* 52, 70-3.

SHAPIRO, S. G., RAGHUNATH, S., WILLIAMS, C., MOTSINGER-REIF, A. A., CULLEN, J. M., LIU, T., ALBERTSON, D., RUVOLO, M., BERGSTROM LUCAS, A., JIN, J., KNAPP, D. W., SCHIFFMAN, J. D. & BREEN, M. 2015. Canine urothelial carcinoma: genomically aberrant and comparatively relevant. *Chromosome Res,* 23, 311-31.

TAKEUCHI, Y., FUJINO, Y., WATANABE, M., TAKAHASHI, M., NAKAGAWA, T., TAKEUCHI, A., BONKOBARA, M., KOBAYASHI, T., OHNO, K. & UCHIDA, K. 2013. Validation of the prognostic value of histopathological grading or c-kit mutation in canine cutaneous mast cell tumours: a retrospective cohort study. *The Veterinary Journal,* 196, 492-498.

THOMAS, R., BORST, L., ROTROFF, D., MOTSINGER-REIF, A., LINDBLAD-TOH, K., MODIANO, J. F. & BREEN, M. 2014. Genomic profiling reveals extensive heterogeneity in somatic DNA copy number aberrations of canine hemangiosarcoma. *Chromosome Res*, 22, 305-19.

THOMAS, R., DUKE, S. E., WANG, H. J., BREEN, T. E., HIGGINS, R. J., LINDER, K. E., ELLIS, P., LANGFORD, C. F., DICKINSON, P. J., OLBY, N. J. & BREEN, M. 2009. 'Putting our heads together': insights into genomic conservation between human and canine intracranial tumors. *J Neurooncol*, 94, 333-49.

THOMAS, R., SEISER, E. L., MOTSINGER-REIF, A., BORST, L., VALLI, V. E., KELLEY, K., SUTER, S. E., ARGYLE, D., BURGESS, K., BELL, J., LINDBLAD-TOH, K., MODIANO, J. F. & BREEN, M. 2011. Refining tumor-associated aneuploidy through 'genomic recoding' of recurrent DNA copy number aberrations in 150 canine non-Hodgkin lymphomas. *Leuk Lymphoma*, 52, 1321-35.

VILLAMIL, J. A., HENRY, C. J., BRYAN, J. N., ELLERSIECK, M., SCHULTZ, L., TYLER, J. W. & HAHN, A. W. 2011. Identification of the most common cutaneous neoplasms in dogs and evaluation of breed and age distributions for selected neoplasms. *J Am Vet Med Assoc*, 239, 960-5.

TABLE 1

| Clinical and histopathologic findings in 109 canine mast cell tumors | |
|---|---|
| Breed | Labrador Retriever (34), Boxer (32), Pug (32), Golden Retriever (8), Mixed (6), other breeds (35, each <5) |
| Gender | Female (77), Male (70) |
| 3-tier histophatlogical | Grade 1 (18), Grade 2 (93), Grade 3 (36) |
| 2-tier histophatlogical | Low (87), High (62) |

TABLE 2

| Primer and probe sequences used in this study | | |
|---|---|---|
| Target | Forward (SEQ ID NOS: 1-7) | Reverse (SEQ ID NOS: 8-14) |
| KIT exon 8 | GGTGAGGTGTTCCAGCAGTC | CCTTCCCTCGTGCACATTA |
| KIT exon 9 | ACGTATGCCAATTCCAATGT | GCCATTGATGGAATGGACTT |
| KIT exon 11 | | GAAGCTAATGGGGTTCCCTAA |
| CFA 5: 37 Mb | AAAGATGATCTGTCTCTCTTTTCTCCTTGCCTAGAGTATGGCGAAG | GTCATGTGTTAGCAGAGAGAGA |
| CFA 20: 31 Mb | GGGTTACCCAAAGTAGTCTGA | TACTTTGTCTTCCTGGTTGTAACT |
| CFA 20: 46 Mb | AAGGTTCTTAGCACAGAGGAATC | AACATCCTATGCTCTGCTTCTG |
| CFA 31: 16 Mb | AGCTGGATTTACAAATAGCACTTTC | GGAAGAGAAGGCAATGAATAGGA |
| Target | Probe (SEQ ID NOS: 15-18) | Location |
| CFA 5: 37 Mb | TTGGCTGTTCTCTCTGTGTCCGTT | CFA 5: 37,905,014-37,905,113 |
| CFA 20: 31 Mb | TTTGGCTACCCTTCCTAAGACACAGC | CFA 20: 31,487,071-31,487,165 |
| CFA 20: 46 Mb | TTCTCTTCTCAGGCCGTTCCGTTT | CFA 20: 46,772,055-46,772,149 |
| CFA 31: 16 Mb | GTGAGATTTGCATTACATGACCCTGGA | CFA 31: 16,758,969-16,759,073 |

TABLE 3

| Genomic regions significantly different between mut-KIT tumors and wt-KIT tumors | | | | | | | | | |
|---|---|---|---|---|---|---|---|---|---|
| Region | Loc | Event | Length | Freq in mut-KIT (%) | Freq in wt-KIT (%) | Diff (%) | p-value | q-bound | Gene Symbols |
| chr5: 0-133,326 | q11 | Loss | 133,326 | 66.7 | 13.2 | 53.5 | 5.26E-08 | 5.71E-07 | cOR9R4, LOC102155730 |
| chr5: 133,326-381,054 | q11 | Loss | 247,728 | 60.6 | 0.0 | 60.6 | 1.59E-13 | 1.60E-11 | LOC102156207, LOC102155804 |
| chr5: 381,054-415,492 | q11 | Loss | 34,438 | 60.6 | 1.3 | 59.3 | 2.88E-12 | 1.11E-10 | |
| chr5: 415,492-431,007 | q11 | Loss | 15,515 | 66.7 | 5.3 | 58.4 | 1.67E-10 | 2.84E-09 | |
| chr5: 431,007-481,597 | q11 | Loss | 50,590 | 66.7 | 7.9 | 58.8 | 5.39E-10 | 8.10E-09 | |
| chr5: 481,597-571,794 | q11 | Loss | 90,197 | 69.7 | 7.9 | 61.8 | 9.19E-11 | 1.85E-09 | LOC102156249, LOC102156294 |
| chr5: 571,794-589,240 | q11 | Loss | 17,446 | 69.7 | 9.2 | 60.5 | 3.47E-10 | 5.61E-09 | |
| chr5: 589,240-599,748 | q11 | Loss | 10,508 | 69.7 | 10.5 | 59.2 | 1.18E-09 | 1.59E-08 | |
| chr5: 599,748-626,252 | q11 | Loss | 26,504 | 63.6 | 10.5 | 53.1 | 3.13E-08 | 3.41E-07 | |
| chr5: 626,252-650,764 | q11 | Loss | 24,512 | 63.6 | 13.2 | 50.5 | 2.37E-07 | 2.43E-06 | |
| chr5: 650,764-749,787 | q11 | Loss | 99,023 | 66.7 | 14.5 | 52.2 | 1.36E-07 | 1.40E-06 | LOC100687391, LOC102155966, B3GAT1 |
| chr5: 754,021-761,056 | q11 | Loss | 7,035 | 63.6 | 7.9 | 55.7 | 2.91E-09 | 3.74E-08 | GLB1L2 |
| chr5: 761,056-769,157 | q11 | Loss | 8,101 | 63.6 | 0.0 | 63.6 | 2.33E-14 | 6.04E-12 | GLB1L2 |
| chr5: 769,157-774,383 | q11 | Loss | 5,226 | 60.6 | 0.0 | 60.6 | 1.59E-13 | 1.60E-11 | GLB1L2 |
| chr5: 774,383-880,302 | q11 | Loss | 105,919 | 63.6 | 0.0 | 63.6 | 2.33E-14 | 6.04E-12 | GLB1L2, GLB1L3, LOC102156417, LOC607396 |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| chr5: 880,302-1,142,528 | q11 | Loss | 262,226 | 60.6 | 0.0 | 60.6 | 1.59E-13 | 1.60E-11 | LOC102156417, LOC607396, LOC102156118, ACAD8, THYN1, VPS26B, NCAPD3, JAM3 |
| chr5: 1,142,528-1,153,946 | q11 | Loss | 11,418 | 60.6 | 1.3 | 59.3 | 2.88E-12 | 1.11E-10 | JAM3 |
| chr5: 1,153,946-1,167,298 | q11 | Loss | 13,352 | 60.6 | 2.6 | 58.0 | 2.72E-11 | 6.21E-10 | JAM3 |
| chr5: 1,167,298-1,182,071 | q11 | Loss | 14,773 | 57.6 | 2.6 | 54.9 | 1.56E-10 | 2.67E-09 | |
| chr5: 1,182,071-1,211,221 | q11 | Loss | 29,150 | 60.6 | 6.6 | 54.0 | 3.94E-09 | 4.98E-08 | |
| chr5: 1,211,221-1,224,769 | q11 | Loss | 13,548 | 60.6 | 7.9 | 52.7 | 1.46E-08 | 1.64E-07 | |
| chr5: 1,224,769-1,333,535 | q11 | Loss | 108,766 | 60.6 | 10.5 | 50.1 | 1.42E-07 | 1.46E-06 | IGSF9B |
| chr5: 1,333,535-1,360,338 | q11 | Loss | 26,803 | 60.6 | 7.9 | 52.7 | 1.46E-08 | 1.64E-07 | SPATA19 |
| chr5: 1,360,338-1,404,082 | q11 | Loss | 43,744 | 60.6 | 1.3 | 59.3 | 2.88E-12 | 1.11E-10 | SPATA19 |
| chr5: 1,404,082-1,491,974 | q11 | Loss | 87,892 | 57.6 | 1.3 | 56.3 | 1.75E-11 | 4.38E-10 | |
| chr5: 1,491,974-1,776,954 | q11 | Loss | 284,980 | 57.6 | 0.0 | 57.6 | 1.02E-12 | 5.07E-11 | |
| chr5: 1,776,954-1,922,199 | q11 | Loss | 145,245 | 57.6 | 1.3 | 56.3 | 1.75E-11 | 4.38E-10 | |
| chr5: 1,922,199-2,400,485 | q11 | Loss | 478,286 | 57.6 | 0.0 | 57.6 | 1.02E-12 | 5.07E-11 | OPCML |
| chr5: 2,400,485-2,584,033 | q11 | Loss | 183,548 | 54.5 | 0.0 | 54.5 | 6.22E-12 | 1.92E-10 | OPCML |
| chr5: 2,584,033-2,704,511 | q11 | Loss | 120,478 | 57.6 | 0.0 | 57.6 | 1.02E-12 | 5.07E-11 | OPCML |
| chr5: 2,704,511-3,349,181 | q11 | Loss | 644,670 | 54.5 | 0.0 | 54.5 | 6.22E-12 | 1.92E-10 | NTM |
| chr5: 3,349,181-3,399,027 | q11 | Loss | 49,846 | 57.6 | 0.0 | 57.6 | 1.02E-12 | 5.07E-11 | NTM |
| chr5: 3,399,027-3,433,371 | q11 | Loss | 34,344 | 63.6 | 1.3 | 62.3 | 4.46E-13 | 3.02E-11 | NTM |
| chr5: 3,433,371-3,464,227 | q11 | Loss | 30,856 | 63.6 | 2.6 | 61.0 | 4.45E-12 | 1.48E-10 | NTM |
| chr5: 3,464,227-3,499,187 | q11 | Loss | 34,960 | 69.7 | 5.3 | 64.4 | 4.36E-12 | 1.48E-10 | NTM |
| chr5: 3,499,187-3,576,535 | q11 | Loss | 77,348 | 72.7 | 5.3 | 67.5 | 6.18E-13 | 3.91E-11 | NTM |
| chr5: 3,576,535-3,690,776 | q11 | Loss | 114,241 | 69.7 | 5.3 | 64.4 | 4.36E-12 | 1.48E-10 | NTM, LOC102154392, LOC102154472 |
| chr5: 3,690,776-3,710,651 | q11 | Loss | 19,875 | 69.7 | 2.6 | 67.1 | 9.50E-14 | 1.12E-11 | |
| chr5: 3,710,651-3,753,162 | q11 | Loss | 42,511 | 69.7 | 1.3 | 68.4 | 8.56E-15 | 3.54E-12 | |
| chr5: 3,753,162-3,807,807 | q11 | Loss | 54,645 | 66.7 | 0.0 | 66.7 | 3.18E-15 | 3.41E-12 | |
| chr5: 3,807,807-4,031,844 | q11-q12 | Loss | 224,037 | 57.6 | 0.0 | 57.6 | 1.02E-12 | 5.07E-11 | NCAPD3 |
| chr5: 4,031,844-4,721,545 | q12 | Loss | 689,701 | 54.5 | 0.0 | 54.5 | 6.22E-12 | 1.92E-10 | NCAPD3, SNX19, LOC102151125, ADAMTS15, ADAMTS8, ZBTB44, ST14, APLP2 |
| chr5: 4,721,545-5,115,444 | q12 | Loss | 393,899 | 57.6 | 0.0 | 57.6 | 1.02E-12 | 5.07E-11 | APLP2, LOC102154549, PRDM10, NFRKB, TMEM45B |
| chr5: 5,115,444-5,377,336 | q12 | Loss | 261,892 | 60.6 | 0.0 | 60.6 | 1.59E-13 | 1.60E-11 | BARX2, LOC102152251, LOC102156865 |
| chr5: 5,377,336-5,667,233 | q12 | Loss | 289,897 | 57.6 | 0.0 | 57.6 | 1.02E-12 | 5.07E-11 | LOC102156865, ARHGAP32 |
| chr5: 5,667,233-5,821,501 | q12 | Loss | 154,268 | 60.6 | 0.0 | 60.6 | 1.59E-13 | 1.60E-11 | ARHGAP32, KCNJ5, KCNJ1 |
| chr5: 5,821,501-5,854,005 | q12 | Loss | 32,504 | 57.6 | 0.0 | 57.6 | 1.02E-12 | 5.07E-11 | FLI1 |
| chr5: 5,854,005-5,867,075 | q12 | Loss | 13,070 | 54.5 | 0.0 | 54.5 | 6.22E-12 | 1.92E-10 | FLI1 |
| chr5: 5,867,075-5,926,290 | q12 | Loss | 59,215 | 51.5 | 0.0 | 51.5 | 3.58E-11 | 7.73E-10 | FLI1 |
| chr5: 6,218,480-6,467,492 | q12 | Loss | 249,012 | 54.5 | 0.0 | 54.5 | 6.22E-12 | 1.92E-10 | LOC102153240 |
| chr5: 6,467,492-6,667,635 | q12 | Loss | 200,143 | 57.6 | 0.0 | 57.6 | 1.02E-12 | 5.07E-11 | |
| chr5: 6,667,635-6,817,010 | q12 | Loss | 149,375 | 54.5 | 0.0 | 54.5 | 6.22E-12 | 1.92E-10 | |
| chr5: 6,817,010-6,908,015 | q12 | Loss | 91,005 | 57.6 | 0.0 | 57.6 | 1.02E-12 | 5.07E-11 | |
| chr5: 6,908,015-7,040,574 | q12 | Loss | 132,559 | 54.5 | 0.0 | 54.5 | 6.22E-12 | 1.92E-10 | |
| chr5: 7,040,574-7,122,705 | q12 | Loss | 82,131 | 51.5 | 0.0 | 51.5 | 3.58E-11 | 7.73E-10 | |
| chr5: 7,440,761-7,479,883 | q12 | Loss | 39,122 | 51.5 | 0.0 | 51.5 | 3.58E-11 | 7.73E-10 | |
| chr5: 7,479,883-7,489,731 | q12 | Loss | 9,848 | 57.6 | 0.0 | 57.6 | 1.02E-12 | 5.07E-11 | |
| chr5: 7,489,731-7,693,556 | q12 | Loss | 203,825 | 60.6 | 1.3 | 59.3 | 2.88E-12 | 1.11E-10 | KIRREL3 |
| chr5: 7,693,556-7,918,502 | q12 | Loss | 224,946 | 57.6 | 1.3 | 56.3 | 1.75E-11 | 4.38E-10 | KIRREL3 |
| chr5: 7,918,502-7,937,124 | q12 | Loss | 18,622 | 57.6 | 3.9 | 53.6 | 9.72E-10 | 1.34E-08 | KIRREL3 |
| chr5: 7,937,124-7,968,162 | q12 | Loss | 31,038 | 60.6 | 3.9 | 56.7 | 1.79E-10 | 2.97E-09 | KIRREL3 |
| chr5: 7,968,162-8,094,810 | q12 | Loss | 126,648 | 60.6 | 7.9 | 52.7 | 1.46E-08 | 1.64E-07 | KIRREL3 |
| chr5: 8,113,294-8,135,481 | q12 | Loss | 22,187 | 57.6 | 2.6 | 54.9 | 1.56E-10 | 2.67E-09 | KIRREL3, ST3GAL4 |
| chr5: 8,135,481-8,151,341 | q12 | Loss | 15,860 | 57.6 | 0.0 | 57.6 | 1.02E-12 | 5.07E-11 | ST3GAL4 |
| chr5: 8,592,141-8,608,158 | q12 | Loss | 16,017 | 54.5 | 0.0 | 54.5 | 6.22E-12 | 1.92E-10 | PUS3, HYLS1 |
| chr5: 8,608,158-9,046,592 | q12 | Loss | 438,434 | 60.6 | 0.0 | 60.6 | 1.59E-13 | 1.60E-11 | PATE2, PATE1, ACRV1, CHEK1, STT3A, EI24, FEZ1 |
| chr5: 9,046,592-9,062,538 | q12 | Loss | 15,946 | 57.6 | 0.0 | 57.6 | 1.02E-12 | 5.07E-11 | PKNOX2 |
| chr5: 9,062,538-9,218,872 | q12 | Loss | 156,334 | 60.6 | 0.0 | 60.6 | 1.59E-13 | 1.60E-11 | PKNOX2, LOC102156272 |
| chr5: 9,218,872-9,395,688 | q12 | Loss | 176,816 | 57.6 | 0.0 | 57.6 | 1.02E-12 | 5.07E-11 | PKN0X2, LOC102156272, TMEM218, SLC37A2 |
| chr5: 9,395,688-9,670,771 | q12 | Loss | 275,083 | 54.5 | 0.0 | 54.5 | 6.22E-12 | 1.92E-10 | SLC37A2, CCDC15, HEPACAM, HEPN1, ROBO4, ROBO3, MSANTD2, ESAM, VSIG2 |
| chr5: 9,670,771-9,837,421 | q12 | Loss | 166,650 | 66.7 | 0.0 | 66.7 | 3.18E-15 | 3.41E-12 | VSIG2, NRGN, SPA17, SIAE, TBRG1, PANX3, OR8A1 |
| chr5: 9,837,421-10,291,526 | q12 | Loss | 454,105 | 63.6 | 0.0 | 63.6 | 2.33E-14 | 6.04E-12 | LOC489314, LOC489315, LOC100686868, LOC489317, OR8B4, cOR8C4, |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| | | | | | | | | | LOC100687027, LOC609966, cOR8B15, LOC100686309, LOC100686560, LOC100687264, LOC100687028, LOC489325, LOC100687427, LOC489326, OR8D2, LOC100687661, LOC102151657 |
| chr5: 10,291,526-10,518,964 | q12 | Loss | 227,438 | 60.6 | 0.0 | 60.6 | 1.59E−13 | 1.60E−11 | OR28D07, OR16A12, OR08E10, VWA5A, LOC100688048, LOC100688253, cOR10D5P, LOC489338, LOC489340, LOC489341, cOR10G11, OR10S1 |
| chr5: 10,518,964-10,717,556 | q12 | Loss | 198,592 | 60.6 | 1.3 | 59.3 | 2.88E−12 | 1.11E−10 | cOR8C5, OR4D5, TMEM225, LOC100688741, LOC489347, cOR6M4, cOR6M5, OR6M1, OR6X1, ZNF202 |
| chr5: 10,717,556-10,824,977 | q12 | Loss | 107,421 | 66.7 | 1.3 | 65.4 | 6.42E−14 | 9.66E−12 | ZNF202, LOC102155174, SCN3B, GRAMD1B |
| chr5: 10,824,977-10,867,242 | q12 | Loss | 42,265 | 69.7 | 1.3 | 68.4 | 8.56E−15 | 3.54E−12 | GRAMD1B |
| chr5: 10,867,242-10,929,698 | q12 | Loss | 62,456 | 63.6 | 1.3 | 62.3 | 4.46E−13 | 3.02E−11 | GRAMD1B |
| chr5: 10,929,698-11,178,647 | q12 | Loss | 248,949 | 57.6 | 1.3 | 56.3 | 1.75E−11 | 4.38E−10 | GRAMD1B, LOC609517 |
| chr5: 11,178,647-11,307,095 | q12-q13 | Loss | 128,448 | 60.6 | 1.3 | 59.3 | 2.88E−12 | 1.11E−10 | FOXRED1, CLMP, HSPA8 |
| chr5: 11,307,095-11,365,230 | q13 | Loss | 58,135 | 63.6 | 1.3 | 62.3 | 4.46E−13 | 3.02E−11 | |
| chr5: 11,365,230-11,372,266 | q13 | Loss | 7,036 | 57.6 | 1.3 | 56.3 | 1.75E−11 | 4.38E−10 | BSX |
| chr5: 11,372,266-11,378,881 | q13 | Loss | 6,615 | 54.5 | 1.3 | 53.2 | 9.97E−11 | 1.85E−09 | |
| chr5: 11,378,881-11,425,343 | q13 | Loss | 46,462 | 54.5 | 2.6 | 51.9 | 8.40E−10 | 1.18E−08 | C5H11orf63 |
| chr5: 11,616,512-11,647,820 | q13 | Loss | 31,308 | 54.5 | 2.6 | 51.9 | 8.40E−10 | 1.18E−08 | |
| chr5: 11,647,820-11,670,962 | q13 | Loss | 23,142 | 57.6 | 2.6 | 54.9 | 1.56E−10 | 2.67E−09 | |
| chr5: 11,670,962-11,842,755 | q13 | Loss | 171,793 | 60.6 | 2.6 | 58.0 | 2.72E−11 | 6.21E−10 | |
| chr5: 11,842,755-11,941,764 | q13 | Loss | 99,009 | 63.6 | 2.6 | 61.0 | 4.45E−12 | 1.48E−10 | LOC100682870 |
| chr5: 11,941,764-12,064,197 | q13 | Loss | 122,433 | 60.6 | 2.6 | 58.0 | 2.72E−11 | 6.21E−10 | LOC100682870 |
| chr5: 12,064,197-12,133,064 | q13 | Loss | 68,867 | 63.6 | 2.6 | 61.0 | 4.45E−12 | 1.48E−10 | BLID, LOC102156815 |
| chr5: 12,133,064-12,216,348 | q13 | Loss | 83,284 | 66.7 | 3.9 | 62.7 | 4.94E−12 | 1.59E−10 | LOC102156815 |
| chr5: 12,216,348-12,272,269 | q13 | Loss | 55,921 | 63.6 | 3.9 | 59.7 | 3.09E−11 | 6.77E−10 | |
| chr5: 12,272,269-12,353,441 | q13 | Loss | 81,172 | 66.7 | 3.9 | 62.7 | 4.94E−12 | 1.59E−10 | |
| chr5: 12,353,441-12,383,117 | q13 | Loss | 29,676 | 69.7 | 3.9 | 65.7 | 7.29E−13 | 4.00E−11 | |
| chr5: 12,383,117-12,432,341 | q13 | Loss | 49,224 | 60.6 | 3.9 | 56.7 | 1.79E−10 | 2.97E−09 | |
| chr5: 12,432,341-12,543,948 | q13 | Loss | 111,607 | 57.6 | 2.6 | 54.9 | 1.56E−10 | 2.67E−09 | SORL1 |
| chr5: 12,543,948-12,959,155 | q13 | Loss | 415,207 | 60.6 | 2.6 | 58.0 | 2.72E−11 | 6.21E−10 | SORL1, SC5D, LOC102157382, LOC489316, TECTA |
| chr5: 12,959,155-13,022,344 | q13 | Loss | 63,189 | 66.7 | 2.6 | 64.0 | 6.76E−13 | 3.91E−11 | cOR8B3, TBCEL |
| chr5: 13,022,344-13,134,971 | q13 | Loss | 112,627 | 63.6 | 2.6 | 61.0 | 4.45E−12 | 1.48E−10 | TBCEL, cOR8B1P, GRIK4 |
| chr5: 13,134,971-13,672,471 | q13 | Loss | 537,500 | 66.7 | 2.6 | 64.0 | 6.76E−13 | 3.91E−11 | cOR8D5, GRIK4, OR08H04, LOC607862, ARHGEF12 |
| chr5: 13,672,471-13,833,005 | q13 | Loss | 160,534 | 66.7 | 1.3 | 65.4 | 6.42E−14 | 9.66E−12 | TMEM136, POU2F3, OAF, LOC100683683 |
| chr5: 13,833,005-14,058,393 | q13 | Loss | 225,388 | 63.6 | 1.3 | 62.3 | 4.46E−13 | 3.02E−11 | TRIM29 |
| chr5: 14,058,393-14,123,666 | q13 | Loss | 65,273 | 63.6 | 2.6 | 61.0 | 4.45E−12 | 1.48E−10 | |
| chr5: 14,123,666-14,157,781 | q13 | Loss | 34,115 | 63.6 | 3.9 | 59.7 | 3.09E−11 | 6.77E−10 | |
| chr5: 14,157,781-14,194,514 | q13 | Loss | 36,733 | 63.6 | 5.3 | 58.4 | 1.67E−10 | 2.84E−09 | |
| chr5: 14,194,514-14,268,931 | q13 | Loss | 74,417 | 66.7 | 6.6 | 60.1 | 1.33E−10 | 2.43E−09 | PVRL1 |
| chr5: 14,268,931-14,301,979 | q13 | Loss | 33,048 | 69.7 | 6.6 | 63.1 | 2.16E−11 | 5.35E−10 | PVRL1 |
| chr5: 14,301,979-14,350,047 | q13 | Loss | 48,068 | 69.7 | 7.9 | 61.8 | 9.19E−11 | 1.85E−09 | |
| chr5: 14,350,047-14,434,923 | q13 | Loss | 84,876 | 69.7 | 6.6 | 63.1 | 2.16E−11 | 5.35E−10 | LOC102152657 |
| chr5: 14,434,923-14,497,888 | q13 | Loss | 62,965 | 63.6 | 2.6 | 61.0 | 4.45E−12 | 1.48E−10 | LOC102152657 |
| chr5: 14,497,888-14,560,969 | q13 | Loss | 63,081 | 60.6 | 2.6 | 58.0 | 2.72E−11 | 6.21E−10 | LOC102152657, THY1, LOC102152850, USP2, MFRP |
| chr5: 14,691,773-14,813,785 | q13 | Loss | 122,012 | 54.5 | 2.6 | 51.9 | 8.40E−10 | 1.18E−08 | PDZD3, NLRX1, ABCG4, HINFP, C2CD2L, DPAGT1, LOC489372, HMBS, VPS11, LOC102154262, HYOU1 |
| chr5: 14,813,785-15,004,440 | q13 | Loss | 190,655 | 57.6 | 2.6 | 54.9 | 1.56E−10 | 2.67E−09 | LOC102152874, SLC37A4, TRAPPC4, RPS25, CCDC84, FOXR1, UPK2, BCL9L, CXCR5, DDX6 |
| chr5: 15,004,440-15,224,520 | q13 | Loss | 220,080 | 60.6 | 2.6 | 58.0 | 2.72E−11 | 6.21E−10 | DDX6, LOC102155606, LOC102155677, TREH, PHLDB1, ARCN1, IFT46, TMEM25, TTC36, KMT2A |
| chr5: 15,517,999-15,590,459 | q13 | Loss | 72,460 | 75.8 | 5.3 | 70.5 | 7.94E−14 | 1.12E−11 | SCN2B, SCN4B, TMPRSS4 |
| chr5: 15,590,459-15,629,393 | q13-q14.1 | Loss | 38,934 | 69.7 | 5.3 | 64.4 | 4.36E−12 | 1.48E−10 | TMPRSS4 |
| chr5: 15,629,393-15,725,600 | q14.1 | Loss | 96,207 | 72.7 | 5.3 | 67.5 | 6.18E−13 | 3.91E−11 | IL10RA |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| chr5: 15,725,600-15,902,742 | q14.1 | Loss | 177,142 | 72.7 | 7.9 | 64.8 | 1.43E−11 | 4.38E−10 | TMPRSS13, FXYD6, FXYD2, DSCAML1 |
| chr5: 15,902,742-15,949,009 | q14.1 | Loss | 46,267 | 72.7 | 10.5 | 62.2 | 2.01E−10 | 3.28E−09 | DSCAML1 |
| chr5: 15,949,009-16,029,118 | q14.1 | Loss | 80,109 | 72.7 | 11.8 | 60.9 | 6.54E−10 | 9.79E−09 | DSCAML1 |
| chr5: 16,029,118-16,062,976 | q14.1 | Loss | 33,858 | 69.7 | 11.8 | 57.9 | 3.69E−09 | 4.71E−08 | DSCAML1 |
| chr5: 16,062,976-16,105,095 | q14.1 | Loss | 42,119 | 69.7 | 10.5 | 59.2 | 1.18E−09 | 1.59E−08 | DSCAML1 |
| chr5: 16,105,095-16,139,973 | q14.1 | Loss | 34,878 | 66.7 | 6.6 | 60.1 | 1.33E−10 | 2.43E−09 | DSCAML1 |
| chr5: 16,139,973-16,160,653 | q14.1 | Loss | 20,680 | 54.5 | 2.6 | 51.9 | 8.40E−10 | 1.18E−08 | DSCAML1 |
| chr5: 16,384,444-16,411,973 | q14.1 | Loss | 27,529 | 54.5 | 2.6 | 51.9 | 8.40E−10 | 1.18E−08 | PCSK7, TAGLN, SIDT2 |
| chr5: 16,452,934-16,698,305 | q14.1 | Loss | 245,371 | 54.5 | 2.6 | 51.9 | 8.40E−10 | 1.18E−08 | SIK3 |
| chr5: 16,698,305-16,809,673 | q14.1 | Loss | 111,368 | 57.6 | 2.6 | 54.9 | 1.56E−10 | 2.67E−09 | SIK3, APOA1, APOC3, APOA4, APOA5, ZNF259, BUD13 |
| chr5: 16,809,673-16,821,033 | q14.1 | Loss | 11,360 | 63.6 | 2.6 | 61.0 | 4.45E−12 | 1.48E−10 | BUD13 |
| chr5: 16,821,033-16,834,415 | q14.1 | Loss | 13,382 | 66.7 | 2.6 | 64.0 | 6.76E−12 | 3.91E−11 | LOC479430 |
| chr5: 16,834,415-16,847,536 | q14.1 | Loss | 13,121 | 69.7 | 2.6 | 67.1 | 9.50E−14 | 1.12E−11 | LOC479430 |
| chr5: 16,847,536-16,879,661 | q14.1 | Loss | 32,125 | 72.7 | 3.9 | 68.8 | 9.86E−14 | 1.12E−11 | LOC610527 |
| chr5: 16,879,661-16,894,745 | q14.1 | Loss | 15,084 | 72.7 | 5.3 | 67.5 | 6.18E−13 | 3.91E−11 | LOC610527 |
| chr5: 16,894,745-16,911,794 | q14.1 | Loss | 17,049 | 72.7 | 6.6 | 66.1 | 3.20E−12 | 1.22E−10 | |
| chr5: 16,911,794-17,003,811 | q14.1 | Loss | 92,017 | 72.7 | 7.9 | 64.8 | 1.43E−11 | 4.38E−10 | |
| chr5: 17,003,811-17,271,198 | q14.1 | Loss | 267,387 | 81.8 | 7.9 | 73.9 | 2.80E−14 | 7.01E−12 | |
| chr5: 17,271,198-17,298,351 | q14.1 | Loss | 27,153 | 75.8 | 3.9 | 71.8 | 1.21E−14 | 3.54E−12 | |
| chr5: 17,298,351-17,399,902 | q14.1 q14.2 | Loss | 101,551 | 72.7 | 3.9 | 68.8 | 9.86E−14 | 1.12E−11 | LOC102153762 |
| chr5: 17,399,902-17,524,675 | q14.2 | Loss | 124,773 | 69.7 | 3.9 | 65.7 | 7.29E−13 | 4.00E−11 | LOC102153762 |
| chr5: 17,524,675-17,736,000 | q14.2 | Loss | 211,325 | 66.7 | 3.9 | 62.7 | 4.94E−12 | 1.59E−10 | LOC102153809, LOC102153862, LOC102153906 |
| chr5: 17,736,000-17,762,360 | q14.2 | Loss | 26,360 | 66.7 | 2.6 | 64.0 | 6.76E−13 | 3.91E−11 | |
| chr5: 17,762,360-17,778,609 | q14.2 | Loss | 16,249 | 57.6 | 2.6 | 54.9 | 1.56E−10 | 2.67E−09 | |
| chr5: 17,778,609-17,796,114 | q14.2 | Loss | 17,505 | 54.5 | 2.6 | 51.9 | 8.40E−10 | 1.18E−08 | |
| chr5: 18,030,450-18,175,274 | q14.2 | Loss | 144,824 | 63.6 | 2.6 | 61.0 | 4.45E−12 | 1.48E−10 | CADM1 |
| chr5: 18,175,274-18,276,940 | q14.2 | Loss | 101,666 | 66.7 | 2.6 | 64.0 | 6.76E−13 | 3.91E−11 | CADM1 |
| chr5: 18,276,940-18,351,440 | q14.2 | Loss | 74,500 | 69.7 | 2.6 | 67.1 | 9.50E−14 | 1.12E−11 | NXPE4 |
| chr5: 18,351,440-18,363,393 | q14.2 | Loss | 11,953 | 69.7 | 3.9 | 65.7 | 7.29E−13 | 4.00E−11 | NXPE4 |
| chr5: 18,363,393-18,596,946 | q14.2 | Loss | 233,553 | 72.7 | 3.9 | 68.8 | 9.86E−14 | 1.12E−11 | NXPE4, SCN2B |
| chr5: 18,596,946-18,657,666 | q14.2-q14.3 | Loss | 60,720 | 54.5 | 3.9 | 50.6 | 4.94E−09 | 5.94E−08 | NXPE4 |
| chr5: 18,657,666-18,880,390 | q14.3 | Loss | 222,724 | 54.5 | 2.6 | 51.9 | 8.40E−10 | 1.18E−08 | NXPE4, FAM55A |
| chr5: 19,010,922-19,060,287 | q14.3 | Loss | 49,365 | 54.5 | 2.6 | 51.9 | 8.40E−10 | 1.18E−08 | NNMT |
| chr5: 19,060,287-19,074,393 | q14.3 | Loss | 14,106 | 57.6 | 5.3 | 52.3 | 4.74E−09 | 5.74E−08 | LOC489397 |
| chr5: 19,074,393-19,270,731 | q14.3 | Loss | 196,338 | 69.7 | 10.5 | 59.2 | 1.18E−09 | 1.59E−08 | ZBTB16 |
| chr5: 19,270,731-19,281,974 | q14.3 | Loss | 11,243 | 75.8 | 10.5 | 65.2 | 3.08E−11 | 6.77E−10 | ZBTB16 |
| chr5: 19,281,974-19,336,090 | q14.3 | Loss | 54,116 | 78.8 | 11.8 | 66.9 | 1.49E−11 | 4.38E−10 | ZBTB16, LOC102155430, HTR3A |
| chr5: 19,336,090-19,348,097 | q14.3 | Loss | 12,007 | 75.8 | 7.9 | 67.9 | 2.01E−12 | 9.88E−11 | HTR3A |
| chr5: 19,348,097-19,522,336 | q14.3 | Loss | 174,239 | 69.7 | 2.6 | 67.1 | 9.50E−14 | 1.12E−11 | HTR3B, SIDT2, USP28, CLDN25, ZW10 |
| chr5: 19,522,336-19,761,676 | q14.3 | Loss | 239,340 | 66.7 | 2.6 | 64.0 | 6.76E−13 | 3.91E−11 | ZW10, TMPRSS5, LOC102155912, DRD2 |
| chr5: 19,761,676-19,772,292 | q14.3 | Loss | 10,616 | 54.5 | 1.3 | 53.2 | 9.97E−11 | 1.85E−09 | DRD2 |
| chr5: 19,772,292-19,798,108 | q14.3 | Loss | 25,816 | 51.5 | 1.3 | 50.2 | 5.38E−10 | 8.10E−09 | DRD2 |
| chr5: 19,870,693-19,882,469 | q14.3 | Loss | 11,776 | 54.5 | 1.3 | 53.2 | 9.97E−11 | 1.85E−09 | TTC12 |
| chr5: 19,882,469-19,890,567 | q14.3 | Loss | 8,098 | 57.6 | 1.3 | 56.3 | 1.75E−10 | 4.38E−10 | |
| chr5: 19,890,567-19,914,466 | q14.3 | Loss | 23,899 | 60.6 | 1.3 | 59.3 | 2.88E−12 | 1.11E−10 | NCAM1 |
| chr5: 19,914,466-19,937,434 | q14.3 | Loss | 22,968 | 63.6 | 1.3 | 62.3 | 4.46E−13 | 3.02E−11 | NCAM1 |
| chr5: 19,937,434-19,990,331 | q14.3 | Loss | 52,897 | 63.6 | 2.6 | 61.0 | 4.45E−12 | 1.48E−10 | NCAM1 |
| chr5: 19,990,331-20,005,792 | q14.3 | Loss | 15,461 | 66.7 | 2.6 | 64.0 | 6.76E−13 | 3.91E−11 | NCAM1 |
| chr5: 20,005,792-20,095,665 | q14.3 | Loss | 89,623 | 63.6 | 2.6 | 61.0 | 4.45E−12 | 1.48E−10 | NCAM1 |
| chr5: 20,095,665-20,101,537 | q14.3 | Loss | 5,872 | 57.6 | 2.6 | 54.9 | 1.56E−10 | 2.67E−09 | NCAM1 |
| chr5: 20,101,537-20,117,741 | q14.3 | Loss | 16,204 | 54.5 | 2.6 | 51.9 | 8.40E−10 | 1.18E−08 | NCAM1 |
| chr5: 20,530,275-20,593,191 | q14.3 | Loss | 62,916 | 57.6 | 2.6 | 54.9 | 1.56E−10 | 2.67E−09 | |
| chr5: 20,593,191-20,741,425 | q14.3 | Loss | 148,234 | 60.6 | 2.6 | 58.0 | 2.72E−11 | 6.21E−10 | |
| chr5: 20,741,425-20,763,660 | q14.3 | Loss | 22,235 | 63.6 | 2.6 | 61.0 | 4.45E−12 | 1.48E−10 | |
| chr5: 20,763,660-20,903,254 | q14.3 | Loss | 139,594 | 69.7 | 2.6 | 67.1 | 9.50E−14 | 1.12E−11 | C5H11orf34 |
| chr5: 20,903,254-20,930,927 | q14.3 | Loss | 27,673 | 66.7 | 2.6 | 64.0 | 6.76E−13 | 3.91E−11 | PTS, BCO2 |
| chr5: 20,930,927-20,965,652 | q14.3 | Loss | 34,725 | 60.6 | 2.6 | 58.0 | 2.72E−11 | 6.21E−10 | BCO2 |
| chr5: 20,965,652-21,478,736 | q14.3 | Loss | 513,084 | 57.6 | 2.6 | 54.9 | 1.56E−10 | 2.67E−09 | TEX12, IL18, SDHD, TIMM8B, C5H11orf57, PIH1D2, DLAT, DIXDC1, C5H11orf52, HSPB2, CRYAB, C5H11orf1, FDXACB1, ALG9, PPP2R1B, SIK2 |
| chr5: 21,478,736-21,531,994 | q14.3 | Loss | 53,258 | 54.5 | 2.6 | 51.9 | 8.40E−10 | 1.18E−08 | SIK2, LOC102153351, LAYN |
| chr5: 21,592,851-21,655,541 | q14.3 | Loss | 62,690 | 54.5 | 2.6 | 51.9 | 8.40E−10 | 1.18E−08 | LOC102153632 |
| chr5: 21,655,541-21,691,724 | q14.3 | Loss | 36,183 | 57.6 | 2.6 | 54.9 | 1.56E−10 | 2.67E−09 | POU2AF1 |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| chr5: 21,691,724-21,842,858 | q14.3 | Loss | 151,134 | 60.6 | 2.6 | 58.0 | 2.72E−11 | 6.21E−10 | POU2AF1, LOC102153661, COLCA2, C5H11orf53 |
| chr5: 21,842,858-21,939,169 | q14.3 | Loss | 96,311 | 57.6 | 2.6 | 54.9 | 1.56E−10 | 2.67E−09 | LOC611159 |
| chr5: 21,939,169-22,200,189 | q14.3 | Loss | 261,020 | 54.5 | 2.6 | 51.9 | 8.40E−10 | 1.18E−08 | LOC611159, LOC100685611 |
| chr5: 22,200,189-22,469,863 | q14.3 | Loss | 269,674 | 57.6 | 2.6 | 54.9 | 1.56E−10 | 2.67E−09 | ARHGAP20, LOC102154781, FDX1 |
| chr5: 22,469,863-22,525,617 | q14.3 | Loss | 55,754 | 54.5 | 2.6 | 51.9 | 8.40E−10 | 1.18E−08 | FDX1 |
| chr5: 22,525,617-22,713,579 | q14.3 | Loss | 187,962 | 57.6 | 2.6 | 54.9 | 1.56E−10 | 2.67E−09 | RDX, ZC3H12C |
| chr5: 22,713,579-22,756,080 | q14.3 | Loss | 42,501 | 60.6 | 2.6 | 58.0 | 2.72E−11 | 6.21E−10 | ZC3H12C, LOC102154417 |
| chr5: 22,756,080-22,882,299 | q14.3 | Loss | 126,219 | 66.7 | 2.6 | 64.0 | 6.76E−13 | 3.91E−11 | |
| chr5: 22,882,299-22,956,725 | q14.3 | Loss | 74,426 | 60.6 | 2.6 | 58.0 | 2.72E−11 | 6.21E−10 | |
| chr5: 22,956,725-23,730,600 | q14.3 | Loss | 773,875 | 57.6 | 2.6 | 54.9 | 1.56E−10 | 2.67E−09 | C5H11orf87, DDX10 |
| chr5: 23,730,600-24,006,504 | q14.3 | Loss | 275,904 | 63.6 | 2.6 | 61.0 | 4.45E−12 | 1.48E−10 | DDX10 |
| chr5: 24,006,504-24,225,138 | q14.3 | Loss | 218,634 | 60.6 | 2.6 | 58.0 | 2.72E−11 | 6.21E−10 | EXPH5, KDELC2, C5H11orf65, ATM |
| chr5: 24,225,138-24,750,152 | q14.3 | Loss | 525,014 | 57.6 | 2.6 | 54.9 | 1.56E−10 | 2.67E−09 | ATM, NPAT, ACAT1, LOC102156093, CUL5, RAB39, SLC35F2, SLN |
| chr5: 25,055,292-25,232,639 | q14.3 | Loss | 177,347 | 51.5 | 1.3 | 50.2 | 5.38E−10 | 8.10E−09 | CWF19L2, LOC102157218 |
| chr5: 25,232,639-25,250,829 | q14.3 | Loss | 18,190 | 54.5 | 1.3 | 53.2 | 9.97E−11 | 1.85E−09 | |
| chr5: 25,250,829-25,684,529 | q14.3 | Loss | 433,700 | 63.6 | 3.9 | 59.7 | 3.09E−11 | 6.77E−10 | GUCY1A2 |
| chr5: 25,684,529-25,836,174 | q14.3 | Loss | 151,645 | 60.6 | 3.9 | 56.7 | 1.79E−10 | 2.97E−09 | |
| chr5: 25,836,174-26,006,165 | q14.3 | Loss | 169,991 | 54.5 | 3.9 | 50.6 | 4.94E−09 | 5.94E−08 | |
| chr5: 26,006,165-26,253,762 | q14.3 | Loss | 247,597 | 57.6 | 3.9 | 53.6 | 9.72E−10 | 1.34E−08 | AASDHPPT, KBTBD3, MSANTD4 |
| chr5: 26,253,762-26,630,899 | q14.3 | Loss | 377,137 | 57.6 | 2.6 | 54.9 | 1.56E−10 | 2.67E−09 | MSANTD4, LOC100688413, GRIA4 |
| chr5: 26,630,899-26,803,690 | q14.3 | Loss | 172,791 | 63.6 | 3.9 | 59.7 | 3.09E−11 | 6.77E−10 | GRIA4 |
| chr5: 26,803,690-26,813,706 | q14.3 | Loss | 10,016 | 60.6 | 3.9 | 56.7 | 1.79E−10 | 2.97E−09 | |
| chr5: 26,813,706-26,911,584 | q14.3 | Loss | 97,878 | 54.5 | 2.6 | 51.9 | 8.40E−10 | 1.18E−08 | |
| chr5: 26,911,584-27,034,403 | q14.3 | Loss | 122,819 | 54.5 | 1.3 | 53.2 | 9.97E−11 | 1.85E−09 | |
| chr5: 27,034,403-27,145,741 | q14.3 | Loss | 111,338 | 60.6 | 1.3 | 59.3 | 2.88E−12 | 1.11E−10 | CASP4 |
| chr5: 27,145,741-27,306,771 | q14.3-q21 | Loss | 161,030 | 60.6 | 2.6 | 58.0 | 2.72E−11 | 6.21E−10 | CASP4, CASP12, LOC479459 |
| chr5: 27,306,771-27,464,906 | q21 | Loss | 158,135 | 57.6 | 2.6 | 54.9 | 1.56E−10 | 2.67E−09 | |
| chr5: 27,464,906-27,526,152 | q21 | Loss | 61,246 | 60.6 | 2.6 | 58.0 | 2.72E−11 | 6.21E−10 | |
| chr5: 27,526,152-27,671,544 | q21 | Loss | 145,392 | 60.6 | 3.9 | 56.7 | 1.79E−10 | 2.97E−09 | |
| chr5: 27,671,544-27,702,732 | q21 | Loss | 31,188 | 54.5 | 2.6 | 51.9 | 8.40E−10 | 1.18E−08 | |
| chr5: 27,919,757-27,934,987 | q21 | Loss | 15,230 | 54.5 | 2.6 | 51.9 | 8.40E−10 | 1.18E−08 | PDGFD |
| chr5: 27,934,987-27,963,780 | q21 | Loss | 28,793 | 57.6 | 3.9 | 53.6 | 9.72E−10 | 1.34E−08 | PDGFD |
| chr5: 27,963,780-27,990,233 | q21 | Loss | 26,453 | 63.6 | 3.9 | 59.7 | 3.09E−11 | 6.77E−10 | DDI1, PDGFD |
| chr5: 27,990,233-28,106,271 | q21 | Loss | 116,038 | 66.7 | 3.9 | 62.7 | 4.94E−12 | 1.59E−10 | PDGFD |
| chr5: 28,106,271-28,202,681 | q21 | Loss | 96,410 | 57.6 | 2.6 | 54.9 | 1.56E−10 | 2.67E−09 | |
| chr5: 28,202,681-28,394,367 | q21 | Loss | 191,686 | 60.6 | 2.6 | 58.0 | 2.72E−11 | 6.21E−10 | DYNC2H1 |
| chr5: 28,394,367-28,568,040 | q21 | Loss | 173,673 | 63.6 | 2.6 | 61.0 | 4.45E−12 | 1.48E−10 | DYNC2H1 |
| chr5: 28,568,040-28,652,646 | q21 | Loss | 84,606 | 60.6 | 2.6 | 58.0 | 2.72E−11 | 6.21E−10 | DYNC2H1 |
| chr5: 28,652,646-28,704,136 | q21 | Loss | 51,490 | 57.6 | 2.6 | 54.9 | 1.56E−10 | 2.67E−09 | DYNC2H1 |
| chr5: 28,704,136-28,805,065 | q21 | Loss | 100,929 | 54.5 | 1.3 | 53.2 | 9.97E−11 | 1.85E−09 | DYNC2H1, DCUN1D5, MMP13 |
| chr5: 28,805,065-28,959,058 | q21 | Loss | 153,993 | 57.6 | 1.3 | 56.3 | 1.75E−11 | 4.38E−10 | MMP13, MMP12, MMP3 |
| chr5: 28,959,058-29,015,567 | q21 | Loss | 56,509 | 60.6 | 1.3 | 59.3 | 2.88E−12 | 1.11E−10 | LOC489428 |
| chr5: 29,015,567-29,261,694 | q21 | Loss | 246,127 | 57.6 | 1.3 | 56.3 | 1.75E−11 | 4.38E−10 | MMP8, MMP27, MMP20, MMP7, LOC100856041 |
| chr5: 29,261,694-29,285,265 | q21 | Loss | 23,571 | 54.5 | 1.3 | 53.2 | 9.97E−11 | 1.85E−09 | LOC100856041 |
| chr5: 29,285,265-29,647,998 | q21 | Loss | 362,733 | 51.5 | 1.3 | 50.2 | 5.38E−10 | 8.10E−09 | LOC102154369, BIRC2, BIRC3, LOC102153712, YAP1, LOC102153832, C5H11orf70, KIAA1377 |
| chr5: 29,647,998-29,926,991 | q21 | Loss | 278,993 | 54.5 | 1.3 | 53.2 | 9.97E−11 | 1.85E−09 | KIAA1377, ANGPTL5, TRPC6 |
| chr5: 29,926,991-29,943,628 | q21 | Loss | 16,637 | 63.6 | 2.6 | 61.0 | 4.45E−12 | 1.48E−10 | TRPC6 |
| chr5: 29,943,628-30,117,141 | q21 | Loss | 173,513 | 66.7 | 2.6 | 64.0 | 6.76E−13 | 3.91E−11 | TRPC6 |
| chr5: 30,117,141-30,292,482 | q21 | Loss | 175,341 | 69.7 | 2.6 | 67.1 | 9.50E−14 | 1.12E−11 | ZZEF1, CYB5D2, ANKFY1 |
| chr5: 30,292,482-30,412,787 | q21 | Loss | 120,305 | 72.7 | 2.6 | 70.1 | 1.22E−14 | 3.54E−12 | ANKFY1, UBE2G1 |
| chr5: 30,412,787-30,460,632 | q21 | Loss | 47,845 | 66.7 | 2.6 | 64.0 | 6.76E−13 | 3.91E−11 | |
| chr5: 30,460,632-30,475,453 | q21 | Loss | 14,821 | 69.7 | 9.2 | 60.5 | 3.47E−10 | 5.61E−09 | SPNS3 |
| chr5: 30,475,453-30,505,927 | q21 | Loss | 30,474 | 69.7 | 10.5 | 59.2 | 1.18E−09 | 1.59E−08 | SPNS3, SPNS2 |
| chr5: 30,505,927-30,624,645 | q21 | Loss | 118,718 | 69.7 | 13.2 | 56.5 | 1.07E−08 | 1.25E−07 | SPNS2, MYBBP1A, GGT6, LOC102155027, SMTNL2, TEKT1, FBXO39 |
| chr5: 30,624,645-30,629,434 | q21 | Loss | 4,789 | 75.8 | 14.5 | 61.3 | 9.65E−10 | 1.34E−08 | XAF1 |
| chr5: 30,629,434-30,839,322 | q21 | Loss | 209,888 | 75.8 | 17.1 | 58.7 | 6.96E−09 | 8.23E−08 | XAF1, SLC13A5, MED31, TXNDC17, KIAA0753, LOC102156039, PITPNM3, FAM64A, AIPL1 |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| chr5: 30,839,322-30,858,577 | q21 | Loss | 19,255 | 78.8 | 18.4 | 60.4 | 3.01E−09 | 3.86E−08 | |
| chr5: 30,858,577-30,879,260 | q21 | Loss | 20,683 | 78.8 | 19.7 | 59.1 | 1.06E−08 | 1.24E−07 | |
| chr5: 30,879,260-30,944,859 | q21 | Loss | 65,599 | 81.8 | 21.1 | 60.8 | 3.71E−09 | 4.73E−08 | LOC102156228, LOC102156296 |
| chr5: 30,944,859-30,994,655 | q21 | Loss | 49,796 | 81.8 | 22.4 | 59.4 | 7.25E−09 | 8.55E−08 | LOC102156392, LOC102156440 |
| chr5: 30,994,655-31,066,726 | q21 | Loss | 72,071 | 81.8 | 23.7 | 58.1 | 2.51E−08 | 2.75E−07 | WSCD1 |
| chr5: 31,066,726-31,080,498 | q21 | Loss | 13,772 | 81.8 | 25.0 | 56.8 | 3.93E−08 | 4.27E−07 | |
| chr5: 31,096,931-31,168,215 | q21 | Loss | 71,284 | 72.7 | 15.8 | 56.9 | 1.47E−08 | 1.65E−07 | |
| chr5: 31,168,215-31,189,337 | q21 | Loss | 21,122 | 69.7 | 15.8 | 53.9 | 7.35E−08 | 7.77E−07 | |
| chr5: 31,189,337-31,203,739 | q21 | Loss | 14,402 | 72.7 | 15.8 | 56.9 | 1.47E−08 | 1.65E−07 | |
| chr5: 31,203,739-31,220,304 | q21 | Loss | 16,565 | 72.7 | 14.5 | 58.3 | 5.56E−09 | 6.58E−08 | |
| chr5: 31,220,304-31,307,195 | q21 | Loss | 86,891 | 69.7 | 5.3 | 64.4 | 4.36E−12 | 1.48E−10 | NLRP1 |
| chr5: 31,307,195-31,369,071 | q21 | Loss | 61,876 | 69.7 | 3.9 | 65.7 | 7.29E−13 | 4.00E−11 | LOC100688504, MIS12, DERL2, DHX33, C1QBP, RPAIN, NUP88 |
| chr5: 31,369,071-31,385,315 | q21 | Loss | 16,244 | 72.7 | 3.9 | 68.8 | 9.86E−14 | 1.12E−11 | NUP88 |
| chr5: 31,385,315-31,404,096 | q21 | Loss | 18,781 | 69.7 | 3.9 | 65.7 | 7.29E−13 | 4.00E−11 | NUP88, RABEP1 |
| chr5: 31,404,096-31,417,175 | q21 | Loss | 13,079 | 69.7 | 2.6 | 67.1 | 9.50E−14 | 1.12E−11 | RABEP1 |
| chr5: 31,417,175-31,430,511 | q21 | Loss | 13,336 | 72.7 | 2.6 | 70.1 | 1.22E−14 | 3.54E−12 | RABEP1 |
| chr5: 31,430,511-31,535,668 | q21 | Loss | 105,157 | 69.7 | 1.3 | 68.4 | 8.56E−15 | 3.54E−12 | RABEP1, SCIMP, ZFP3 |
| chr5: 31,535,668-31,580,505 | q21 | Loss | 44,837 | 66.7 | 1.3 | 65.4 | 6.42E−14 | 9.66E−12 | SCIMP, ZFP3 |
| chr5: 31,580,505-31,601,294 | q21 | Loss | 20,789 | 60.6 | 1.3 | 59.3 | 2.88E−12 | 1.11E−10 | ZFP3 |
| chr5: 31,601,294-31,622,778 | q21 | Loss | 21,484 | 60.6 | 2.6 | 58.0 | 2.72E−11 | 6.21E−10 | KIF1C |
| chr5: 31,622,778-31,685,371 | q21 | Loss | 62,593 | 57.6 | 2.6 | 54.9 | 1.56E−10 | 2.67E−09 | KIF1C, INCA1, CAMTA2, SPAG7, ENO3, PFN1, RNF167, SLC25A11, GP1BA |
| chr5: 31,685,371-31,700,554 | q21 | Loss | 15,183 | 60.6 | 2.6 | 58.0 | 2.72E−11 | 6.21E−10 | |
| chr5: 31,700,554-31,712,954 | q21 | Loss | 12,400 | 60.6 | 3.9 | 56.7 | 1.79E−10 | 2.97E−09 | CHRNE, C5H17orf107, MINK1 |
| chr5: 31,712,954-31,739,657 | q21 | Loss | 26,703 | 66.7 | 3.9 | 62.7 | 4.94E−12 | 1.59E−10 | MINK1 |
| chr5: 31,739,657-31,749,780 | q21 | Loss | 10,123 | 66.7 | 2.6 | 64.0 | 6.76E−13 | 3.91E−11 | MINK1 |
| chr5: 31,749,780-31,910,093 | q21 | Loss | 160,313 | 66.7 | 1.3 | 65.4 | 6.42E−14 | 9.66E−12 | MINK1, PLD2, PSMB6, GLTPD2, VMO1, TM4SF5, ZMYND15, CXCL16, MED11, ARRB2, PELP1, ALOX15 |
| chr5: 31,910,093-32,088,235 | q21 | Loss | 178,142 | 66.7 | 2.6 | 64.0 | 6.76E−13 | 3.91E−11 | LOC607567, LOC102155409, ALOX12, RNASEK, C5H17orf49, BCL6B, SLC16A13, SLC16A11, LOC102156250 |
| chr5: 32,088,235-32,106,863 | q21 | Loss | 18,628 | 66.7 | 7.9 | 58.8 | 5.39E−10 | 8.10E−09 | CLEC10A |
| chr5: 32,106,863-32,183,648 | q21 | Loss | 76,785 | 69.7 | 11.8 | 57.9 | 3.69E−09 | 4.71E−08 | ASGR2, ASGR1, DLG4 |
| chr5: 32,411,753-32,430,833 | q21 | Loss | 19,080 | 57.6 | 1.3 | 56.3 | 1.75E−11 | 4.38E−10 | POLR2A |
| chr5: 32,430,833-32,545,540 | q21 | Loss | 114,707 | 60.6 | 1.3 | 59.3 | 2.88E−12 | 1.11E−10 | LOC102153734, TNFSF12, TNFSF13, SENP3, EIF4A1, CD68, MPDU1, SOX15, FXR2, SAT2, SHBG |
| chr5: 32,545,540-32,659,365 | q21 | Loss | 113,825 | 60.6 | 2.6 | 58.0 | 2.72E−11 | 6.21E−10 | ATP1B2, TP53, WRAP53, EFNB3, DNAH2 |
| chr5: 32,659,365-32,708,735 | q21 | Loss | 49,370 | 57.6 | 2.6 | 54.9 | 1.56E−10 | 2.67E−09 | DNAH2, LOC102155246, KDM6B |
| chr5: 32,708,735-32,807,894 | q21-q22 | Loss | 99,159 | 57.6 | 1.3 | 56.3 | 1.75E−11 | 4.38E−10 | KDM6B, TMEM88, NAA38, CYB5D1, LOC102155431, CHD3, LOC102155855, KCNAB3, TRAPPC1, CNTROB |
| chr5: 32,807,894-32,866,241 | q22 | Loss | 58,347 | 54.5 | 1.3 | 53.2 | 9.97E−11 | 1.85E−09 | CNTROB, GUCY2D |
| chr5: 32,866,241-32,905,477 | q22 | Loss | 39,236 | 51.5 | 1.3 | 50.2 | 5.38E−10 | 8.10E−09 | ALOX15B, ALOX12B |
| chr5: 32,905,477-33,112,862 | q22 | Loss | 207,385 | 54.5 | 1.3 | 53.2 | 9.97E−11 | 1.85E−09 | ALOX12B, ALOXE3, HES7, PER1, VAMP2, LOC102157040, TMEM107, C5H17orf59, AURKB, CTC1, PFAS, RANGRF, SLC25A35, ARHGEF15 |
| chr5: 33,112,862-33,421,296 | q22 | Loss | 308,434 | 60.6 | 1.3 | 59.3 | 2.88E−12 | 1.11E−10 | ODF4, KRBA2, RPL26, RNF222, NDEL1, MYH10 |
| chr5: 33,421,296-33,693,288 | q22 | Loss | 271,992 | 63.6 | 1.3 | 62.3 | 4.46E−13 | 3.02E−11 | CCDC42, MFSD6L, PIK3R6, PIK3R5, LOC102155775, LOC102155856, NTN1 |
| chr5: 33,693,288-33,705,238 | q22 | Loss | 11,950 | 66.7 | 1.3 | 65.4 | 6.42E−14 | 9.66E−12 | NTN1 |
| chr5: 33,705,238-33,851,152 | q22 | Loss | 145,914 | 69.7 | 3.9 | 65.7 | 7.29E−13 | 4.00E−11 | NTN1 |
| chr5: 33,851,152-33,989,233 | q22 | Loss | 138,081 | 72.7 | 3.9 | 68.8 | 9.86E−14 | 1.12E−11 | STX8 |
| chr5: 33,989,233-34,071,975 | q22 | Loss | 82,742 | 69.7 | 1.3 | 68.4 | 8.56E−15 | 3.54E−12 | STX8 |
| chr5: 34,071,975-34,105,056 | q22 | Loss | 33,081 | 66.7 | 1.3 | 65.4 | 6.42E−14 | 9.66E−12 | STX8, WDR16 |
| chr5: 34,105,056-34,123,099 | q22 | Loss | 18,043 | 63.6 | 1.3 | 62.3 | 4.46E−13 | 3.02E−11 | WDR16 |
| chr5: 34,123,099-34,198,416 | q22 | Loss | 75,317 | 60.6 | 1.3 | 59.3 | 2.88E−12 | 1.11E−10 | WDR16, USP43 |
| chr5: 34,198,416-34,217,677 | q22 | Loss | 19,261 | 60.6 | 0.0 | 60.6 | 1.59E−13 | 1.60E−11 | |
| chr5: 34,217,677-34,270,966 | q22 | Loss | 53,289 | 57.6 | 0.0 | 57.6 | 1.02E−12 | 5.07E−11 | DHRS7C, GLP2R |
| chr5: 34,270,966-34,285,525 | q22 | Loss | 14,559 | 60.6 | 1.3 | 59.3 | 2.88E−12 | 1.11E−10 | GLP2R |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| chr5: 34,285,525-34,386,603 | q22 | Loss | 101,078 | 63.6 | 2.6 | 61.0 | 4.45E-12 | 1.48E-10 | GLP2R, RCVRN, LOC479467, GAS7 |
| chr5: 34,386,603-34,530,246 | q22 | Loss | 143,643 | 60.6 | 1.3 | 59.3 | 2.88E-12 | 1.11E-10 | LOC479467, GAS7 |
| chr5: 34,530,246-34,682,629 | q22 | Loss | 152,383 | 69.7 | 1.3 | 68.4 | 8.56E-15 | 3.54E-12 | MYH13 |
| chr5: 34,682,629-34,687,626 | q22 | Loss | 4,997 | 72.7 | 2.6 | 70.1 | 1.22E-14 | 3.54E-12 | |
| chr5: 34,687,626-34,700,809 | q22 | Loss | 13,183 | 75.8 | 2.6 | 73.1 | 1.43E-15 | 2.15E-12 | MYH8 |
| chr5: 34,700,809-34,733,618 | q22 | Loss | 32,809 | 78.8 | 2.6 | 76.2 | 1.50E-16 | 1.13E-12 | MYH8 |
| chr5: 34,733,618-34,739,360 | q22 | Loss | 5,742 | 72.7 | 2.6 | 70.1 | 1.22E-14 | 3.54E-12 | |
| chr5: 34,739,360-34,749,464 | q22 | Loss | 10,104 | 66.7 | 2.6 | 64.0 | 6.76E-13 | 3.91E-11 | MYH4 |
| chr5: 34,749,464-34,757,802 | q22 | Loss | 8,338 | 66.7 | 1.3 | 65.4 | 6.42E-14 | 9.66E-12 | MYH4 |
| chr5: 34,757,802-34,763,799 | q22 | Loss | 5,997 | 63.6 | 1.3 | 62.3 | 4.46E-13 | 3.02E-11 | MYH4 |
| chr5: 34,763,799-34,888,925 | q22 | Loss | 125,126 | 54.5 | 1.3 | 53.2 | 9.97E-11 | 1.85E-09 | MYH4, MYH1, MYH2 |
| chr5: 34,888,925-34,900,363 | q22 | Loss | 11,438 | 57.6 | 1.3 | 56.3 | 1.75E-11 | 4.38E-10 | |
| chr5: 34,900,363-34,924,941 | q22 | Loss | 24,578 | 60.6 | 1.3 | 59.3 | 2.88E-12 | 1.11E-10 | MYH3 |
| chr5: 34,924,941-34,997,381 | q22 | Loss | 72,440 | 63.6 | 1.3 | 62.3 | 4.46E-13 | 3.02E-11 | MYH3, SCO1, ADPRM, TMEM220 |
| chr5: 34,997,381-35,219,397 | q22 | Loss | 222,016 | 63.6 | 2.6 | 61.0 | 4.45E-12 | 1.48E-10 | PIRT |
| chr5: 35,219,397-35,273,015 | q22 | Loss | 53,618 | 69.7 | 2.6 | 67.1 | 9.50E-14 | 1.12E-11 | GPS2 |
| chr5: 35,273,015-35,289,492 | q22 | Loss | 16,477 | 72.7 | 2.6 | 70.1 | 1.22E-14 | 3.54E-12 | |
| chr5: 35,289,492-35,344,382 | q22 | Loss | 54,890 | 78.8 | 3.9 | 74.8 | 1.33E-15 | 2.15E-12 | |
| chr5: 35,344,382-35,933,510 | q22 | Loss | 589,128 | 78.8 | 5.3 | 73.5 | 9.14E-15 | 3.54E-12 | SAT2, SHISA6, SHBG, DNAH9 |
| chr5: 35,933,510-36,039,948 | q22 | Loss | 106,438 | 75.8 | 3.9 | 71.8 | 1.21E-14 | 3.54E-12 | DNAH9 |
| chr5: 36,039,948-36,069,307 | q22 | Loss | 29,359 | 63.6 | 1.3 | 62.3 | 4.46E-13 | 3.02E-11 | DNAH9, ZNF18 |
| chr5: 36,069,307-36,339,529 | q22 | Loss | 270,222 | 60.6 | 1.3 | 59.3 | 2.88E-12 | 1.11E-10 | ZNF18, LOC100685794, MAP2K4, LOC102155074, LOC102155028 |
| chr5: 36,339,529-36,352,015 | q22 | Loss | 12,486 | 57.6 | 1.3 | 56.3 | 1.75E-11 | 4.38E-10 | LOC102155130 |
| chr5: 36,352,015-36,361,706 | q22 | Loss | 9,691 | 54.5 | 1.3 | 53.2 | 9.97E-11 | 1.85E-09 | LOC102155130 |
| chr5: 36,361,706-36,635,379 | q22-q23 | Loss | 273,673 | 51.5 | 1.3 | 50.2 | 5.38E-10 | 8.10E-09 | LOC102155130, LOC102155247 |
| chr5: 36,635,379-36,706,216 | q23 | Loss | 70,837 | 57.6 | 1.3 | 56.3 | 1.75E-11 | 4.38E-10 | MYOCD |
| chr5: 36,706,216-36,723,188 | q23 | Loss | 16,972 | 63.6 | 1.3 | 62.3 | 4.46E-13 | 3.02E-11 | MYOCD |
| chr5: 36,723,188-36,935,181 | q23 | Loss | 211,993 | 66.7 | 1.3 | 65.4 | 6.42E-14 | 9.66E-12 | MYOCD, ARHGAP44 |
| chr5: 36,935,181-36,991,263 | q23 | Loss | 56,082 | 63.6 | 1.3 | 62.3 | 4.46E-13 | 3.02E-11 | ARHGAP44, ELAC2, LOC102156372 |
| chr5: 36,991,263-37,077,985 | q23 | Loss | 86,722 | 54.5 | 1.3 | 53.2 | 9.97E-11 | 1.85E-09 | LOC102156372 |
| chr5: 37,077,985-37,345,754 | q23 | Loss | 267,769 | 51.5 | 1.3 | 50.2 | 5.38E-10 | 8.10E-09 | LOC102156372, LOC102155885, LOC102155946, LOC102156000 |
| chr5: 37,345,754-37,378,710 | q23 | Loss | 32,956 | 54.5 | 1.3 | 53.2 | 9.97E-11 | 1.85E-09 | |
| chr5: 37,378,710-37,400,359 | q23 | Loss | 21,649 | 57.6 | 1.3 | 56.3 | 1.75E-11 | 4.38E-10 | |
| chr5: 37,400,359-37,418,572 | q23 | Loss | 18,213 | 60.6 | 1.3 | 59.3 | 2.88E-12 | 1.11E-10 | HS3ST3A1 |
| chr5: 37,418,572-37,430,842 | q23 | Loss | 12,270 | 63.6 | 1.3 | 62.3 | 4.46E-13 | 3.02E-11 | HS3ST3A1 |
| chr5: 37,430,842-37,475,789 | q23 | Loss | 44,947 | 66.7 | 2.6 | 64.0 | 6.76E-13 | 3.91E-11 | HS3ST3A1 |
| chr5: 37,475,789-37,752,244 | q23 | Loss | 276,455 | 69.7 | 2.6 | 67.1 | 9.50E-14 | 1.12E-11 | HS3ST3A1, LOC608351, LOC102156188 |
| chr5: 37,752,244-37,788,552 | q23 | Loss | 36,308 | 72.7 | 2.6 | 70.1 | 1.22E-14 | 3.54E-12 | |
| chr5: 37,788,552-37,966,845 | q23 | Loss | 178,293 | 75.8 | 2.6 | 73.1 | 1.43E-15 | 2.15E-12 | COX10 |
| chr5: 37,966,845-37,978,756 | q23 | Loss | 11,911 | 72.7 | 2.6 | 70.1 | 1.22E-14 | 3.54E-12 | COX10 |
| chr5: 37,978,756-37,989,010 | q23 | Loss | 10,254 | 72.7 | 1.3 | 71.4 | 1.05E-15 | 2.15E-12 | COX10 |
| chr5: 37,989,010-38,005,708 | q23 | Loss | 16,698 | 69.7 | 1.3 | 68.4 | 8.56E-15 | 3.54E-12 | |
| chr5: 38,005,708-38,024,187 | q23 | Loss | 18,479 | 66.7 | 1.3 | 65.4 | 6.42E-14 | 9.66E-12 | HS3ST3B1 |
| chr5: 38,024,187-38,065,129 | q23 | Loss | 40,942 | 60.6 | 1.3 | 59.3 | 2.88E-12 | 1.11E-10 | HS3ST3B1 |
| chr5: 38,065,129-38,389,508 | q23 | Loss | 324,379 | 57.6 | 1.3 | 56.3 | 1.75E-11 | 4.38E-10 | HS3ST3B1 |
| chr5: 38,389,508-38,483,690 | q23 | Loss | 94,182 | 54.5 | 1.3 | 53.2 | 9.97E-11 | 1.85E-09 | |
| chr5: 38,483,690-38,679,152 | q23 | Loss | 195,462 | 51.5 | 1.3 | 50.2 | 5.38E-10 | 8.10E-09 | LOC102156520 |
| chr5: 38,679,152-38,863,984 | q23 | Loss | 184,832 | 54.5 | 1.3 | 53.2 | 9.97E-11 | 1.85E-09 | LOC608772, PMP22 |
| chr5: 38,863,984-39,121,648 | q23 | Loss | 257,664 | 51.5 | 1.3 | 50.2 | 5.38E-10 | 8.10E-09 | TEKT3, LOC102156927, CDRT4, TVP23B, FBXW10 |
| chr5: 39,121,648-39,256,137 | q23 | Loss | 134,489 | 54.5 | 1.3 | 53.2 | 9.97E-11 | 1.85E-09 | FBXW10, LOC489518, LOC102151571, LOC608913, ZNF286A |
| chr5: 39,256,137-39,810,518 | q23 | Loss | 554,381 | 51.5 | 1.3 | 50.2 | 5.38E-10 | 8.10E-09 | ZNF624, ZNF287, FAM211A, LOC100687347, TRPV2, UBB, CENPV, LOC100687735, PIGL, NCOR1 |
| chr5: 39,810,518-39,860,472 | q23 | Loss | 49,954 | 57.6 | 1.3 | 56.3 | 1.75E-11 | 4.38E-10 | NCOR1, TTC19 |
| chr5: 39,860,472-39,897,741 | q23 | Loss | 37,269 | 54.5 | 1.3 | 53.2 | 9.97E-11 | 1.85E-09 | TTC19, ZSWIM7, ADORA2B |
| chr5: 39,897,741-39,943,405 | q23 | Loss | 45,664 | 57.6 | 1.3 | 56.3 | 1.75E-11 | 4.38E-10 | ADORA2B, SPECC1 |
| chr5: 39,943,405-39,953,861 | q23 | Loss | 10,456 | 63.6 | 1.3 | 62.3 | 4.46E-13 | 3.02E-11 | SPECC1 |
| chr5: 39,953,861-40,463,632 | q23-q24 | Loss | 509,771 | 66.7 | 1.3 | 65.4 | 6.42E-14 | 9.66E-12 | SPECC1, AKAP10, ULK2 |
| chr5: 40,463,632-40,474,878 | q24 | Loss | 11,246 | 63.6 | 1.3 | 62.3 | 4.46E-13 | 3.02E-11 | ALDH3A1 |
| chr5: 40,474,878-40,479,655 | q24 | Loss | 4,777 | 60.6 | 1.3 | 59.3 | 2.88E-12 | 1.11E-10 | |
| chr5: 40,479,655-40,550,707 | q24 | Loss | 71,052 | 57.6 | 1.3 | 56.3 | 1.75E-11 | 4.38E-10 | SLC47A2, ALDH3A2 |
| chr5: 40,550,707-40,588,700 | q24 | Loss | 37,993 | 60.6 | 1.3 | 59.3 | 2.88E-12 | 1.11E-10 | LOC100688308 |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| chr5: 40,588,700-40,763,870 | q24 | Loss | 175,170 | 63.6 | 1.3 | 62.3 | 4.46E−13 | 3.02E−11 | LOC100688308, SLC47A1 |
| chr5: 40,763,870-40,829,794 | q24 | Loss | 65,924 | 60.6 | 1.3 | 59.3 | 2.88E−12 | 1.11E−10 | RNF112, MFAP4 |
| chr5: 40,829,794-41,116,952 | q24 | Loss | 287,158 | 57.6 | 1.3 | 56.3 | 1.75E−11 | 4.38E−10 | MFAP4, MAPK7, B9D1, EPN2, GRAP, SLC5A10, FAM83G |
| chr5: 41,116,952-41,198,148 | q24 | Loss | 81,196 | 54.5 | 1.3 | 53.2 | 9.97E−11 | 1.85E−09 | PRPSAP2 |
| chr5: 41,198,148-41,286,067 | q24 | Loss | 87,919 | 57.6 | 1.3 | 56.3 | 1.75E−11 | 4.38E−10 | SHMT1, SMCR8, TOP3A |
| chr5: 41,286,067-41,401,440 | q24 | Loss | 115,373 | 54.5 | 1.3 | 53.2 | 9.97E−11 | 1.85E−09 | TOP3A, SMCR7, FLII, LLGL1, ALKBH5, MYO15A |
| chr5: 41,401,440-41,429,338 | q24 | Loss | 27,898 | 57.6 | 1.3 | 56.3 | 1.75E−11 | 4.38E−10 | MYO15A, DRG2 |
| chr5: 41,429,338-41,749,755 | q24 | Loss | 320,417 | 60.6 | 1.3 | 59.3 | 2.88E−12 | 1.11E−10 | DRG2, GID4, ATPAF2, LRRC48, TOM1L2, SREBF1, RAI1 |
| chr5: 41,749,755-41,925,434 | q24 | Loss | 175,679 | 63.6 | 1.3 | 62.3 | 4.46E−13 | 3.02E−11 | RAI1, PEMT |
| chr5: 41,925,434-41,961,024 | q24 | Loss | 35,590 | 60.6 | 1.3 | 59.3 | 2.88E−12 | 1.11E−10 | PEMT |
| chr5: 41,961,024-42,181,266 | q24 | Loss | 220,242 | 63.6 | 1.3 | 62.3 | 4.46E−13 | 3.02E−11 | RASD1, MED9, NT5M, COPS3, FLCN |
| chr5: 42,181,266-42,235,930 | q24 | Loss | 54,664 | 66.7 | 1.3 | 65.4 | 6.42E−14 | 9.66E−12 | FLCN, PLD6, LOC479530 |
| chr5: 42,235,930-42,279,703 | q24 | Loss | 43,773 | 63.6 | 1.3 | 62.3 | 4.46E−13 | 3.02E−11 | LOC479530 |
| chr5: 42,279,703-42,604,639 | q24 | Loss | 324,936 | 60.6 | 1.3 | 59.3 | 2.88E−12 | 1.11E−10 | LOC479530, LOC102153190, TNFRSF13B, USP22, DHRS7B |
| chr5: 42,604,639-42,747,794 | q24 | Loss | 143,155 | 54.5 | 1.3 | 53.2 | 9.97E−11 | 1.85E−09 | DHRS7B, TMEM11, LOC102153833, C5H17orf103, LOC102154017, MAP2K3 |
| chr5: 42,747,794-42,904,466 | q24 | Loss | 156,672 | 57.6 | 1.3 | 56.3 | 1.75E−11 | 4.38E−10 | MAP2K3, KCNJ12, LOC102157145 |
| chr5: 42,904,466-42,966,420 | q24 | Loss | 61,954 | 57.6 | 3.9 | 53.6 | 9.72E−10 | 1.34E−08 | LOC102154136 |
| chr5: 42,966,420-43,008,464 | q24 | Loss | 42,044 | 63.6 | 3.9 | 59.7 | 3.09E−11 | 6.77E−10 | |
| chr5: 43,008,464-43,076,302 | q24 | Loss | 67,838 | 60.6 | 3.9 | 56.7 | 1.79E−10 | 2.97E−09 | LOC102154367 |
| chr5: 43,076,302-43,189,705 | q24 | Loss | 113,403 | 54.5 | 2.6 | 51.9 | 8.40E−10 | 1.18E−08 | SERBP1 |
| chr5: 43,189,705-43,361,590 | q24 | Loss | 171,885 | 51.5 | 1.3 | 50.2 | 5.38E−10 | 8.10E−09 | LOC102154658, IL12RB2, IL23R |
| chr5: 43,361,590-43,470,080 | q24 | Loss | 108,490 | 54.5 | 1.3 | 53.2 | 9.97E−11 | 1.85E−09 | IL23R, LOC609111, C5H1orf141 |
| chr5: 43,470,080-43,483,708 | q24 | Loss | 13,628 | 51.5 | 1.3 | 50.2 | 5.38E−10 | 8.10E−09 | LOC100685241 |
| chr5: 44,768,774-45,069,038 | q24 | Loss | 300,264 | 54.5 | 2.6 | 51.9 | 8.40E−10 | 1.18E−08 | LEPR, LOC102156371, LOC609115, DNAJC6, AK4 |
| chr5: 48,016,459-48,445,801 | q24 | Loss | 429,342 | 54.5 | 2.6 | 51.9 | 8.40E−10 | 1.18E−08 | INADL, LOC479551 |
| chr5: 49,551,942-50,021,095 | q24 | Loss | 469,153 | 54.5 | 2.6 | 51.9 | 8.40E−10 | 1.18E−08 | C5H1orf87, CYP2J2, HOOK1 |
| chr5: 50,047,157-50,091,376 | q24 | Loss | 44,219 | 54.5 | 2.6 | 51.9 | 8.40E−10 | 1.18E−08 | HOOK1 |
| chr5: 50,091,376-50,114,330 | q24 | Loss | 22,954 | 54.5 | 1.3 | 53.2 | 9.97E−11 | 1.85E−09 | FGGY |
| chr5: 50,114,330-50,436,698 | q24 | Loss | 322,368 | 51.5 | 1.3 | 50.2 | 5.38E−10 | 8.10E−09 | FGGY |
| chr5: 50,436,698-50,448,468 | q24 | Loss | 11,770 | 51.5 | 0.0 | 51.5 | 3.58E−11 | 7.73E−10 | FGGY |
| chr5: 51,048,547-51,059,816 | q31 | Loss | 11,269 | 57.6 | 1.3 | 56.3 | 1.75E−11 | 4.38E−10 | MYSM1 |
| chr5: 51,059,816-51,252,744 | q31 | Loss | 192,928 | 60.6 | 1.3 | 59.3 | 2.88E−12 | 1.11E−10 | MYSM1, TACSTD2, OMA1 |
| chr5: 51,252,744-51,563,921 | q31 | Loss | 311,177 | 57.6 | 1.3 | 56.3 | 1.75E−11 | 4.38E−10 | DAB1 |
| chr5: 51,563,921-52,014,031 | q31 | Loss | 450,110 | 54.5 | 1.3 | 53.2 | 9.97E−11 | 1.85E−09 | LOC102156041, DAB1 |
| chr5: 52,014,031-52,106,690 | q31 | Loss | 92,659 | 57.6 | 1.3 | 56.3 | 1.75E−11 | 4.38E−10 | DAB1 |
| chr5: 52,106,690-52,139,816 | q31 | Loss | 33,126 | 60.6 | 2.6 | 58.0 | 2.72E−11 | 6.21E−10 | DAB1 |
| chr5: 52,139,816-52,284,795 | q31 | Loss | 144,979 | 63.6 | 2.6 | 61.0 | 4.45E−12 | 1.48E−10 | DAB1 |
| chr5: 52,284,795-52,533,879 | q31 | Loss | 249,084 | 54.5 | 1.3 | 53.2 | 9.97E−11 | 1.85E−09 | DAB1 |
| chr5: 54,303,571-54,320,419 | q31 | Loss | 16,848 | 51.5 | 1.3 | 50.2 | 5.38E−10 | 8.10E−09 | DHCR24 |
| chr5: 54,320,419-54,413,010 | q31 | Loss | 92,591 | 54.5 | 1.3 | 53.2 | 9.97E−11 | 1.85E−09 | DHCR24, C5H1orf177, TTC22, PARS2, TTC4 |
| chr5: 54,413,010-54,610,336 | q31 | Loss | 197,326 | 57.6 | 1.3 | 56.3 | 1.75E−11 | 4.38E−10 | TTC4, HEATR8, FAM151A, ACOT11 |
| chr5: 54,610,336-54,767,411 | q31 | Loss | 157,075 | 60.6 | 2.6 | 58.0 | 2.72E−11 | 6.21E−10 | LOC102151468, LOC102151517, SSBP3 |
| chr5: 55,243,189-55,254,977 | q31 | Loss | 11,788 | 63.6 | 2.6 | 61.0 | 4.45E−12 | 1.48E−10 | GLIS1 |
| chr5: 55,254,977-55,454,968 | q31 | Loss | 199,991 | 63.6 | 3.9 | 59.7 | 3.09E−11 | 6.77E−10 | GLIS1 |
| chr5: 55,454,968-55,654,428 | q31-q32 | Loss | 199,460 | 63.6 | 2.6 | 61.0 | 4.45E−12 | 1.48E−10 | GLIS1, DMRTB1, C8A, LRP8 |
| chr5: 55,654,428-55,724,923 | q32 | Loss | 70,495 | 60.6 | 1.3 | 59.3 | 2.88E−12 | 1.11E−10 | LRP8, MAGOH, C5H1orf123, CPT2 |
| chr5: 55,724,923-55,840,582 | q32 | Loss | 115,659 | 63.6 | 1.3 | 62.3 | 4.46E−13 | 3.02E−11 | CPT2, LOC102153558, SLC1A7, PODN |
| chr5: 55,840,582-55,916,484 | q32 | Loss | 75,902 | 60.6 | 1.3 | 59.3 | 2.88E−12 | 1.11E−10 | PODN, LOC102153929, SCP2 |
| chr5: 55,916,484-55,992,635 | q32 | Loss | 76,151 | 66.7 | 1.3 | 65.4 | 6.42E−14 | 9.66E−12 | LOC102153929, SCP2, ECHDC2 |
| chr5: 55,992,635-56,081,540 | q32 | Loss | 88,905 | 63.6 | 1.3 | 62.3 | 4.46E−13 | 3.02E−11 | ZYG11A |
| chr5: 56,081,540-56,131,102 | q32 | Loss | 49,562 | 60.6 | 1.3 | 59.3 | 2.88E−12 | 1.11E−10 | SAMD11 |
| chr5: 56,533,402-56,539,243 | q32 | Loss | 5,841 | 51.5 | 1.3 | 50.2 | 5.38E−10 | 8.10E−09 | |
| chr5: 56,539,243-56,713,902 | q32 | Loss | 174,659 | 54.5 | 1.3 | 53.2 | 9.97E−11 | 1.85E−09 | AURKAIP1, CCNL2, MRPL20, ANKRD65, TMEM88B, VWA1, ATAD3B, TMEM240, SSU72, C5H1orf233, MIB2, MMP23B, CDK11B |
| chr5: 56,713,902-56,760,282 | q32 | Loss | 46,380 | 51.5 | 1.3 | 50.2 | 5.38E−10 | 8.10E−09 | CDK11B, SLC35E2B, NADK |
| chr5: 56,800,229-56,812,468 | q32 | Loss | 12,239 | 54.5 | 1.3 | 53.2 | 9.97E−11 | 1.85E−09 | GNB1 |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| chr5: 56,812,468-56,835,624 | q32 | Loss | 23,156 | 57.6 | 1.3 | 56.3 | 1.75E-11 | 4.38E-10 | GNB1 |
| chr5: 56,835,624-56,859,924 | q32 | Loss | 24,300 | 54.5 | 1.3 | 53.2 | 9.97E-11 | 1.85E-09 | GNB1 |
| chr5: 56,879,215-56,892,317 | q32 | Loss | 13,102 | 51.5 | 1.3 | 50.2 | 5.38E-10 | 8.10E-09 | GNB1 |
| chr5: 57,333,494-57,373,774 | q32 | Loss | 40,280 | 54.5 | 3.9 | 50.6 | 4.94E-09 | 5.94E-08 | PLCH2, PANK4 |
| chr5: 57,373,774-57,397,914 | q32 | Loss | 24,140 | 57.6 | 3.9 | 53.6 | 9.72E-10 | 1.34E-08 | PANK4, HES5, LOC102155829 |
| chr5: 57,397,914-57,427,153 | q32 | Loss | 29,239 | 60.6 | 3.9 | 56.7 | 1.79E-10 | 2.97E-09 | LOC102155829, TNFRSF14 |
| chr5: 57,427,153-57,441,148 | q32 | Loss | 13,995 | 60.6 | 6.6 | 54.0 | 3.94E-09 | 4.98E-08 | FAM213B, MMEL1 |
| chr5: 57,441,148-57,473,452 | q32 | Loss | 32,304 | 63.6 | 6.6 | 57.1 | 7.51E-10 | 1.12E-08 | MMEL1, LOC479559 |
| chr5: 57,473,452-57,551,025 | q32 | Loss | 77,573 | 63.6 | 7.9 | 55.7 | 2.91E-09 | 3.74E-08 | LOC479559, TTC34 |
| chr5: 57,551,025-57,607,976 | q32 | Loss | 56,951 | 63.6 | 9.2 | 54.4 | 1.00E-08 | 1.18E-07 | |
| chr5: 57,607,976-57,621,918 | q32 | Loss | 13,942 | 63.6 | 10.5 | 53.1 | 3.13E-08 | 3.41E-07 | |
| chr5: 57,621,918-57,686,792 | q32 | Loss | 64,874 | 69.7 | 10.5 | 59.2 | 1.18E-09 | 1.59E-08 | ACTRT2 |
| chr5: 57,686,792-57,792,964 | q32 | Loss | 106,172 | 69.7 | 15.8 | 53.9 | 7.35E-08 | 7.77E-07 | LOC102156624 |
| chr5: 57,792,964-57,810,561 | q32 | Loss | 17,597 | 69.7 | 18.4 | 51.3 | 4.48E-07 | 4.42E-06 | LOC102156763, PRDM16 |
| chr5: 57,810,561-57,835,337 | q32 | Loss | 9,505 | 72.7 | 19.7 | 53.0 | 2.14E-07 | 2.19E-06 | PRDM16 |
| chr5: 57,844,842-57,946,330 | q32 | Loss | 101,488 | 72.7 | 22.4 | 50.4 | 1.06E-06 | 1.04E-05 | PRDM16 |
| chr5: 58,119,121-58,237,076 | q32 | Loss | 117,955 | 63.6 | 13.2 | 50.5 | 2.37E-07 | 2.43E-06 | MEGF6, TPRG1L, WRAP73, TP73 |
| chr5: 58,237,076-58,255,637 | q32 | Loss | 18,561 | 63.6 | 3.9 | 59.7 | 3.09E-11 | 6.77E-10 | TP73 |
| chr5: 58,255,637-58,708,022 | q32 | Loss | 452,385 | 60.6 | 3.9 | 56.7 | 1.79E-10 | 2.97E-09 | CCDC27, SMIM1, LRRC47, CEP104, DFFB, C5H1orf174, LOC102151771 |
| chr5: 58,708,022-58,727,983 | q32 | Loss | 19,961 | 66.7 | 5.3 | 61.4 | 2.81E-11 | 6.38E-10 | LOC102151822, LOC102151862 |
| chr5: 58,727,983-58,911,333 | q32 | Loss | 183,350 | 69.7 | 9.2 | 60.5 | 3.47E-10 | 5.61E-09 | AJAP1 |
| chr5: 58,911,333-59,057,612 | q32 | Loss | 146,279 | 69.7 | 5.3 | 64.4 | 4.36E-12 | 1.48E-10 | AJAP1 |
| chr5: 59,057,612-59,113,878 | q32 | Loss | 56,266 | 66.7 | 3.9 | 62.7 | 4.94E-12 | 1.59E-10 | |
| chr5: 59,113,878-59,187,182 | q32 | Loss | 73,304 | 63.6 | 3.9 | 59.7 | 3.09E-11 | 6.77E-10 | |
| chr5: 59,187,182-59,326,374 | q32 | Loss | 139,192 | 60.6 | 3.9 | 56.7 | 1.79E-10 | 2.97E-09 | ISG15 |
| chr5: 59,326,374-59,781,603 | q32 | Loss | 455,229 | 63.6 | 3.9 | 59.7 | 3.09E-11 | 6.77E-10 | PUSL1, CPSF3L, GLTPD1, DVL1 |
| chr5: 59,781,603-59,794,743 | q32 | Loss | 13,140 | 63.6 | 5.3 | 58.4 | 1.67E-10 | 2.84E-09 | |
| chr5: 59,794,743-59,805,785 | q32 | Loss | 11,042 | 63.6 | 6.6 | 57.1 | 7.51E-10 | 1.12E-08 | |
| chr5: 59,805,785-59,836,239 | q32 | Loss | 30,454 | 57.6 | 6.6 | 51.0 | 1.92E-08 | 2.15E-07 | NPHP4 |
| chr5: 60,170,663-60,180,879 | q32 | Loss | 10,216 | 54.5 | 3.9 | 50.6 | 4.94E-09 | 5.94E-08 | ACOT7 |
| chr5: 60,180,879-60,354,077 | q32 | Loss | 173,198 | 57.6 | 3.9 | 53.6 | 9.72E-10 | 1.34E-08 | ACOT7, HES2, PEX10, ESPN, TNFRSF25, PLEKHG5 |
| chr5: 60,354,077-60,427,986 | q32 | Loss | 73,909 | 69.7 | 3.9 | 65.7 | 7.29E-13 | 4.00E-11 | NOL9, TAS1R1, ZBTB48, KLHL21 |
| chr5: 60,427,986-60,508,241 | q32 | Loss | 80,255 | 69.7 | 1.3 | 68.4 | 8.56E-15 | 3.54E-12 | PHF13, THAP3, DNAJC11 |
| chr5: 60,508,241-60,541,238 | q32 | Loss | 32,997 | 66.7 | 1.3 | 65.4 | 6.42E-14 | 9.66E-12 | DNAJC11, LOC102154443 |
| chr5: 60,541,238-60,684,920 | q32 | Loss | 143,682 | 63.6 | 1.3 | 62.3 | 4.46E-13 | 3.02E-11 | LOC102154443, CAMTA1 |
| chr5: 60,684,920-60,852,161 | q32 | Loss | 167,241 | 69.7 | 2.6 | 67.1 | 9.50E-14 | 1.12E-11 | CAMTA1 |
| chr5: 60,852,161-61,036,261 | q32 | Loss | 184,100 | 66.7 | 2.6 | 64.0 | 6.76E-13 | 3.91E-11 | CAMTA1 |
| chr5: 61,036,261-61,044,908 | q32 | Loss | 8,647 | 66.7 | 3.9 | 62.7 | 4.94E-12 | 1.59E-10 | CAMTA1 |
| chr5: 61,044,908-61,141,116 | q32-q33 | Loss | 96,208 | 72.7 | 6.6 | 66.1 | 3.20E-12 | 1.22E-10 | CAMTA1 |
| chr5: 61,141,116-61,316,581 | q33 | Loss | 175,465 | 75.8 | 11.8 | 63.9 | 1.05E-10 | 1.93E-09 | CAMTA1, LOC607748 |
| chr5: 61,316,581-61,329,461 | q33 | Loss | 12,880 | 66.7 | 6.6 | 60.1 | 1.33E-10 | 2.43E-09 | CAMTA1 |
| chr5: 61,329,461-61,367,490 | q33 | Loss | 38,029 | 63.6 | 6.6 | 57.1 | 7.51E-10 | 1.12E-08 | CAMTA1 |
| chr5: 61,367,490-61,378,222 | q33 | Loss | 10,732 | 57.6 | 6.6 | 51.0 | 1.92E-08 | 2.15E-07 | CAMTA1 |
| chr5: 61,378,222-61,394,755 | q33 | Loss | 16,533 | 54.5 | 3.9 | 50.6 | 4.94E-09 | 5.94E-08 | CAMTA1 |
| chr5: 61,394,755-61,402,826 | q33 | Loss | 8,071 | 54.5 | 1.3 | 53.2 | 9.97E-11 | 1.85E-09 | CAMTA1 |
| chr5: 61,812,024-61,901,869 | q33 | Loss | 89,845 | 51.5 | 1.3 | 50.2 | 5.38E-10 | 8.10E-09 | SLC45A1, RERE |
| chr5: 62,305,554-62,381,943 | q33 | Loss | 76,389 | 51.5 | 1.3 | 50.2 | 5.38E-10 | 8.10E-09 | ENO1, CA6 |
| chr5: 62,381,943-62,555,678 | q33 | Loss | 173,735 | 54.5 | 1.3 | 53.2 | 9.97E-11 | 1.85E-09 | SLC2A5, GPR157, H6PD |
| chr5: 62,555,678-62,785,659 | q33 | Loss | 229,981 | 57.6 | 1.3 | 56.3 | 1.75E-11 | 4.38E-10 | H6PD, SPSB1 |
| chr5: 62,785,659-63,063,012 | q33 | Loss | 277,353 | 54.5 | 1.3 | 53.2 | 9.97E-11 | 1.85E-09 | SLC25A33, TMEM201, PIK3CD, CLSTN1, CTNNB1P1 |
| chr5: 63,063,012-63,103,582 | q33 | Loss | 40,570 | 57.6 | 1.3 | 56.3 | 1.75E-11 | 4.38E-10 | CTNNB1P1 |
| chr5: 63,103,582-63,125,693 | q33 | Loss | 22,111 | 60.6 | 1.3 | 59.3 | 2.88E-12 | 1.11E-10 | LZIC, NMNAT1 |
| chr5: 63,125,693-63,258,956 | q33 | Loss | 133,263 | 66.7 | 1.3 | 65.4 | 6.42E-14 | 9.66E-12 | NMNAT1, RBP7, UBE4B |
| chr5: 63,258,956-63,349,218 | q33 | Loss | 90,262 | 63.6 | 1.3 | 62.3 | 4.46E-13 | 3.02E-11 | UBE4B, LOC102153284 |
| chr5: 63,349,218-63,514,128 | q33 | Loss | 164,910 | 57.6 | 1.3 | 56.3 | 1.75E-11 | 4.38E-10 | KIF1B |
| chr5: 63,514,128-63,617,392 | q33 | Loss | 103,264 | 63.6 | 1.3 | 62.3 | 4.46E-13 | 3.02E-11 | KIF1B, LOC100682843, LOC489647, GAS8, DBNDD1 |
| chr5: 63,617,392-63,679,390 | q33 | Loss | 61,998 | 60.6 | 1.3 | 59.3 | 2.88E-12 | 1.11E-10 | DBNDD1, LOC102155075, CENPBD1, DEF8 |
| chr5: 63,679,390-63,712,820 | q33 | Loss | 33,430 | 57.6 | 1.3 | 56.3 | 1.75E-11 | 4.38E-10 | TUBB3, MC1R, TCF25 |
| chr5: 63,712,820-63,882,807 | q33 | Loss | 169,987 | 54.5 | 1.3 | 53.2 | 9.97E-11 | 1.85E-09 | TCF25, SPIRE2, FANCA, ZNF276, VPS9D1, SPATA2L, CDK10 |
| chr5: 63,882,807-64,185,061 | q33 | Loss | 302,254 | 57.6 | 1.3 | 56.3 | 1.75E-11 | 4.38E-10 | CDK10, SPATA33, CHMP1A, DPEP1, LOC102155777, CPNE7, RPL13, SPG7, ANKRD11 |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| chr5: 64,185,061-64,198,235 | q33 | Loss | 13,174 | 57.6 | 2.6 | 54.9 | 1.56E-10 | 2.67E-09 | ANKRD11 |
| chr5: 64,198,235-64,262,537 | q33 | Loss | 64,302 | 57.6 | 3.9 | 53.6 | 9.72E-10 | 1.34E-08 | ANKRD11, SLC22A31, CDH15 |
| chr5: 64,262,537-64,399,872 | q33 | Loss | 137,335 | 60.6 | 3.9 | 56.7 | 1.79E-10 | 2.97E-09 | CDH15, ACSF3, CAMTA1 |
| chr5: 64,399,872-64,419,690 | q33 | Loss | 19,818 | 57.6 | 3.9 | 53.6 | 9.72E-10 | 1.34E-08 | CAMTA1 |
| chr5: 64,712,902-64,810,771 | q33 | Loss | 97,869 | 60.6 | 6.6 | 54.0 | 3.94E-09 | 4.98E-08 | ZC3H18 |
| chr5: 64,810,771-64,855,695 | q33 | Loss | 44,924 | 60.6 | 5.3 | 55.3 | 9.21E-10 | 1.29E-08 | ZFPM1 |
| chr5: 64,855,695-64,939,536 | q33 | Loss | 83,841 | 63.6 | 6.6 | 57.1 | 7.51E-10 | 1.12E-08 | ZFPM1, ZNF469 |
| chr5: 64,939,536-65,041,471 | q33 | Loss | 101,935 | 66.7 | 7.9 | 58.8 | 5.39E-10 | 8.10E-09 | |
| chr5: 65,041,471-65,142,070 | q33 | Loss | 100,599 | 66.7 | 6.6 | 60.1 | 1.33E-10 | 2.43E-09 | |
| chr5: 65,142,070-65,190,048 | q33 | Loss | 47,978 | 63.6 | 2.6 | 61.0 | 4.45E-12 | 1.48E-10 | BANP |
| chr5: 65,190,048-65,203,750 | q33 | Loss | 13,702 | 60.6 | 2.6 | 58.0 | 2.72E-11 | 6.21E-10 | BANP |
| chr5: 65,203,750-65,420,725 | q33 | Loss | 216,975 | 57.6 | 2.6 | 54.9 | 1.56E-10 | 2.67E-09 | BANP, CA5A, SLC7A5, KLHDC4 |
| chr5: 65,420,725-65,513,651 | q33 | Loss | 92,926 | 60.6 | 2.6 | 58.0 | 2.72E-11 | 6.21E-10 | KLHDC4, JPH3 |
| chr5: 65,513,651-65,596,667 | q33 | Loss | 83,016 | 60.6 | 1.3 | 59.3 | 2.88E-12 | 1.11E-10 | JPH3 |
| chr5: 65,596,667-65,928,870 | q33 | Loss | 332,203 | 63.6 | 1.3 | 62.3 | 4.46E-13 | 3.02E-11 | LOC102152720, ZCCHC14, MAP1LC3B, FBXO31, LOC609239, LOC102153014 |
| chr5: 65,928,870-66,430,556 | q33 | Loss | 501,686 | 63.6 | 2.6 | 61.0 | 4.45E-12 | 1.48E-10 | LOC102153014, LZIC, NMNAT1, LOC102153168, LOC102153219, FOXL1, FOXC2, LOC102153392, MTHFSD, FOXF1, LOC102153633 |
| chr5: 66,430,556-66,532,101 | q33 | Loss | 101,545 | 60.6 | 2.6 | 58.0 | 2.72E-11 | 6.21E-10 | |
| chr5: 66,532,101-66,660,467 | q33 | Loss | 128,366 | 57.6 | 2.6 | 54.9 | 1.56E-10 | 2.67E-09 | |
| chr5: 66,660,467-66,940,063 | q33 | Loss | 279,596 | 57.6 | 1.3 | 56.3 | 1.75E-11 | 4.38E-10 | TUBB3, SPIRE2, IRF8, LOC489654, COX4I1, EMC8 |
| chr5: 66,940,063-66,978,728 | q33 | Loss | 38,665 | 54.5 | 1.3 | 53.2 | 9.97E-11 | 1.85E-09 | C5H16orf74 |
| chr5: 66,978,728-67,024,605 | q33 | Loss | 45,877 | 60.6 | 6.6 | 54.0 | 3.94E-09 | 4.98E-08 | GINS2, KIAA0182 |
| chr5: 67,024,605-67,107,364 | q33 | Loss | 82,759 | 60.6 | 7.9 | 52.7 | 1.46E-08 | 1.64E-07 | KIAA0182 |
| chr5: 67,107,364-67,134,097 | q33 | Loss | 26,733 | 60.6 | 5.3 | 55.3 | 9.21E-10 | 1.29E-08 | KIAA0182 |
| chr5: 67,134,097-67,358,286 | q33 | Loss | 224,189 | 54.5 | 3.9 | 50.6 | 4.94E-09 | 5.94E-08 | KIAA0182 |
| chr5: 67,358,286-67,376,754 | q33 | Loss | 18,468 | 54.5 | 2.6 | 51.9 | 8.40E-10 | 1.18E-08 | |
| chr5: 67,464,481-67,505,212 | q33 | Loss | 40,731 | 57.6 | 2.6 | 54.9 | 1.56E-10 | 2.67E-09 | FAM92B, KIAA0513 |
| chr5: 67,505,212-67,694,200 | q33 | Loss | 188,988 | 60.6 | 2.6 | 58.0 | 2.72E-11 | 6.21E-10 | KIAA0513, ZDHHC7, CRISPLD2 |
| chr5: 67,694,200-68,175,856 | q33 | Loss | 481,656 | 57.6 | 1.3 | 56.3 | 1.75E-11 | 4.38E-10 | CRISPLD2, USP10, KLHL36, COTL1, LOC102152359, TLDC1, ATP2C2, LOC102152587, WFDC1, KCNG4, ADAD2, TAF1C |
| chr5: 68,175,856-68,238,327 | q33 | Loss | 62,471 | 60.6 | 1.3 | 59.3 | 2.88E-12 | 1.11E-10 | TAF1C, DNAAF1, HSDL1, MBTPS1 |
| chr5: 68,238,327-68,254,252 | q33 | Loss | 15,925 | 63.6 | 1.3 | 62.3 | 4.46E-13 | 3.02E-11 | MBTPS1 |
| chr5: 68,254,252-68,321,004 | q33 | Loss | 66,752 | 69.7 | 6.6 | 63.1 | 2.16E-11 | 5.35E-10 | MBTPS1, SLC38A8, NECAB2 |
| chr5: 68,321,004-68,330,658 | q33 | Loss | 9,654 | 66.7 | 3.9 | 62.7 | 4.94E-12 | 1.59E-10 | NECAB2 |
| chr5: 68,330,658-68,354,363 | q33 | Loss | 23,705 | 57.6 | 3.9 | 53.6 | 9.72E-10 | 1.34E-08 | NECAB2, OSGIN1 |
| chr5: 68,354,363-68,452,845 | q33 | Loss | 98,482 | 57.6 | 1.3 | 56.3 | 1.75E-11 | 4.38E-10 | OSGIN1, MLYCD |
| chr5: 68,452,845-68,492,076 | q33 | Loss | 39,231 | 66.7 | 1.3 | 65.4 | 6.42E-14 | 9.66E-12 | HSBP1 |
| chr5: 68,492,076-68,596,350 | q33 | Loss | 104,274 | 69.7 | 1.3 | 68.4 | 8.56E-15 | 3.54E-12 | CDH13 |
| chr5: 68,596,350-68,755,793 | q33 | Loss | 159,443 | 60.6 | 1.3 | 59.3 | 2.88E-12 | 1.11E-10 | CDH13 |
| chr5: 68,755,793-68,929,916 | q33 | Loss | 174,123 | 57.6 | 1.3 | 56.3 | 1.75E-11 | 4.38E-10 | CDH13 |
| chr5: 68,929,916-69,299,668 | q33 | Loss | 369,752 | 54.5 | 1.3 | 53.2 | 9.97E-11 | 1.85E-09 | CDH13, LOC102153763 |
| chr5: 69,299,668-69,397,643 | q33-q34 | Loss | 97,975 | 57.6 | 1.3 | 56.3 | 1.75E-11 | 4.38E-10 | CDH13 |
| chr5: 69,397,643-69,460,633 | q34 | Loss | 62,990 | 60.6 | 1.3 | 59.3 | 2.88E-12 | 1.11E-10 | CDH13 |
| chr5: 69,460,633-69,727,892 | q34 | Loss | 267,259 | 63.6 | 1.3 | 62.3 | 4.46E-13 | 3.02E-11 | CDH13 |
| chr5: 69,727,892-69,811,895 | q34 | Loss | 84,003 | 60.6 | 1.3 | 59.3 | 2.88E-12 | 1.11E-10 | LOC102153888 |
| chr5: 69,811,895-69,912,645 | q34 | Loss | 100,750 | 63.6 | 1.3 | 62.3 | 4.46E-13 | 3.02E-11 | LOC102153888, LOC100686562, LOC102154063, MPHOSPH6 |
| chr5: 69,912,645-69,976,616 | q34 | Loss | 63,971 | 66.7 | 1.3 | 65.4 | 6.42E-14 | 9.66E-12 | HSD17B2 |
| chr5: 69,976,616-70,048,532 | q34 | Loss | 71,916 | 63.6 | 1.3 | 62.3 | 4.46E-13 | 3.02E-11 | HSD17B2, SDR42E1 |
| chr5: 70,048,532-70,118,809 | q34 | Loss | 70,277 | 60.6 | 1.3 | 59.3 | 2.88E-12 | 1.11E-10 | PLCG2 |
| chr5: 70,118,809-70,256,802 | q34 | Loss | 137,993 | 51.5 | 1.3 | 50.2 | 5.38E-10 | 8.10E-09 | PLCG2, LOC102154738, CMIP |
| chr5: 70,256,802-70,325,943 | q34 | Loss | 69,141 | 57.6 | 1.3 | 56.3 | 1.75E-11 | 4.38E-10 | CMIP |
| chr5: 70,325,943-70,419,585 | q34 | Loss | 93,642 | 54.5 | 1.3 | 53.2 | 9.97E-11 | 1.85E-09 | CMIP |
| chr5: 70,419,585-70,516,517 | q34 | Loss | 96,932 | 51.5 | 1.3 | 50.2 | 5.38E-10 | 8.10E-09 | LOC102154784 |
| chr5: 70,561,384-71,093,340 | q34 | Loss | 531,956 | 51.5 | 1.3 | 50.2 | 5.38E-10 | 8.10E-09 | GAN, LOC102154971, BCMO1, PKD1L2, GCSH, C5H16orf46, ATMIN, CENPN, CMC2, CDYL2 |
| chr5: 71,093,340-71,434,076 | q34 | Loss | 340,736 | 54.5 | 1.3 | 53.2 | 9.97E-11 | 1.85E-09 | CDYL2, DYNLRB2, LOC102156069 |
| chr5: 71,434,076-71,693,390 | q34 | Loss | 259,314 | 51.5 | 1.3 | 50.2 | 5.38E-10 | 8.10E-09 | LOC102156069, LOC102156020, HSBP1 |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| chr5: 72,431,034-72,750,582 | q34 | Loss | 319,548 | 54.5 | 1.3 | 53.2 | 9.97E-11 | 1.85E-09 | WWOX |
| chr5: 72,750,582-72,808,838 | q34 | Loss | 58,256 | 51.5 | 1.3 | 50.2 | 5.38E-10 | 8.10E-09 | WWOX |
| chr5: 73,342,822-73,464,745 | q34 | Loss | 121,923 | 54.5 | 1.3 | 53.2 | 9.97E-11 | 1.85E-09 | VAT1L |
| chr5: 73,464,745-73,541,058 | q34 | Loss | 76,313 | 57.6 | 1.3 | 56.3 | 1.75E-11 | 4.38E-10 | VAT1L, NUDT7 |
| chr5: 73,541,058-73,686,949 | q34 | Loss | 145,891 | 54.5 | 1.3 | 53.2 | 9.97E-11 | 1.85E-09 | |
| chr5: 73,686,949-73,843,644 | q34 | Loss | 156,695 | 57.6 | 1.3 | 56.3 | 1.75E-11 | 4.38E-10 | ADAMTS18 |
| chr5: 73,843,644-73,896,791 | q34 | Loss | 53,147 | 54.5 | 1.3 | 53.2 | 9.97E-11 | 1.85E-09 | ADAMTS18 |
| chr5: 74,982,757-75,025,354 | q34 | Loss | 42,597 | 54.5 | 1.3 | 53.2 | 9.97E-11 | 1.85E-09 | |
| chr5: 75,025,354-75,234,343 | q34 | Loss | 208,989 | 57.6 | 1.3 | 56.3 | 1.75E-11 | 4.38E-10 | TERF2IP, KARS, ADAT1, GABARAPL2 |
| chr5: 75,234,343-75,248,653 | q34 | Loss | 14,310 | 54.5 | 1.3 | 53.2 | 9.97E-11 | 1.85E-09 | ADAT1, GABARAPL2, TMEM231 |
| chr5: 75,248,653-75,398,797 | q34 | Loss | 150,144 | 51.5 | 1.3 | 50.2 | 5.38E-10 | 8.10E-09 | TMEM231, CHST6, TMEM170A, CFDP1 |
| chr5: 75,398,797-75,540,382 | q34 | Loss | 141,585 | 57.6 | 1.3 | 56.3 | 1.75E-11 | 4.38E-10 | CFDP1, BCAR1, LOC610373, LOC479649, CTRB2 |
| chr5: 75,540,382-75,641,073 | q34 | Loss | 100,691 | 51.5 | 1.3 | 50.2 | 5.38E-10 | 8.10E-09 | ZFP1, LDHD, ZNRF1 |
| chr5: 75,641,073-75,717,063 | q34 | Loss | 75,990 | 54.5 | 1.3 | 53.2 | 9.97E-11 | 1.85E-09 | ZNRF1, WDR59 |
| chr5: 75,717,063-76,023,587 | q34 | Loss | 306,524 | 63.6 | 1.3 | 62.3 | 4.46E-13 | 3.02E-11 | WDR59, FA2H, RFWD3, GLG1 |
| chr5: 76,023,587-76,053,502 | q34 | Loss | 29,915 | 60.6 | 1.3 | 59.3 | 2.88E-12 | 1.11E-10 | GLG1 |
| chr5: 76,053,502-76,096,004 | q34 | Loss | 42,502 | 57.6 | 1.3 | 56.3 | 1.75E-11 | 4.38E-10 | GLG1 |
| chr5: 76,096,004-76,152,809 | q34 | Loss | 56,805 | 54.5 | 1.3 | 53.2 | 9.97E-11 | 1.85E-09 | GLG1 |
| chr5: 76,152,809-76,280,694 | q34 | Loss | 127,885 | 57.6 | 1.3 | 56.3 | 1.75E-11 | 4.38E-10 | GLG1, LOC100688256, PDPR, CLEC18A, LOC610465 |
| chr5: 76,280,694-76,401,056 | q34 | Loss | 120,362 | 54.5 | 1.3 | 53.2 | 9.97E-11 | 1.85E-09 | LOC610465, EXOSC6, AARS, DDX19B, LOC102154605, DDX19A, ST3GAL2 |
| chr5: 76,401,056-76,426,024 | q34 | Loss | 24,968 | 60.6 | 1.3 | 59.3 | 2.88E-12 | 1.11E-10 | ST3GAL2 |
| chr5: 76,426,024-76,480,400 | q34 | Loss | 54,376 | 63.6 | 1.3 | 62.3 | 4.46E-13 | 3.02E-11 | ST3GAL2, FUK, COG4 |
| chr5: 76,480,400-76,509,943 | q34 | Loss | 29,543 | 66.7 | 1.3 | 65.4 | 6.42E-14 | 9.66E-12 | COG4, SF3B3 |
| chr5: 76,509,943-76,722,201 | q34 | Loss | 212,258 | 69.7 | 1.3 | 68.4 | 8.56E-15 | 3.54E-12 | SF3B3, IL34, MTSS1L, VAC14 |
| chr5: 76,722,201-76,779,204 | q34 | Loss | 57,003 | 66.7 | 1.3 | 65.4 | 6.42E-14 | 9.66E-12 | VAC14, HYDIN |
| chr5: 76,779,204-76,903,015 | q34 | Loss | 123,811 | 63.6 | 1.3 | 62.3 | 4.46E-13 | 3.02E-11 | HYDIN |
| chr5: 76,903,015-77,112,947 | q34 | Loss | 209,932 | 57.6 | 1.3 | 56.3 | 1.75E-11 | 4.38E-10 | HYDIN, LOC102156275 |
| chr5: 77,112,947-77,205,471 | q34 | Loss | 92,524 | 60.6 | 1.3 | 59.3 | 2.88E-12 | 1.11E-10 | CMTR2, LOC102156521, CALB2 |
| chr5: 77,205,471-77,241,951 | q34 | Loss | 36,480 | 57.6 | 1.3 | 56.3 | 1.75E-11 | 4.38E-10 | LOC479662 |
| chr5: 77,241,951-77,306,877 | q34 | Loss | 64,926 | 51.5 | 1.3 | 50.2 | 5.38E-10 | 8.10E-09 | LOC479662, ZNF23, ZNF19 |
| chr5: 77,520,487-77,574,687 | q34 | Loss | 54,200 | 51.5 | 1.3 | 50.2 | 5.38E-10 | 8.10E-09 | AP1G1 |
| chr5: 77,574,687-77,619,106 | q34-q35 | Loss | 44,419 | 54.5 | 1.3 | 53.2 | 9.97E-11 | 1.85E-09 | AP1G1, ATXN1L |
| chr5: 77,619,106-77,799,802 | q35 | Loss | 180,696 | 57.6 | 1.3 | 56.3 | 1.75E-11 | 4.38E-10 | ATXN1L, ZNF821, IST1, PKD1L3, DHODH, LOC612963, LOC479668 |
| chr5: 77,799,802-77,820,747 | q35 | Loss | 20,945 | 54.5 | 1.3 | 53.2 | 9.97E-11 | 1.85E-09 | LOC612963, LOC479668, DHX38 |
| chr5: 77,820,747-78,019,912 | q35 | Loss | 199,165 | 51.5 | 1.3 | 50.2 | 5.38E-10 | 8.10E-09 | DHX38, PMFBP1 |
| chr5: 78,019,912-78,134,883 | q35 | Loss | 114,971 | 54.5 | 1.3 | 53.2 | 9.97E-11 | 1.85E-09 | |
| chr5: 78,459,732-78,473,806 | q35 | Loss | 14,074 | 63.6 | 1.3 | 62.3 | 4.46E-13 | 3.02E-11 | ZFHX3 |
| chr5: 78,473,806-78,600,625 | q35 | Loss | 126,819 | 66.7 | 1.3 | 65.4 | 6.42E-14 | 9.66E-12 | ZFHX3 |
| chr5: 78,600,625-78,710,020 | q35 | Loss | 109,395 | 63.6 | 1.3 | 62.3 | 4.46E-13 | 3.02E-11 | ZFHX3 |
| chr5: 78,710,020-78,909,765 | q35 | Loss | 199,745 | 57.6 | 1.3 | 56.3 | 1.75E-11 | 4.38E-10 | ZFHX3, LOC102153471 |
| chr5: 78,909,765-79,145,756 | q35 | Loss | 235,991 | 54.5 | 1.3 | 53.2 | 9.97E-11 | 1.85E-09 | LOC102153471 |
| chr5: 79,145,756-79,179,389 | q35 | Loss | 33,633 | 51.5 | 1.3 | 50.2 | 5.38E-10 | 8.10E-09 | |
| chr5: 80,595,921-80,616,230 | q35 | Loss | 20,309 | 51.5 | 0.0 | 51.5 | 3.58E-11 | 7.73E-10 | TANGO6 |
| chr5: 80,616,230-80,765,577 | q35 | Loss | 149,347 | 51.5 | 1.3 | 50.2 | 5.38E-10 | 8.10E-09 | TANGO6, CDH1 |
| chr5: 80,765,577-80,799,104 | q35 | Loss | 33,527 | 54.5 | 1.3 | 53.2 | 9.97E-11 | 1.85E-09 | CDH1 |
| chr5: 80,799,104-80,804,686 | q35 | Loss | 5,582 | 57.6 | 1.3 | 56.3 | 1.75E-11 | 4.38E-10 | CDH1 |
| chr5: 80,804,686-80,914,064 | q35 | Loss | 109,378 | 66.7 | 1.3 | 65.4 | 6.42E-14 | 9.66E-12 | CDH1, CDH3, ZFP90 |
| chr5: 80,914,064-81,187,351 | q35 | Loss | 273,287 | 63.6 | 1.3 | 62.3 | 4.46E-13 | 3.02E-11 | ZFP90, SMPD3, PRMT7 |
| chr5: 81,187,351-81,255,412 | q35 | Loss | 68,061 | 57.6 | 1.3 | 56.3 | 1.75E-11 | 4.38E-10 | PRMT7, SLC7A6OS, SLC7A6 |
| chr5: 81,569,146-81,577,803 | q35 | Loss | 8,657 | 51.5 | 1.3 | 50.2 | 5.38E-10 | 8.10E-09 | PSKH1 |
| chr5: 81,577,803-81,609,089 | q35 | Loss | 31,286 | 54.5 | 1.3 | 53.2 | 9.97E-11 | 1.85E-09 | PSKH1, NRN1L, EDC4 |
| chr5: 81,609,089-81,680,133 | q35 | Loss | 71,044 | 57.6 | 1.3 | 56.3 | 1.75E-11 | 4.38E-10 | EDC4, NUTF2, THAP11, CENPT, TSNAXIP1, RANBP10 |
| chr5: 81,680,133-81,863,442 | q35 | Loss | 183,309 | 60.6 | 1.3 | 59.3 | 2.88E-12 | 1.11E-10 | RANBP10, GFOD2, C5H16orf86, ENKD1, PARD6A, ACD, RLTPR, CTCF |
| chr5: 81,863,442-82,011,077 | q35 | Loss | 147,635 | 57.6 | 1.3 | 56.3 | 1.75E-11 | 4.38E-10 | CTCF, FAM65A, AGRP, ATP6V0D1, HSD11B2, ZDHHC1, TPPP3, LRRC36 |
| chr5: 82,011,077-82,282,553 | q35 | Loss | 271,476 | 54.5 | 1.3 | 53.2 | 9.97E-11 | 1.85E-09 | TPPP3, LRRC36, KCTD19, PLEKHG4, SLC9A5, FHOD1, TMEM208, LRRC29, LOC102155969, ELMO3, E2F4, EXOC3L1, KIAA0895L, NOL3, |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| chr5: 82,282,553-82,519,611 | q35 | Loss | 237,058 | 57.6 | 1.3 | 56.3 | 1.75E−11 | 4.38E−10 | HSF4, FBXL8, TRADD, B3GNT9, C5H16orf70, CBFB CBFB, CES2, FAM96B, RRAD, CDH16, PDP2, CA7, NAE1, CCDC79 |
| chr5: 82,519,611-82,616,288 | q35 | Loss | 96,677 | 54.5 | 1.3 | 53.2 | 9.97E−11 | 1.85E−09 | CCDC79, DYNC1LI2 |
| chr5: 82,616,288-82,766,028 | q35 | Loss | 149,740 | 57.6 | 1.3 | 56.3 | 1.75E−11 | 4.38E−10 | CMTM4, CMTM3, LOC479694, CMTM1, CKLF, TK2 |
| chr5: 82,766,028-82,782,187 | q35 | Loss | 16,159 | 57.6 | 5.3 | 52.3 | 4.74E−09 | 5.74E−08 | BEAN1 |
| chr5: 82,782,187-82,798,102 | q35 | Loss | 15,915 | 60.6 | 5.3 | 55.3 | 9.21E−10 | 1.29E−08 | BEAN1 |
| chr5: 82,798,102-82,836,281 | q35 | Loss | 38,179 | 66.7 | 9.2 | 57.5 | 1.95E−09 | 2.61E−08 | BEAN1, CDH5 |
| chr5: 82,836,281-82,845,474 | q35 | Loss | 9,193 | 69.7 | 9.2 | 60.5 | 3.47E−10 | 5.61E−09 | CDH5 |
| chr5: 82,845,474-83,012,607 | q35 | Loss | 167,133 | 72.7 | 9.2 | 63.5 | 5.64E−11 | 1.21E−09 | CDH5 |
| chr5: 83,012,607-83,027,347 | q35 | Loss | 14,740 | 69.7 | 9.2 | 60.5 | 3.47E−10 | 5.61E−09 | |
| chr5: 83,027,347-83,075,902 | q35 | Loss | 48,555 | 63.6 | 3.9 | 59.7 | 3.09E−11 | 6.77E−10 | |
| chr5: 83,075,902-83,178,724 | q35 | Loss | 102,822 | 63.6 | 2.6 | 61.0 | 4.45E−12 | 1.48E−10 | |
| chr5: 83,178,724-83,387,764 | q35 | Loss | 209,040 | 60.6 | 1.3 | 59.3 | 2.88E−12 | 1.11E−10 | |
| chr5: 83,387,764-83,589,799 | q35 | Loss | 202,035 | 63.6 | 1.3 | 62.3 | 4.46E−13 | 3.02E−11 | |
| chr5: 83,589,799-83,599,745 | q35 | Loss | 9,946 | 60.6 | 1.3 | 59.3 | 2.88E−12 | 1.11E−10 | |
| chr5: 83,599,745-83,708,089 | q35 | Loss | 108,344 | 54.5 | 1.3 | 53.2 | 9.97E−11 | 1.85E−09 | |
| chr5: 83,708,089-84,025,109 | q35-q36 | Loss | 317,020 | 51.5 | 1.3 | 50.2 | 5.38E−10 | 8.10E−09 | LOC102152798, CDH11 |
| chr5: 84,849,361-85,134,032 | q36 | Loss | 284,671 | 51.5 | 1.3 | 50.2 | 5.38E−10 | 8.10E−09 | |
| chr5: 85,324,982-85,369,946 | q36 | Loss | 44,964 | 54.5 | 2.6 | 51.9 | 8.40E−10 | 1.18E−08 | |
| chr5: 86,316,203-86,469,234 | q36 | Loss | 153,031 | 54.5 | 2.6 | 51.9 | 8.40E−10 | 1.18E−08 | LOC102153075, CDH8 |
| chr5: 87,498,411-87,778,294 | q36 | Loss | 279,883 | 54.5 | 2.6 | 51.9 | 8.40E−10 | 1.18E−08 | |
| chr5: 87,778,294-87,872,957 | q36 | Loss | 94,663 | 60.6 | 2.6 | 58.0 | 2.72E−11 | 6.21E−10 | LOC479698 |
| chr5: 87,872,957-88,011,870 | q36 | Loss | 138,913 | 63.6 | 2.6 | 61.0 | 4.45E−12 | 1.48E−10 | LOC479698 |
| chr5: 88,011,870-88,125,949 | q36 | Loss | 114,079 | 60.6 | 2.6 | 58.0 | 2.72E−11 | 6.21E−10 | |
| chr5: 88,125,949-88,139,142 | q36 | Loss | 13,193 | 57.6 | 2.6 | 54.9 | 1.56E−10 | 2.67E−09 | |
| chr5: 88,139,142-88,428,223 | q36 | Loss | 289,081 | 54.5 | 2.6 | 51.9 | 8.40E−10 | 1.18E−08 | |
| chr5: 88,428,223-88,692,989 | q36 | Loss | 264,766 | 57.6 | 2.6 | 54.9 | 1.56E−10 | 2.67E−09 | |
| chr5: 88,692,989-88,915,250 | q36 | Loss | 222,261 | 63.6 | 5.3 | 58.4 | 1.67E−10 | 2.84E−09 | |
| chr31: 3,574,978-3,606,485 | q11 | Gain | 31,507 | 54.5 | 3.9 | 50.6 | 4.94E−09 | 4.90E−07 | |
| chr31: 3,606,485-3,713,760 | q11 | Gain | 107,275 | 57.6 | 3.9 | 53.6 | 9.72E−10 | 2.43E−07 | |
| chr31: 3,713,760-3,927,488 | q11 | Gain | 213,728 | 57.6 | 5.3 | 52.3 | 4.74E−09 | 4.90E−07 | |
| chr31: 4,494,597-6,181,347 | q12 | Gain | 1,686,750 | 57.6 | 5.3 | 52.3 | 4.74E−09 | 4.90E−07 | LOC102152860, RPL6P, LOC478380 |
| chr31: 6,742,546-8,389,449 | q12 | Gain | 1,646,903 | 57.6 | 5.3 | 52.3 | 4.74E−09 | 4.90E−07 | ROBO1, LOC102153268, LOC102153225 |
| chr31: 8,389,449-8,517,658 | q12 | Gain | 128,209 | 57.6 | 6.6 | 51.0 | 1.92E−08 | 1.26E−06 | ROBO1 |
| chr31: 8,517,658-8,645,671 | q12 | Gain | 128,013 | 60.6 | 6.6 | 54.0 | 3.94E−09 | 4.90E−07 | ROBO1 |
| chr31: 8,645,671-8,751,964 | q12 | Gain | 106,293 | 60.6 | 5.3 | 55.3 | 9.21E−10 | 2.43E−07 | |
| chr31: 8,751,964-9,390,589 | q12 | Gain | 638,625 | 57.6 | 5.3 | 52.3 | 4.74E−09 | 4.90E−07 | |
| chr31: 9,390,589-9,821,887 | q12 | Gain | 431,298 | 60.6 | 5.3 | 55.3 | 9.21E−10 | 2.43E−07 | LOC487691 |
| chr31: 9,821,887-9,909,162 | q12 | Gain | 87,275 | 63.6 | 5.3 | 58.4 | 1.67E−10 | 2.43E−07 | LOC487691 |
| chr31: 9,909,162-9,996,577 | q12 | Gain | 87,415 | 60.6 | 5.3 | 55.3 | 9.21E−10 | 2.43E−07 | LOC478381, LOC487691 |
| chr31: 9,996,577-10,721,940 | q12 | Gain | 725,363 | 57.6 | 5.3 | 52.3 | 4.74E−09 | 4.90E−07 | LOC487691, LOC102153311 |
| chr31: 10,721,940-10,990,663 | q12 | Gain | 268,723 | 60.6 | 5.3 | 55.3 | 9.21E−10 | 2.43E−07 | LOC102153814 |
| chr31: 10,990,663-11,662,746 | q12-q13 | Gain | 672,083 | 60.6 | 6.6 | 54.0 | 3.94E−09 | 4.90E−07 | LIPI, RBM11, LOC102154069, LOC478384, LOC102153846, HSPA13, LOC102154431, SAMSN1 |
| chr31: 11,662,746-11,814,984 | q13 | Gain | 152,238 | 60.6 | 5.3 | 55.3 | 9.21E−10 | 2.43E−07 | SAMSN1, LOC100684485 |
| chr31: 11,814,984-12,217,908 | q13 | Gain | 402,924 | 63.6 | 6.6 | 57.1 | 7.51E−10 | 2.43E−07 | NRIP1 |
| chr31: 12,217,908-12,526,736 | q13 | Gain | 308,828 | 60.6 | 6.6 | 54.0 | 3.94E−09 | 4.90E−07 | LOC102155616, LOC102154762 |
| chr31: 12,526,736-12,876,407 | q13 | Gain | 349,671 | 60.6 | 5.3 | 55.3 | 9.21E−10 | 2.43E−07 | USP25 |
| chr31: 12,876,407-12,941,599 | q13 | Gain | 65,192 | 57.6 | 5.3 | 52.3 | 4.74E−09 | 4.90E−07 | |
| chr31: 12,941,599-13,157,803 | q13 | Gain | 216,204 | 57.6 | 6.6 | 51.0 | 1.92E−08 | 1.26E−06 | LOC102154980 |
| chr31: 13,157,803-13,956,866 | q13 | Gain | 799,063 | 57.6 | 5.3 | 52.3 | 4.74E−09 | 4.90E−07 | LOC102154980, LOC102155084 |
| chr31: 13,956,866-14,419,403 | q13 | Gain | 462,537 | 57.6 | 6.6 | 51.0 | 1.92E−08 | 1.26E−06 | CXADR, LOC487695, LOC102155790, C31H21orf91 |
| chr31: 14,419,403-14,964,747 | q13 | Gain | 545,344 | 57.6 | 5.3 | 52.3 | 4.74E−09 | 4.90E−07 | CHODL, TMPRSS15 |
| chr31: 14,964,747-15,776,949 | q13 | Gain | 812,202 | 60.6 | 5.3 | 55.3 | 9.21E−10 | 2.43E−07 | |
| chr31: 15,776,949-16,031,595 | q13 | Gain | 254,646 | 57.6 | 3.9 | 53.6 | 9.72E−10 | 2.43E−07 | |
| chr31: 16,031,595-16,147,594 | q13 | Gain | 115,999 | 60.6 | 3.9 | 56.7 | 1.79E−10 | 2.43E−07 | |
| chr31: 16,147,594-16,653,042 | q13-q14 | Gain | 505,448 | 60.6 | 5.3 | 55.3 | 9.21E−10 | 2.43E−07 | LOC102156052 |
| chr31: 16,653,042-16,851,394 | q14 | Gain | 198,352 | 63.6 | 5.3 | 58.4 | 1.67E−10 | 2.43E−07 | |
| chr31: 16,851,394-17,451,755 | q14 | Gain | 600,361 | 60.6 | 5.3 | 55.3 | 9.21E−10 | 2.43E−07 | EEF1A1, NCAM2 |
| chr31: 17,451,755-17,748,133 | q14 | Gain | 296,378 | 60.6 | 6.6 | 54.0 | 3.94E−09 | 4.90E−07 | |
| chr31: 17,748,133-17,766,239 | q14 | Gain | 18,106 | 57.6 | 6.6 | 51.0 | 1.92E−08 | 1.26E−06 | |
| chr31: 17,766,239-18,277,334 | q14 | Gain | 511,095 | 57.6 | 5.3 | 52.3 | 4.74E−09 | 4.90E−07 | |
| chr31: 19,317,125-19,482,884 | q14 | Gain | 165,759 | 57.6 | 5.3 | 52.3 | 4.74E−09 | 4.90E−07 | |
| chr31: 19,889,449-19,909,607 | q14 | Gain | 20,158 | 57.6 | 6.6 | 51.0 | 1.92E−08 | 1.26E−06 | |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| chr31: 19,909,607-20,085,761 | q14 | Gain | 176,154 | 60.6 | 6.6 | 54.0 | 3.94E−09 | 4.90E−07 | LOC102156356, LOC102156405 |
| chr31: 20,085,761-20,166,178 | q14 | Gain | 80,417 | 60.6 | 5.3 | 55.3 | 9.21E−10 | 2.43E−07 | |
| chr31: 20,166,178-20,180,593 | q14 | Gain | 14,415 | 57.6 | 5.3 | 52.3 | 4.74E−09 | 4.90E−07 | |
| chr31: 20,869,268-21,005,369 | q14 | Gain | 136,101 | 57.6 | 5.3 | 52.3 | 4.74E−09 | 4.90E−07 | |
| chr31: 21,005,369-21,031,105 | q14 | Gain | 25,736 | 57.6 | 6.6 | 51.0 | 1.92E−08 | 1.26E−06 | |
| chr31: 21,031,105-21,257,672 | q14 | Gain | 226,567 | 60.6 | 6.6 | 54.0 | 3.94E−09 | 4.90E−07 | MRPL39, JAM2, ATP5J, GABPA, LOC102156977 |
| chr31: 21,257,672-21,441,947 | q14 | Gain | 184,275 | 57.6 | 6.6 | 51.0 | 1.92E−08 | 1.26E−06 | APP |
| chr31: 21,441,947-21,622,269 | q14 | Gain | 180,322 | 60.6 | 6.6 | 54.0 | 3.94E−09 | 4.90E−07 | APP, LOC102151217 |
| chr31: 21,622,269-21,749,206 | q14-q15.1 | Gain | 126,937 | 57.6 | 6.6 | 51.0 | 1.92E−08 | 1.26E−06 | LOC102151217 |
| chr31: 21,749,206-22,049,143 | q15.1 | Gain | 299,937 | 57.6 | 5.3 | 52.3 | 4.74E−09 | 4.90E−07 | LOC102151217, CYYR1, LOC487711 |
| chr31: 22,049,143-22,759,280 | q15.1 | Gain | 710,137 | 60.6 | 6.6 | 54.0 | 3.94E−09 | 4.90E−07 | LOC102151271, ADAMTS1, ADAMTS5, LOC102151422 |
| chr31: 22,759,280-23,102,209 | q15.1 | Gain | 342,929 | 63.6 | 6.6 | 57.1 | 7.51E−10 | 2.43E−07 | |
| chr31: 23,102,209-23,622,081 | q15.1 | Gain | 519,872 | 60.6 | 6.6 | 54.0 | 3.94E−09 | 4.90E−07 | |
| chr31: 23,622,081-23,967,926 | q15.1 | Gain | 345,845 | 57.6 | 6.6 | 51.0 | 1.92E−08 | 1.26E−06 | LOC102151634, LOC487715, LTN1 |
| chr31: 23,967,926-24,163,030 | q15.1 | Gain | 195,104 | 60.6 | 6.6 | 54.0 | 3.94E−09 | 4.90E−07 | LTN1, RWDD2B, USP16, CCT8, C31H21orf7 |
| chr31: 24,163,030-24,505,719 | q15.1 | Gain | 342,689 | 60.6 | 5.3 | 55.3 | 9.21E−10 | 2.43E−07 | C31H21orf7, BACH1, GRIK1 |
| chr31: 24,505,719-24,642,006 | q15.1 | Gain | 136,287 | 60.6 | 6.6 | 54.0 | 3.94E−09 | 4.90E−07 | GRIK1 |
| chr31: 24,642,006-25,422,064 | q15.1 | Gain | 780,058 | 60.6 | 5.3 | 55.3 | 9.21E−10 | 2.43E−07 | GRIK1, CLDN17, LOC102153451, CLDN8, KRTAP24-1, LOC102153645, KRTAP26-1, KRTAP27-1, KRTAP23-1, KRTAP13-2, LOC100686187, LOC100686265, LOC100686358, LOC100686441, LOC100686522, KRTAP19-4 |
| chr31: 25,422,064-26,015,104 | q15.1 | Gain | 593,040 | 60.6 | 6.6 | 54.0 | 3.94E−09 | 4.90E−07 | LOC102151701, LOC102151782, LOC100686828, LOC102151849, KRTAP8-1, KRTAP7-1, KRTAP11-1 |
| chr31: 26,015,104-26,207,846 | q15.1 | Gain | 192,742 | 57.6 | 6.6 | 51.0 | 1.92E−08 | 1.26E−06 | TIAM1 |
| chr31: 26,366,005-26,510,397 | q15.1 | Gain | 144,392 | 57.6 | 6.6 | 51.0 | 1.92E−08 | 1.26E−06 | TIAM1 |
| chr31: 26,510,397-26,548,528 | q15.1 | Gain | 38,131 | 63.6 | 7.9 | 55.7 | 2.91E−09 | 4.90E−07 | SOD1, SCAF4 |
| chr31: 26,548,528-26,617,285 | q15.1 | Gain | 68,757 | 63.6 | 6.6 | 57.1 | 7.51E−10 | 2.43E−07 | SCAF4, LOC102155229 |
| chr31: 26,617,285-26,647,666 | q15.1 | Gain | 30,381 | 60.6 | 6.6 | 54.0 | 3.94E−09 | 4.90E−07 | LOC102155229 |
| chr31: 27,306,560-27,479,144 | q15.1 | Gain | 172,584 | 60.6 | 6.6 | 54.0 | 3.94E−09 | 4.90E−07 | SYNJ1, PAXBP1, C31H21orf62 |
| chr31: 27,479,144-27,563,388 | q15.1 | Gain | 84,244 | 57.6 | 6.6 | 51.0 | 1.92E−08 | 1.26E−06 | C31H21orf62 |
| chr31: 27,993,323-28,087,673 | q15.1 | Gain | 94,350 | 66.7 | 14.5 | 52.2 | 1.36E−07 | 4.48E−06 | LOC102151345, LOC100856276, LOC100856546 |
| chr31: 28,087,673-28,150,222 | q15.1 | Gain | 62,549 | 69.7 | 14.5 | 55.2 | 2.89E−08 | 1.48E−06 | LOC100856546, LOC100856290, LOC100856570 |
| chr31: 28,150,222-28,597,951 | q15.1 | Gain | 447,729 | 66.7 | 6.6 | 60.1 | 1.33E−10 | 2.43E−07 | LOC100856570, LOC100856585, DONSON, LOC100856647, LOC100856635, LOC102153983, ATP5O, LOC102152930 |
| chr31: 28,597,951-28,648,317 | q15.1 | Gain | 50,366 | 63.6 | 6.6 | 57.1 | 7.51E−10 | 2.43E−07 | LOC100856716 |
| chr31: 28,648,317-29,782,326 | q15.1 | Gain | 1,134,009 | 60.6 | 6.6 | 54.0 | 3.94E−09 | 4.90E−07 | IFNAR2, IL10RB, LOC102153360, LOC609830, LOC102153793, LOC487739, LOC478405, DNAJC28, LOC487740, SON, LOC478407, CRYZL1, ITSN1, LOC100688175, LOC100688250, LOC100855541, LOC102155085, SLC5A3, MRPS6, KCNE2, FAM165B |
| chr31: 29,782,326-29,925,895 | q15.1 | Gain | 143,569 | 66.7 | 10.5 | 56.1 | 6.34E−09 | 6.02E−07 | FAM165B, LOC102155325, LOC102155418, LOC487743, RCAN1 |
| chr31: 29,925,895-29,968,341 | q15.1 | Gain | 42,446 | 63.6 | 10.5 | 53.1 | 3.13E−08 | 1.59E−06 | RCAN1 |
| chr31: 29,985,712-29,999,819 | q15.1 | Gain | 14,107 | 60.6 | 9.2 | 51.4 | 4.78E−08 | 2.39E−06 | RCAN1 |
| chr31: 29,999,819-30,295,496 | q15.1 | Gain | 295,677 | 60.6 | 6.6 | 54.0 | 3.94E−09 | 4.90E−07 | RCAN1, CLIC6, RUNX1 |
| chr31: 30,295,496-30,328,439 | q15.1 | Gain | 32,943 | 63.6 | 6.6 | 57.1 | 7.51E−10 | 2.43E−07 | RUNX1 |
| chr31: 30,328,439-30,530,533 | q15.1 | Gain | 202,094 | 60.6 | 6.6 | 54.0 | 3.94E−09 | 4.90E−07 | RUNX1 |
| chr31: 30,530,533-30,596,729 | q15.1 | Gain | 66,196 | 63.6 | 6.6 | 57.1 | 7.51E−10 | 2.43E−07 | |
| chr31: 30,596,729-30,782,046 | q15.1 | Gain | 185,317 | 66.7 | 6.6 | 60.1 | 1.33E−10 | 2.43E−07 | LOC102156175 |
| chr31: 30,782,046-30,975,922 | q15.1 | Gain | 193,876 | 63.6 | 6.6 | 57.1 | 7.51E−10 | 2.43E−07 | |
| chr31: 30,975,922-31,201,087 | q15.1 | Gain | 225,165 | 63.6 | 5.3 | 58.4 | 1.67E−10 | 2.43E−07 | LOC609892 |
| chr31: 31,201,087-31,227,785 | q15.1 | Gain | 26,698 | 60.6 | 5.3 | 55.3 | 9.21E−10 | 2.43E−07 | |

TABLE 3-continued

Genomic regions significantly different between mut-KIT tumors and wt-KIT tumors

| Region | Loc | Event | Length | Freq in mut-KIT (%) | Freq in wt-KIT (%) | Diff (%) | p-value | q-bound | Gene Symbols |
|---|---|---|---|---|---|---|---|---|---|
| chr31: 31,227,785-31,294,473 | q15.1 | Gain | 66,688 | 57.6 | 5.3 | 52.3 | 4.74E−09 | 4.90E−07 | SETD4 |
| chr31: 31,889,542-32,205,283 | q15.1 | Gain | 315,741 | 60.6 | 6.6 | 54.0 | 3.94E−09 | 4.90E−07 | SIM2, HLCS, DSCR6 |
| chr31: 32,205,283-32,543,860 | q15.1-q15.2 | Gain | 338,577 | 63.6 | 6.6 | 57.1 | 7.51E−10 | 2.43E−07 | PIGP, TTC3, LOC102151700, DSCR3, DYRK1A |
| chr31: 32,543,860-32,733,279 | q15.2 | Gain | 189,419 | 57.6 | 6.6 | 51.0 | 1.92E−08 | 1.26E−06 | DYRK1A, LOC102152474, LOC102151965 |
| chr31: 34,066,143-34,101,861 | q15.2 | Gain | 35,718 | 60.6 | 9.2 | 51.4 | 4.78E−08 | 2.39E−06 | |
| chr31: 34,101,861-34,121,248 | q15.2 | Gain | 19,387 | 63.6 | 9.2 | 54.4 | 1.00E−08 | 9.41E−07 | |
| chr31: 34,121,248-34,151,499 | q15.2 | Gain | 30,251 | 66.7 | 9.2 | 57.5 | 1.95E−09 | 4.59E−07 | BRWD1 |
| chr31: 34,151,499-34,325,320 | q15.2 | Gain | 173,821 | 63.6 | 6.6 | 57.1 | 7.51E−10 | 2.43E−07 | BRWD1, LOC100685290, HMGN1 |
| chr31: 34,325,320-34,968,541 | q15.2-q15.3 | Gain | 643,221 | 60.6 | 6.6 | 54.0 | 3.94E−09 | 4.90E−07 | B3GALT5, IGSF5, PCP4, DSCAM |
| chr31: 34,968,541-35,026,069 | q15.3 | Gain | 57,528 | 57.6 | 6.6 | 51.0 | 1.92E−08 | 1.26E−06 | DSCAM |
| chr31: 35,212,014-35,436,330 | q15.3 | Gain | 224,316 | 57.6 | 5.3 | 52.3 | 4.74E−09 | 4.90E−07 | DSCAM |
| chr31: 35,436,330-35,611,912 | q15.3 | Gain | 175,582 | 57.6 | 6.6 | 51.0 | 1.92E−08 | 1.26E−06 | |
| chr31: 36,240,655-36,347,617 | q15.3 | Gain | 106,962 | 54.5 | 3.9 | 50.6 | 4.94E−09 | 4.90E−07 | PRDM15, LOC102154225, C2CD2 |
| chr31: 39,613,234-39,674,420 | q15.3 | Gain | 61,186 | 57.6 | 6.6 | 51.0 | 1.92E−08 | 1.26E−06 | PCNT |
| chr31: 39,674,420-39,702,857 | q15.3 | Gain | 28,437 | 60.6 | 6.6 | 54.0 | 3.94E−09 | 4.90E−07 | PCNT, DIP2A |
| chr31: 39,702,857-39,895,921 | q15.3 | Gain | 193,064 | 60.6 | 7.9 | 52.7 | 1.46E−08 | 1.19E−06 | DIP2A, S100B, PRMT2 |
| chr36:21,365,605-21,435,803 | q14 | Gain | 70,198 | 54.5 | 2.6 | 51.9 | 8.40E−10 | 2.43E−07 | LOC102152241, PDE11A |
| chr36:21,435,803-21,571,604 | q14 | Gain | 135,801 | 54.5 | 3.9 | 50.6 | 4.94E−09 | 4.90E−07 | PDE11A |
| chr36:22,206,259-22,262,382 | q14 | Gain | 56,123 | 54.5 | 3.9 | 50.6 | 4.94E−09 | 4.90E−07 | TTN |
| chr36:22,262,382-22,880,297 | q14 | Gain | 617,915 | 54.5 | 2.6 | 51.9 | 8.40E−10 | 2.43E−07 | TTN, CCDC141, SESTD1 |
| chr36:28,200,299-28,282,448 | q15 | Gain | 82,149 | 60.6 | 9.2 | 51.4 | 4.78E−08 | 2.39E−06 | FSIP2 |
| chr36:28,282,448-28,298,114 | q15 | Gain | 15,666 | 57.6 | 6.6 | 51.0 | 1.92E−08 | 1.26E−06 | |
| chr36:28,298,114-28,473,376 | q15 | Gain | 175,262 | 54.5 | 2.6 | 51.9 | 8.40E−10 | 2.43E−07 | |

TABLE 4

Significant CNAs in wt-KIT tumors identified by GISTIC analysis

| No. | Region (CanFam3) | Extended Region | Type | Q-Bound | G-Score |
|---|---|---|---|---|---|
| 1 | chr1: 63,742,997-63,803,385 | chr1: 63,742,997-63,803,385 | Loss | 9.40E−09 | 20.03 |
| 2 | chr1: 98,513,040-98,728,698 | chr1: 98,500,725-107,055,454 | Gain | 1.19E−02 | 4.09 |
| 3 | chr1: 111,745,837-111,764,765 | chr1: 111,745,837-111,773,264 | Loss | 1.15E−05 | 10.02 |
| 4 | chr1: 117,108,373-117,174,987 | chr1: 117,091,834,-117,539,044 | Gain | 6.73E−08 | 8.39 |
| 5 | chr2: 19,854,075-19,889,268 | chr2: 19,854,075-19,897,270 | Gain | 3.42E−02 | 3.68 |
| 6 | chr2: 23,201,419-23,241,899 | chr2: 23,201,419-23,241899 | Loss | 2.37E−05 | 9.32 |
| 7 | chr2: 35,966,135-36,003,432 | chr2: 35,921,044-36,003,432 | Gain | 1.16E−02 | 4.10 |
| 8 | chr2: 84,126,143-84,151,550 | chr2: 83,970,260-84,151,550 | Gain | 2.01E−10 | 14.74 |
| 9 | chr2: 84,151,550-84,179,101 | chr2: 84,151,550-84,179,101 | Loss | 3.72E−04 | 7.30 |
| 10 | chr3: 59,944,361-60,185,123 | chr3: 59,753,458-60,185,123 | Gain | 7.96E−05 | 6.04 |
| 11 | chr3: 60,423,519,60,515,009 | chr3: 60,423,519-60,585,098 | Loss | 7.40E−04 | 6.93 |
| 12 | chr3: 91,351,987-91,448,431 | chr3: 91,351,987-91,681,975 | Loss | 2.24E−02 | 5.09 |
| 13 | chr3: 91,781,169-91,786,770 | chr3: 91,681,975-91,786,770 | Gain | 8.21E−03 | 4.27 |
| 14 | chr4: 14,010,773-14,124,513 | chr4: 14,001,344-14,124,513 | Gain | 6.28E−03 | 4.36 |
| 15 | chr4: 34,760,329-35,027,498 | chr4: 34,745,245,-35,056,833 | Loss | 9.70E−04 | 6.78 |
| 16 | chr4: 35,861,977-36,002,900 | chr4: 35,851,080-36,002,900 | Gain | 2.01E−10 | 15.55 |
| 17 | chr5: 1-133,326 | chr5: 1-133,326 | Loss | 6.97E−04 | 6.96 |
| 18 | chr5: 19,772,292-19,870,693 | chr5: 1,333,535-19,870,693 | Gain | 4.77E−03 | 4.48 |
| 19 | chr5: 32,224,217-32,261,183 | chr5: 32,224,217-32,312,981 | Gain | 2.01E−10 | 17.75 |
| 20 | chr5: 56,349,012-56,415,940 | chr5: 56,332,351-56,526,415 | Gain | 2.47E−03 | 4.78 |
| 21 | chr5: 78,183,082-78,251,390 | chr5: 78,150,222-78,399,717 | Loss | 9.40E−09 | 25.16 |
| 22 | chr5: 78,251,390-78,342,207 | chr5: 78,183,082-78,399,717 | Gain | 2.01E−10 | 13.74 |
| 23 | chr5: 81,265,802-81,360,136 | chr5: 81,265,802-81,360,136 | Gain | 2.35E−02 | 3.83 |
| 24 | chr6: 9,019,278-9,130,821 | chr6: 7,538,713-9,671,493 | Gain | 1.63E−07 | 8.11 |
| 25 | chr6: 38,821,209-38,890,486 | chr6: 38,821,209-38,967,548 | Gain | 2.01E−10 | 13.45 |
| 26 | chr6: 40,670,034-40,690,650 | chr6: 40,670,034-40,720,194 | Loss | 2.02E−07 | 12.14 |
| 27 | chr6: 45,833,720-46,090,567 | chr6: 45,426,941-46,481,846 | Loss | 1.82E−03 | 6.48 |
| 28 | chr6: 47,044,166-47,111,711 | chr6: 46,993,224-47,132,538 | Gain | 1.02E−04 | 5.96 |
| 29 | chr7: 1-48,912 | chr7: 1-74,145 | Gain | 3.10E−05 | 6.36 |
| 30 | chr7: 41,776,035-41,851,194 | chr7: 41,772,322-41,851,194 | Gain | 2.01E−10 | 14.09 |
| 31 | chr7: 71,181,689-71,239,464 | chr7: 71,181,689-71,239,464 | Loss | 9.40E−09 | 19.86 |
| 32 | chr8: 2,739,349-2,765,393 | chr8: 2,677,487-2,792,410 | Gain | 2.11E−10 | 10.79 |
| 33 | chr8: 72,704,964-72,826,938 | chr8: 72,677,095-73,022,906 | Gain | 1.31E−07 | 8.17 |
| 34 | chr8: 73,379,979-73,400,408 | chr8: 73,379,979-73,757,566 | Loss | 9.40E−09 | 39.12 |
| 35 | chr9: 1-48,674 | chr9: 1-48,674 | Loss | 1.33E−03 | 6.61 |

TABLE 4-continued

Significant CNAs in wt-KIT tumors identified by GISTIC analysis

| No. Region (CanFam3) | Extended Region | Type | Q-Bound | G-Score |
|---|---|---|---|---|
| 36 chr9: 503,870-532,310 | chr9: 225,593-537,724 | Gain | 6.28E−05 | 6.14 |
| 37 chr9: 17,312,039-17,732,745 | chr9: 17,312,039-17,969,293 | Loss | 2.93E−08 | 13.30 |
| 38 chr9: 17,969,293-18,092,618 | chr9: 17,969,293-18,092,618 | Gain | 8.22E−08 | 8.33 |
| 39 chr9: 38,984,357-38,998,563 | chr9: 38,972,979-38,998,563 | Loss | 9.40E−09 | 35.52 |
| 40 chr9: 38,998,563-39,010,776 | chr9: 38,998,563-39,010,776 | Gain | 2.01E−10 | 13.90 |
| 41 chr9: 57,683,444-57,748,629 | chr9: 57,683,444-61,074,082 | Loss | 2.81E−02 | 4.94 |
| 42 chr10: 1,728,923-1,848,374 | chr10: 96,774-1,848,374 | Gain | 2.89E−06 | 7.18 |
| 43 chr10: 17,020,231-17,066,756 | chr10: 17,020,231-17,066,756 | Gain | 2.01E−10 | 11.94 |
| 44 chr10: 17,775,058-17,872,494 | chr10: 17,365,609-19,611,483 | Loss | 1.17E−03 | 6.69 |
| 45 chr10: 45,716,711-45,751,320 | chr10: 45,691,620-45,803,956 | Gain | 9.85E−07 | 7.54 |
| 46 chr11: 52,587,841-52,683,204 | chr11: 52,587,841-52,722,960 | Gain | 2.01E−10 | 19.38 |
| 47 chr11: 68,433,695-68,603,240 | chr11: 68,433,695-68,603,240 | Loss | 1.53E−03 | 6.54 |
| 48 chr12: 1,529,469-1,583,900 | chr12: 1,300,212-1,583,900 | Gain | 2.26E−04 | 5.68 |
| 49 chr12: 2,604,766-2,661,228 | chr12: 2,604,766-2,664,169 | Gain | 2.01E−10 | 17.59 |
| 50 chr12: 72,079,628-72,251,175 | chr12: 72,079,628-72,272,418 | Loss | 4.57E−05 | 8.64 |
| 51 chr13: 2,443,805-2,490,453 | chr13: 2,443,805-2,490,453 | Loss | 9.40E−09 | 15.41 |
| 52 chr13: 35,964,725-36,122,185 | chr13: 35,964,725-36,149,644 | Loss | 9.17E−05 | 8.15 |
| 53 chr13: 37,377,311-37,700,001 | chr13: 37,364,026-37,746,957 | Gain | 2.01E−10 | 12.93 |
| 54 chr14: 2,808,378-2,842,648 | chr14: 2,113,422-2,861,174 | Loss | 9.40E−09 | 17.21 |
| 55 chr14: 4,972,455-5,338,685 | chr14: 4,938,913-5,338,685 | Gain | 2.81E−03 | 4.73 |
| 56 chr14: 43,551,303-43,621,522 | chr14: 43,537,923-43,629,021 | Loss | 2.01E−10 | 14.74 |
| 57 chr15: 1,346,848-1,499,163 | chr15: 1,346,848-1,499,163 | Gain | 5.96E−10 | 9.91 |
| 58 chr15: 7,819,131-7,934,777 | chr15: 5,036,356-7,980,691 | Loss | 6.24E−03 | 5.85 |
| 59 chr15: 63,811,147-63,982,204 | chr15: 63,811,147-63,982,204 | Loss | 1.05E−04 | 8.05 |
| 60 chr16: 1-309,348 | chr16: 1-407,916 | Loss | 2.09E−03 | 6.39 |
| 61 chr16: 9,149,776-9,181,393 | chr16: 8,551,949-9,217,088 | Gain | 1.32E−02 | 4.04 |
| 62 chr16: 54,356,690-54,473,666 | chr16: 54,297,462-56,683,206 | Loss | 1.46E−05 | 9.80 |
| 63 chr17: 403,827-620,898 | chr17: 1-689,496 | Loss | 4.31E−05 | 8.68 |
| 64 chr17: 56,665,179-56,686,048 | chr17: 56,665,179-56,686,048 | Gain | 5.96E−09 | 9.13 |
| 65 chr17: 64,159,048-64,289,059 | chr17: 64,159,048-64,289,059 | Loss | 6.44E−03 | 5.82 |
| 66 chr18: 1,976,678-2,065,321 | chr18: 1-2,065,321 | Loss | 1.67E−02 | 5.28 |
| 67 chr18: 11,339,197-11,416,499 | chr18: 11,339,197-11,416,499 | Gain | 2.94E−05 | 6.39 |
| 68 chr18: 38,683,599-38,800,287 | chr18: 38,683,599-38,800,287 | Loss | 1.55E−03 | 6.53 |
| 69 chr18: 46,318,953-46,383,384 | chr18: 46,318,953-46,510,748 | Gain | 2.01E−10 | 12.96 |
| 70 chr19: 2,901,106-2,979,475 | chr19: 2,901,106-2,979,475 | Gain | 6.67E−05 | 6.11 |
| 71 chr19: 20,036,378-20,295,719 | chr19: 19,933,994-20,329,284 | Loss | 2.84E−04 | 7.45 |
| 72 chr20: 15,968,550-16,176,199 | chr20: 15,198-750-16,176,199 | Loss | 2.18E−04 | 7.63 |
| 73 chr20: 38,713,828-38,743,160 | chr20: 38,311,784-38,774,596 | Loss | 3.78E−07 | 11.95 |
| 74 chr20: 40,469,449-40,547,257 | chr20: 40,469,449-40,551,201 | Gain | 1.51E−02 | 4.00 |
| 75 chr20: 46,131,350-46,186,781 | chr20: 45,703,872-46,356,123 | Gain | 2.01E−10 | 19.43 |
| 76 chr20: 53,267,512-53,327,296 | chr20: 53,267,512-53,327,296 | Loss | 9.40E−09 | 45.38 |
| 77 chr20: 53,267,512-53,341,759 | chr20: 53,267,512-53,341,759 | Gain | 2.74E−02 | 4.73 |
| 78 chr20: 54,212,601-54,231,471 | chr20: 54,201,255-54,231,471 | Gain | 1.53E−08 | 8.84 |
| 79 chr20: 57,137,484-57,189,778 | chr20: 54,861,893-58,134,056 | Loss | 2.00E−02 | 5.16 |
| 80 chr21: 21,566,631-21,679,745 | chr21: 21,566,631-21,695,604 | Gain | 2.01E−10 | 13.61 |
| 81 chr22: 780,737-924,571 | chr22: 242,796-924,571 | Loss | 1.61E−03 | 6.52 |
| 82 chr22: 60,344,869-50,562,889 | chr22: 60,297,547-60,633,852 | Loss | 3.82E−02 | 4.71 |
| 83 chr23: 8,242,315-8,331,657 | chr23: 8,224,915-8,331,657 | Gain | 3.30E−03 | 4.66 |
| 84 chr23: 20,504,112-20,514,633 | chr23: 20,504,112-20,514,633 | Loss | 9.40E−09 | 25.27 |
| 85 chr23: 20,538,312-20,710,885 | chr23: 20,514,633-20,710,885 | Gain | 2.01E−10 | 14.20 |
| 86 chr23: 52,151,945-52,294,480 | chr23: 52,161,945-52,294,480 | Loss | 2.33E−04 | 7.57 |
| 87 chr24: 21,138,869-21,154,133 | chr24: 21,138,869-21,213,663 | Gain | 2.01E−10 | 13.32 |
| 88 chr24: 47,449,078-47,698,779 | chr24: 47,449,078-47,698,779 | Loss | 5.03E−03 | 5.95 |
| 89 chr25: 50,413,480-51,073,874 | chr25: 50,413,480-51,184,425 | Gain | 1.99E−05 | 6.53 |
| 90 chr25: 51,475,875-51,628,933 | chr25: 51,465,331-51,628,933 | Loss | 1.50E−04 | 7.82 |
| 91 chr26: 20,263,200-20,298,649 | chr26: 20,209,073-20,298,649 | Gain | 7.21E−08 | 8.37 |
| 92 chr26: 25,221,909-25,467,475 | chr26: 24,951,165-25,676,067 | Loss | 1.13E−03 | 6.71 |
| 93 chr26: 27,167,936-27,174,566 | chr26: 27,167,936-27,174,566 | Gain | 2.01E−10 | 31.38 |
| 94 chr26: 27,174,566-27,207,467 | chr26: 27,174,566-27,240,032 | Loss | 9.40E−09 | 66.15 |
| 95 chr26: 27,289,594-27,333,602 | chr26: 27,289,594-27,373,928 | Gain | 3.56E−03 | 3.62 |
| 96 chr26: 27,462,452-27,483,067 | chr26: 27,462,452-27,569,156 | Loss | 2.50E−03 | 6.30 |
| 97 chr26: 28,340,781-28,398,606 | chr26: 28,324,491-28,456,230 | Gain | 8.04E−09 | 9.06 |
| 98 chr27: 1,114,154-1,303,187 | chr27: 1-1,314,884 | Loss | 7.25E−05 | 8.35 |
| 99 chr27: 2,901,529-3,020,954 | chr27: 2,876,411-3,020,954 | Gain | 1.39E−02 | 4.03 |
| 100 chr27: 6,978,563-7,023,641 | chr27: 6,954,304-7,041,668 | Gain | 2.01E−10 | 18.06 |
| 101 chr27: 25,750,959-25,860,828 | chr27: 25,732,852-25,860,828 | Loss | 9.40E−09 | 15.89 |
| 102 chr27: 31,853,354-31,912,150 | chr27: 25,889,191-38,184,454 | Loss | 6.24E−03 | 5.85 |
| 103 chr27: 38,183,454-38,208,381 | chr27: 38,183,454-42,266,862 | Gain | 9.02E−03 | 4.23 |
| 104 chr28: 29,626,077-29,713,479 | chr28: 29,626,077-29,713,479 | Gain | 2.87E−02 | 3.75 |
| 105 chr28: 40,520,701-40,593,303 | chr28: 40,520,701-40,950,687 | Gain | 1.70E−09 | 9.52 |
| 106 chr28: 41,109,678-41,137,968 | chr28: 41,109,678-41,182,112 | Loss | 8.95E−07 | 11.34 |
| 107 chr29: 41,021,811-41,067,224 | chr29: 41,021,811-41,845,238 | Loss | 7.67E−03 | 5.72 |
| 108 chr30: 37,840,545-37,864,405 | chr30: 37,810,533-37,864,405 | Gain | 1.83E−05 | 6.55 |
| 109 chr30: 38,521,916-38,804,831 | chr30: 38,521,916-38,816,298 | Loss | 9.95E−03 | 5.58 |
| 110 chr31: 35,871,715-35,887,990 | chr31: 35,781,416-36,6313,542 | Loss | 4.20E−03 | 6.04 |
| 111 chr31: 37,299,916-37,327,631 | chr31: 36,664,322-38,941,533 | Gain | 6.60E−10 | 9.86 |

TABLE 4-continued

Significant CNAs in wt-KIT tumors identified by GISTIC analysis

| No. | Region (CanFam3) | Extended Region | Type | Q-Bound | G-Score |
|---|---|---|---|---|---|
| 112 | chr33: 30,728,795-30,797,016 | chr33: 30,659,185-31,185,184 | Gain | 1.90E-02 | 3.90 |
| 113 | chr34: 11,275,814-11,297,924 | chr34: 11,275,814-11,315,700 | Gain | 3.28E-10 | 10.20 |
| 114 | chr34: 11,470,898-11,501,692 | chr34: 11,338,716-11,552,092 | Loss | 1.58E-03 | 6.53 |
| 115 | chr35: 16,974,084-16,984,185 | chr35: 16,912,748-17,010,530 | Gain | 1.39E-02 | 4.03 |
| 116 | chr36: 28,176,666-28,282,448 | chr36: 28,176,666-28,282,448 | Gain | 3.63E-02 | 3.58 |
| 117 | chr37: 1-177,983 | chr37: 1-177,983 | Loss | 2.27E-05 | 9.15 |
| 118 | chr37: 177,983-248,456 | chr37: 177,983-266,890 | Gain | 2.81E-03 | 4.72 |
| 119 | chr37: 24,943,587-25,049,058 | chr37: 24,943,587-25,049,058 | Gain | 2.01E-10 | 12.26 |
| 120 | chr37: 30,389,938-30,452,090 | chr37: 30,312,057-30,837,612 | Loss | 2.70E-04 | 7.47 |
| 121 | chr37: 30,893,538-30,902,991 | chr37: 30,893,538-30,902,991 | Gain | 5.00E-03 | 4.46 |
| 122 | chr38: 724,265-752,803 | chr38: 717,842-752,803 | Gain | 4.17E-02 | 3.53 |
| 123 | chr38: 22,131,188-22,290,537 | chr38: 22,131,188-23,707,309 | Gain | 1.94E-05 | 6.53 |
| 124 | chr38: 23,762,444-23,914,537 | chr38: 23,762,444-23,914,537 | Loss | 4.09E-02 | 4.66 |
| 125 | chrX: 1-93,751 | chrX: 1-93,751 | Gain | 5.57E-10 | 9.95 |
| 126 | chrX: 32,269,966-32,297,891 | chrX: 32,269,966-32,297,891 | Loss | 9.40E-09 | 19.94 |
| 127 | chrX: 53,176,671-53,453,526 | chrX: 53,139,071-53,453,526 | Gain | 3.05E-04 | 5.56 |
| 128 | chrX: 71,803,071-71,951,577 | chrX: 71,744,008-72,049,231 | Loss | 9.40E-09 | 68.76 |
| 129 | chrX: 72,228,723-72,239,538 | chcX: 72,228,723-72,239,538 | Gain | 2.01E-10 | 16.15 |
| 130 | chrX: 120,981,052-121,071,550 | chrX: 120,943,561-121,071,550 | Loss | 1.68E-05 | 9.64 |
| 131 | chrX: 121,545,250-121,743,104 | chrX: 121,545,50-122,322,644 | Gain | 1.98E-07 | 8.06 |

TABLE 5

Significant CNAs in mut-KIT tumors identified by GISTIC analysis

| No. | Region | Extended Region | Type | Q-Bound | G-Score |
|---|---|---|---|---|---|
| 1 | chr1: 111,745,837-111,773,264 | chr1: 108,222,732-111,971,009 | Gain | 6.26E-03 | 5.11 |
| 2 | chr1: 111,745,837-111,773,264 | chr1: 111,745,837-111,773,264 | Loss | 6.27E-03 | 5.47 |
| 3 | chr2: 23,201,419-23,241,899 | chr2: 23,201,419-23,241,899 | Loss | 1.22E-03 | 6.32 |
| 4 | chr2: 35,924,044-35,970,446 | chr2: 35,903,106-35,996,135 | Gain | 6.62E-04 | 6.45 |
| 5 | chr2: 84,151,550-84,179,101 | chr2: 84,151,550-84,179,101 | Loss | 1.68E-02 | 4.64 |
| 6 | chr4: 35,861,977-35,979,387 | chr4: 35,842,040-36,002,900 | Gain | 1.94E-05 | 7.72 |
| 7 | chr5: 17,003,811-17,271,198 | chr5: 9,062,538-20,133,725 | Loss | 2.99E-04 | 6.95 |
| 8 | chr5: 78,150,222-78,183,082 | chr5: 78,150,222-78,415,957 | Loss | 1.34E-09 | 21.52 |
| 9 | chr5: 78,415,957-78,459,732 | chr5: 78,415,957-78,459,732 | Gain | 4.49E-03 | 5.46 |
| 10 | chr5: 82,845,474-83,027,347 | chr5: 81,360,136-88,915,250 | Loss | 6.36E-03 | 5.46 |
| 11 | chr6: 40,670,034-40,712,665 | chr6: 40,656,427-40,712,665 | Loss | 2.70E-06 | 9.90 |
| 12 | chr6: 47,044,166-47,111,711 | chr6: 47,025,866-47,111,711 | Gain | 1.02E-03 | 6.25 |
| 13 | chr7: 41,818,563-41,843,764 | chr7: 41,591,428-41,851,194 | Gain | 3.40E-03 | 5.63 |
| 14 | chr7: 71,181,689-71,239,464 | chr7: 42,534,961-80,974,532 | Loss | 1.58E-02 | 4.70 |
| 15 | chr8: 73,379,979-73,391,779 | chr8: 73,379,979-74,008,358 | Loss | 1.34E-09 | 19.31 |
| 16 | chr9: 0-40,344 | chr9: 1-212,867 | Loss | 5.87E-03 | 5.50 |
| 17 | chr9: 17,297,936-17,312,039 | chr9: 17,259,902-17,312,039 | Gain | 9.13E-06 | 7.95 |
| 18 | chr9: 38,972,929-38,998,563 | chr9: 38,972,929-38,998,563 | Loss | 1.34E-09 | 26.83 |
| 19 | chr9: 38,998,563-39,010,776 | chr9: 38,998,563-39,010,776 | Gain | 1.22E-03 | 6.16 |
| 20 | chr10: 17,365,609-17,503,037 | chr10: 17,365,609-18,606,267 | Loss | 3.17E-02 | 4.17 |
| 21 | chr11: 52,587,841-52,700,545 | chr11: 52,587,841-52,722,960 | Gain | 6.01E-03 | 5.18 |
| 22 | chr11: 68,461,968-68,603,240 | chr11: 68,433,695-68,612,918 | Loss | 1.24E-03 | 6.31 |
| 23 | chr12: 2,604,766-2,643,750 | chr12: 2,604,766-2,661,228 | Gain | 1.14E-02 | 4.48 |
| 24 | chr12: 72,079,628-72,251,175 | chr12: 72,017,711-72,328,821 | Loss | 1.63E-02 | 4.67 |
| 25 | chr13: 2,443,805-2,490,453 | chr13: 2,443,805-2,490,453 | Gain | 2.01E-05 | 8.25 |
| 26 | chr13: 46,940,621-47,030,653 | chr13: 43,553,562-62,751,630 | Gain | 2.51E-05 | 7.64 |
| 27 | chr14: 2,522,789-2,842,648 | chr14: 2,322,259-2,861,174 | Loss | 1.68E-06 | 10.43 |
| 28 | chr14: 18,158,442-18,470,051 | chr14: 16,268,322-18,687,430 | Gain | 6.54E-07 | 8.71 |
| 29 | chr15: 7,644,414-7,992,325 | chr15: 7,042,368-7,992,325 | Loss | 4.00E-02 | 4.01 |
| 30 | chr15: 63,811,147-63,951,198 | chr15: 63,772,273-63,982,204 | Loss | 2.79E-03 | 5.94 |
| 31 | chr16: 54,356,690-54,473,666 | chr16: 54,356,690-54,530,683 | Loss | 2.70E-06 | 9.90 |
| 32 | chr17: 403,827-620,898 | chr17: 1-1,194,858 | Loss | 1.57E-02 | 4.71 |
| 33 | chr17: 56,787,475-56,820,514 | chr17: 56,665,179-,56,855,694 | Gain | 3.27E-03 | 5.66 |
| 34 | chr17: 64,174,093-64,289,059 | chr17: 64,159,048-64,289,059 | Loss | 4.10E-03 | 5.72 |
| 35 | chr18: 38,726,595-38,789,728 | chr18: 38,655,067-,38,800,287 | Loss | 9.03E-05 | 7.46 |
| 36 | chr19: 20,036,378-20,295,719 | chr19: 19,933,944-20,329,284 | Loss | 4.10E-03 | 5.72 |
| 37 | chr20: 48,403,168-48,458,171 | chr20: 48,053,474-48,512,348 | Gain | 1.78E-04 | 6.97 |
| 38 | chr20: 53,267,512-53,327,296 | chr20: 53,267,512-53,327,296 | Loss | 8.57E-07 | 11.07 |
| 39 | chr21: 45,003,472-45,130,560 | chr21: 43,179,918-50,585,623 | Gain | 4.69E-02 | 3.56 |
| 40 | chr22: 60,297,547-60,513,761 | chr22: 60,297,547-61,439,934 | Loss | 1.03E-03 | 6.41 |
| 41 | chr23: 20,504,112-20,669,834 | chr23: 20,504,112-20,710,885 | Loss | 1.34E-09 | 15.18 |
| 42 | chr23: 52,151,945-52,294,480 | chr23: 52,151,945-52,294,480 | Loss | 6.51E-03 | 5.43 |
| 43 | chr24: 47,470,936-47,698,779 | chr24: 44,594,747-47,698,779 | Loss | 1.07E-02 | 5.02 |
| 44 | chr25: 49,654,288-49,893,248 | chr25: 49,161,012-51,246,100 | Loss | 2.73E-02 | 4.27 |
| 45 | chr26: 5,372,761-5,454,082 | chr26: 5,021,666-8,071,151 | Gain | 1.47E-03 | 6.08 |
| 46 | chr26: 27,167,936-27,174,566 | chr26: 27,167,936-27,174,566 | Gain | 4.29E-15 | 16.35 |

TABLE 5-continued

Significant CNAs in mut-KIT tumors identified by GISTIC analysis

| No. | Region | Extended Region | Type | Q-Bound | G-Score |
|---|---|---|---|---|---|
| 47 | chr26: 27,174,566-27,207,467 | chr26: 27,174,566-27,240,032 | Loss | 1.34E−09 | 38.88 |
| 48 | chr27: 6,978,563-7,041,668 | chr27: 6,954,304-7,041,668 | Gain | 1.04E−02 | 4.58 |
| 49 | chr28: 39,142,525-39,236,726 | chr28: 36,947,617-40,499,923 | Loss | 3.96E−06 | 9.32 |
| 50 | chr29: 40,988,530-41,067,224 | chr29: 40,654,989-41,845,238 | Loss | 3.12E−02 | 4.17 |
| 51 | chr31: 28,109,184-28,150,222 | chr31: 20,869,268-35,611,912 | Gain | 4.29E−15 | 13.43 |
| 52 | chr32: 1,665,965-2,024,718 | chr32: 1-2,989,645 | Loss | 5.58E−03 | 5.54 |
| 53 | chr33: 14,686,038-14,789,970 | chr33: 1,117,447-23,505,256 | Loss | 9.49E−04 | 6.45 |
| 54 | chr36: 19,878,982-19,955,258 | chr36: 6,988,336-23,357,555 | Gain | 2.17E−06 | 8.36 |
| 55 | chr37: 24,954,721-24,972,543 | chr37: 24,943,587-25,049,058 | Gain | 2.08E−02 | 4.01 |
| 56 | chr37: 30,312,057-30,452,090 | chr37: 30,312,057-30,902,991 | Loss | 5.22E−03 | 5.59 |
| 57 | chr38: 1,056,312-1,123,624 | chr38: 697,930-1,163,327 | Gain | 4.64E−04 | 6.60 |
| 58 | chrX: 407,533-427,889 | chrX: 1,427,889 | Loss | 4.07E−02 | 3.99 |
| 59 | chrX: 32,269,966-32,297,891 | chrX: 32,202,589-32,328,959 | Loss | 9.28E−04 | 6.46 |
| 60 | chrX: 71,762,610-71,780,002 | chrX: 71,744,008-72,105,721 | Gain | 8.83E−06 | 7.95 |
| 61 | chrX: 71,780,002-72,216,345 | chrX: 71,744,008-72,228,723 | Loss | 1.34E−09 | 27.09 |
| 62 | chrX: 120,981,052-121,072,550 | chrX: 120,908,381-121,071,550 | Loss | 7.22E−03 | 5.38 |

TABLE 6

CNV to differentiate wt-KIT high-grade tumors vs wt-KIT low-grade tumors

| Region | Event | Length | wt-KIT high freq (%) | wt-KIT low freq (%) | Gene Symbols |
|---|---|---|---|---|---|
| ch20: 31,578,503-31,734,123 | CN Loss | 155,618 | 77.3 | 5.6 | LOC100685571, C20H3orf67 |
| chr20: 46,389,048-46,464,109 | CN Gain | 75,061 | 81.8 | 9.3 | OR10A11, OR18C09, LOC102155605 |

CNV to differentiate Mut-KIT tumors vs wt-KIT low-grade tumors

| Region | Event | Region Length | Mut-KIT freq (%) | wt-KIT low freq (%) | Gene Symbols |
|---|---|---|---|---|---|
| chr5: 37,788,55-37,966,845 | CN Loss | 178,293 | 75.8 | 0 | COX10 |
| chr31: 16,653,042-16,851,394 | CN Gain | 198,352 | 63.6 | 0 | |

8. SEQUENCE LISTING

Incorporation-by-Reference of Material Submitted Electronically

This application contains a sequence listing. It has been submitted electronically via EFS-Web as an ASCII text file entitled "127-97-PCT_2017-05-26_SEQ_ST25.txt". The sequence listing is 5322 bytes in size, and was created on May 26, 2017. It is hereby incorporated by reference in its entirety.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world. It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed is:

1. A kit for detecting a high-risk phenotype of a mast cell tumor (MCT) in a biological sample isolated from a dog, the kit comprising nucleic acid probes, primers, or pairs of primers, wherein the nucleic acid probes, primers, or pairs of primers consist of:
   first nucleic acid probe, primer, or pair of primers capable of specifically detecting canine chromosomal region CFA 5:38 of CanFam v3 in the biological sample isolated from the dog;
   a second nucleic acid probe, primer or pair of primers capable of specifically detecting canine chromosomal region CFA 31:18 of CanFam v3 in the biological sample isolated from the dog;
   a third nucleic acid probe, primer or pair of primers capable of specifically detecting canine chromosomal region CFA 20:32 of CanFam v3 in the biological sample isolated from the dog;
   a fourth nucleic acid probe, primer or pair of primers capable of specifically detecting canine chromosomal region CFA 20:46 of CanFam v3 in the biological sample isolated from the dog, and
   an optional fifth nucleic acid probe, primer or pair of primers capable of specifically detecting a canine chromosomal region other than CFA 5:38, CFA 31:18, CFA 20:32, and CFA 20:46 of CanFam v3 in the biological sample isolated from the dog to serve as a control,
   and further wherein the first, second, third, fourth, and the optional fifth nucleic acid probes, primers, or pairs of primers are differentially fluorescently labeled.

2. The kit of claim 1, wherein the biological sample comprises cancer cells and/or DNA isolated therefrom, optionally wherein the cancer cells are isolated from the bone marrow, skin, lungs, nose, and/or mouth of the dog.

3. The kit of claim 1, wherein the biological sample is a biopsy.

4. The kit of claim 1, wherein the biological sample is a cytological smear, a fresh-frozen sample, a fresh sample, a fixed sample, and/or a paraffin-embedded sample.

5. The kit of claim 1, wherein the kit further comprises one or more additional components selected from the group consisting of blocking agents, detectable labels or labeling agents, and reagents for hybridization of the first, second, third, fourth, and optional fifth nucleic acid probes, primers, or pairs of primers to CFA 5:38, CFA 31:18, CFA 20:32, CFA 20:46, and a canine chromosomal region other than CFA 5:38, CFA 31:18, CFA 20:32, and CFA 20:46, respectively, of CanFam v3 in the biological sample.

6. A kit for detecting a high-risk phenotype of a mast cell tumor (MCT) in a biological sample isolated from a dog, the kit comprising nucleic acid probes, primers, or pairs of primers, wherein the nucleic acid probes, primers, or pairs of primers consist of:
- a first nucleic acid probe, primer, or pair of primers capable of specifically detecting canine chromosomal region CFA 5:38 of CanFam v3 in the biological sample isolated from the dog;
- a second nucleic acid probe, primer or pair of primers capable of specifically detecting canine chromosomal region CFA 31:18 of CanFam v3 in the biological sample isolated from the dog;
- a third nucleic acid probe, primer or pair of primers capable of specifically detecting canine chromosomal region CFA 20:32 of CanFam v3 in the biological sample isolated from the dog;
- a fourth nucleic acid probe, primer or pair of primers capable of specifically detecting canine chromosomal region CFA 20:46 of CanFam v3 in the biological sample isolated from the dog, and
- an optional fifth nucleic acid probe, primer or pair of primers capable of specifically detecting a canine chromosomal region other than CFA 5:38, CFA 31:18, CFA 20:32, and CFA 20:46 of CanFam v3 in the biological sample isolated from the dog to serve as a control,
- and further wherein the first, second, third, fourth, and the optional fifth nucleic acid probes, primers, or pairs of primers are differentially fluorescently labeled and appropriate for use in measuring copy numbers of CFA 5:38, CPA CFA 31:18, CPA CFA 20:32, CPA CFA 20:46, and a canine chromosomal region other than CFA 5:38, CFA 31:18, CFA 20.32, and CFA 20:46 by a technique selected from the group consisting of fluorescence in situ hybridization (FISH), polymerase chain reaction (PCR), comparative genomic hybridization (CGH), Serial Analysis of Gene Expression (SAGE), bead-based technologies, single molecule fluorescence in situ hybridization (smFISH) studies, gene expression analysis by massively parallel signature sequencing, next generation sequencing, or droplet digital PCR (ddPCR).

7. The kit of claim 6, wherein the first, second, third, fourth, and optional fifth nucleic acid probes, primers, or pairs of primers are appropriate for use in measuring copy numbers of CFA 5:38, 31:18, CFA 20:32, CFA 20:46, and a canine chromosomal region other than CFA 5:38, CFA 31:18, CFA 20.32, and CFA 20:46 by droplet digital PCR (ddPCR).

8. The kit of claim 1, wherein the nucleic acid probes, primers, or pairs of primers consist of a first nucleic acid probe, primer, or pair of primers that is capable of specifically detecting copy number at CFA 5:38: a second nucleic acid probe, primer, or pair of primers that is capable of specifically detecting copy number at CPA 31:18; a third nucleic acid probe, primer, or pair of primers that is capable of specifically detecting copy number at CPA 20:32; a fourth nucleic acid probe, primer, or pair of primers that is capable of specifically detecting copy number at CFA 20:46; and a fifth nucleic acid probe, primer, or pair of primers that is capable of specifically detecting copy number at a canine chromosomal region other than CFA 5:38, CFA 31:18, CFA 20.32, and CFA 20:46.

9. The kit of claim 1, wherein the kit further comprises instructions for use of the kit in measuring copy numbers of CFA 5:38, CFA 31:18, CFA 20:32, CFA 20:46 of CanFam v3, and optionally a dog chromosome other than CFA 5, CFA 20, or CFA 31 in the biological sample.

* * * * *

SEQUENCE LISTING

```
<160> NUMBER OF SEQ ID NOS: 18

<210> SEQ ID NO 1
<211> LENGTH: 20
<212> TYPE: DNA
```

```
<213> ORGANISM: Artificial Sequence
<220> FEATURE:
<223> OTHER INFORMATION: Artificially synthesized sequence

<400> SEQUENCE: 1
ggtgaggtgt tccagcagtc                                             20

<210> SEQ ID NO 2
<211> LENGTH: 20
<212> TYPE: DNA
<213> ORGANISM: Artificial Sequence
<220> FEATURE:
<223> OTHER INFORMATION: Artificially synthesized sequence

<400> SEQUENCE: 2
acgtatgcca attccaatgt                                             20

<210> SEQ ID NO 3
<211> LENGTH: 26
<212> TYPE: DNA
<213> ORGANISM: Artificial Sequence
<220> FEATURE:
<223> OTHER INFORMATION: Artificially synthesized sequence

<400> SEQUENCE: 3
aaagatgatc tgtctctctt ttctcc                                      26

<210> SEQ ID NO 4
<211> LENGTH: 20
<212> TYPE: DNA
<213> ORGANISM: Artificial Sequence
<220> FEATURE:
<223> OTHER INFORMATION: Artificially synthesized sequence

<400> SEQUENCE: 4
ttgcctagag tatggcgaag                                             20

<210> SEQ ID NO 5
<211> LENGTH: 21
<212> TYPE: DNA
<213> ORGANISM: Artificial Sequence
<220> FEATURE:
<223> OTHER INFORMATION: Artificially synthesized sequence

<400> SEQUENCE: 5
gggttaccca aagtagtctg a                                           21

<210> SEQ ID NO 6
<211> LENGTH: 23
<212> TYPE: DNA
<213> ORGANISM: Artificial Sequence
<220> FEATURE:
<223> OTHER INFORMATION: Artificially synthesized sequence

<400> SEQUENCE: 6
aaggttctta gcacagagga atc                                         23

<210> SEQ ID NO 7
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 7
agctggattt acaaatagca ctttc                                       25
```

```
<210> SEQ ID NO 8
<211> LENGTH: 19
<212> TYPE: DNA
<213> ORGANISM: Artificial Sequence
<220> FEATURE:
<223> OTHER INFORMATION: Artificially synthesized sequence

<400> SEQUENCE: 8
ccttccctcg tgcacatta                                                19

<210> SEQ ID NO 9
<211> LENGTH: 20
<212> TYPE: DNA
<213> ORGANISM: Artificial Sequence
<220> FEATURE:
<223> OTHER INFORMATION: Artificially synthesized sequence

<400> SEQUENCE: 9
gccattgatg gaatggactt                                               20

<210> SEQ ID NO 10
<211> LENGTH: 21
<212> TYPE: DNA
<213> ORGANISM: Artificial Sequence
<220> FEATURE:
<223> OTHER INFORMATION: Artificially synthesized sequence

<400> SEQUENCE: 10
gaagctaatg gggttcccta a                                             21

<210> SEQ ID NO 11
<211> LENGTH: 22
<212> TYPE: DNA
<213> ORGANISM: Artificial Sequence
<220> FEATURE:
<223> OTHER INFORMATION: Artificially synthesized sequence

<400> SEQUENCE: 11
gtcatgtgtt agcagagaga ga                                            22

<210> SEQ ID NO 12
<211> LENGTH: 24
<212> TYPE: DNA
<213> ORGANISM: Artificial Sequence
<220> FEATURE:
<223> OTHER INFORMATION: Artificially synthesized sequence

<400> SEQUENCE: 12
tactttgtct tcctggttgt aact                                          24

<210> SEQ ID NO 13
<211> LENGTH: 22
<212> TYPE: DNA
<213> ORGANISM: Artificial Sequence
<220> FEATURE:
<223> OTHER INFORMATION: Artificially synthesized sequence

<400> SEQUENCE: 13
aacatcctat gctctgcttc tg                                            22

<210> SEQ ID NO 14
<211> LENGTH: 23
<212> TYPE: DNA
<213> ORGANISM: Artificial Sequence
<220> FEATURE:
```

-continued

```
<223> OTHER INFORMATION: Artificially synthesized sequence

<400> SEQUENCE: 14
ggaagagaag gcaatgaata gga                                               23

<210> SEQ ID NO 15
<211> LENGTH: 24
<212> TYPE: DNA
<213> ORGANISM: Artificial Sequence
<220> FEATURE:
<223> OTHER INFORMATION: Artificially synthesized sequence

<400> SEQUENCE: 15
ttggctgttc tctctgtgtc cgtt                                              24

<210> SEQ ID NO 16
<211> LENGTH: 26
<212> TYPE: DNA
<213> ORGANISM: Artificial Sequence
<220> FEATURE:
<223> OTHER INFORMATION: Artificially synthesized sequence

<400> SEQUENCE: 16
tttggctacc cttcctaaga cacagc                                            26

<210> SEQ ID NO 17
<211> LENGTH: 24
<212> TYPE: DNA
<213> ORGANISM: Artificial Sequence
<220> FEATURE:
<223> OTHER INFORMATION: Artificially synthesized sequence

<400> SEQUENCE: 17
ttctcttctc aggccgttcc gttt                                              24

<210> SEQ ID NO 18
<211> LENGTH: 28
<212> TYPE: DNA
<213> ORGANISM: Artificial Sequence
<220> FEATURE:
<223> OTHER INFORMATION: Artificially synthesized sequence

<400> SEQUENCE: 18
tgtgagattt gcattacatg accctgga                                          28
```